United States Patent
Watanabe et al.

(10) Patent No.: US 9,527,859 B2
(45) Date of Patent: Dec. 27, 2016

(54) AMIDOPYRIDINE DERIVATIVE AND USE THEREOF

(71) Applicant: Mitsubishi Tanabe Pharma Corporation, Osaka-shi (JP)

(72) Inventors: Masayuki Watanabe, Setagaya-ku (JP); Hiroyuki Furukawa, Kawasaki (JP); Maiko Hamada, Yamato (JP); Naoto Fujie, Kobe (JP); Hiroyuki Ushio, Takarazuka (JP); Tooru Takashima, Yokohama (JP)

(73) Assignee: MITSUBISHI TANABE PHARMA CORPORATION, Osaka-shi (JP)

( * ) Notice: Subject to any disclaimer, the term of this patent is extended or adjusted under 35 U.S.C. 154(b) by 0 days.

(21) Appl. No.: 14/391,998

(22) PCT Filed: Apr. 12, 2013

(86) PCT No.: PCT/JP2013/061024
§ 371 (c)(1),
(2) Date: Oct. 10, 2014

(87) PCT Pub. No.: WO2013/154173
PCT Pub. Date: Oct. 17, 2013

(65) Prior Publication Data
US 2015/0065715 A1    Mar. 5, 2015

(30) Foreign Application Priority Data
Apr. 13, 2012  (JP) ................................ 2012-092167

(51) Int. Cl.
| C07D 491/113 | (2006.01) |
| C07D 401/14  | (2006.01) |
| C07D 409/14  | (2006.01) |
| C07D 417/14  | (2006.01) |

(52) U.S. Cl.
CPC ......... *C07D 491/113* (2013.01); *C07D 401/14* (2013.01); *C07D 409/14* (2013.01); *C07D 417/14* (2013.01)

(58) Field of Classification Search
None
See application file for complete search history.

(56) References Cited

U.S. PATENT DOCUMENTS

| 7,015,218 B1 | 3/2006 | Ushio et al. |
| 2006/0173021 A1 | 8/2006 | Sun et al. |
| 2009/0105264 A1 | 4/2009 | Hamblett et al. |
| 2010/0125080 A1 | 5/2010 | Bohnert et al. |
| 2010/0152445 A1 | 6/2010 | Bolin et al. |
| 2010/0190979 A1* | 7/2010 | Bolin ............... C07D 413/14 544/122 |
| 2011/0118281 A9 | 5/2011 | Bohnert et al. |
| 2011/0195934 A1 | 8/2011 | Devasthale et al. |
| 2012/0183579 A1 | 7/2012 | Bohnert et al. |
| 2013/0211075 A1 | 8/2013 | Ushio et al. |

FOREIGN PATENT DOCUMENTS

| EP | 1 176 140 A1 | 1/2002 |
| EP | 1 310 488 A1 | 5/2003 |
| JP | 2001-220390 A | 8/2001 |
| JP | 2002-338537 A | 11/2002 |
| JP | 2008-528520 A | 7/2008 |
| JP | 2009-514859 A | 4/2009 |
| WO | WO 00/47558 A1 | 8/2000 |
| WO | WO 2004/002948 A1 | 1/2004 |
| WO | WO 2006/081391 A2 | 8/2006 |
| WO | WO 2006/081391 A3 | 8/2006 |
| WO | WO 2007/055942 A2 | 5/2007 |
| WO | WO 2007/055942 A3 | 5/2007 |
| WO | WO 2007/060140 A2 | 5/2007 |
| WO | WO 2008/141976 A1 | 11/2008 |

(Continued)

OTHER PUBLICATIONS

A.M. Bendele "Animal models of rheumatoid arthritis" J Musculoskel Neuron Interact 2001; 1(4):377-385.*
Georg Pilz, "Modern multiple sclerosis treatment—what is approved, what is on the horizon" Drug Discovery Today Dec. 2008, vol. 13, Nos. 23/24 1013-1025.*
Geyer "ACR: Anti-IL17 Drug Misses Endpoint in RA Trial" MedPage Today Meeting Coverage Nov. 10, 2010 Online: "http://www.medpagetoday.com/MeetingCoverage/ACR/23290" accessed Aug. 20, 2015.*
George A. Patani "Bioisosterism: A Rational Approach in Drug Design" Chemical Reviews 1996, 96, 3147-3176.*
Wermuth, Camille G. "Molecular Variation Based on Isosteric Replacements" in Chapter 13, The Practice of Medicinal Chemistry, Academic: 1996.*

(Continued)

*Primary Examiner* — David K O'Dell
(74) *Attorney, Agent, or Firm* — Oblon, McClelland, Maier & Neustadt, L.L.P.

(57) ABSTRACT

The present invention relates to novel amidopyridine derivatives. More specifically, the present invention provides a medicinal agent which is useful as a prophylactic or therapeutic agent for diseases based on the production of cytokines from T cells, comprising as the active ingredient an amidopyridine derivative or a pharmacologically acceptable salt thereof. Provided are an amidopyridine derivative of the following general formula (I):

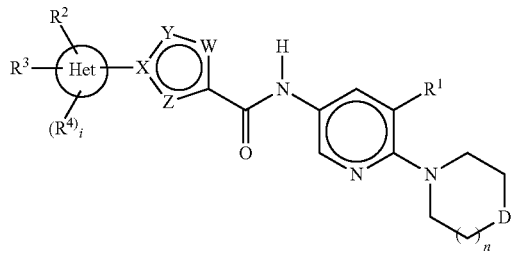

wherein each symbol has the same meaning as defined in the description, or a pharmacologically acceptable salt thereof.

10 Claims, No Drawings

(56) References Cited

FOREIGN PATENT DOCUMENTS

| WO | WO 2010/039236 A1 | 4/2010 |
|---|---|---|
| WO | WO 2010/047956 A1 | 4/2010 |
| WO | WO 2010/059611 A2 | 5/2010 |
| WO | WO 2010/077861 A1 | 7/2010 |
| WO | WO 2012/050159 A1 | 4/2012 |

OTHER PUBLICATIONS

Nakamura "Imidazole derivatives as new potent and selective 20-HETE synthase inhibitors." Bioorganic & Medicinal Chemistry Letters 2004, 14, 333-336.*

Li "N-(Arylacetyl)-biphenylalanines as Potent VLA-4 Antagonists" Bioorganic & Medicinal Chemistry Letters 2002, 12, 2141-2144.*

International Preliminary Report on Patentability and Written Opinion issued Oct. 23, 2014 in PCT/JP2013/061024 English Translation only).

International Search Report issued Jun. 18, 2013 in PCT/JP2013/061024.

Maria Ziolkowska et al., "High Levels of IL-17 in Rheumatoid Arthritis Patients: IL-15 Triggers in Vitro IL-17 Production Via Cyclosporin A-Sensitive Mechanism", J. Immunol., vol. 164, 2000, pp. 2832-2838 and Cover page.

Susumu Nakae et al., "Suppression of Immune Induction of Collagen-Induced Arthritis in IL-17-Deficient Mice", J. Immunol., vol. 171, 2003, pp. 6173-6177 and Cover page.

Erik Lubberts et al., "Treatment With a Neutralizing Anti-Murine Interleukin-17 Antibody After the Onset of Collagen-Induced Arthritis Reduces Joint Inflammation, Cartilage Destruction, and Bone Erosion", Arthritis & Rheumatism, vol. 50, No. 2, Feb. 2004, pp. 650-659.

Erik Lubberts, "The Role of IL-17 and Family Members in the Pathogenesis of Arthritis", Current Opinion in Investigational Drugs, vol. 4, 2003, pp. 572-577.

B. Afzali et al., "The Role of T helper 17 (Th17) and Regulatory T cells (Treg) in Human Organ Transplantation and Autoimmune Disease", Clinical and Experimental Immunology, vol. 148, 2007, pp. 32-46.

Yutaka Komiyama et al., "IL-17 Plays an Important Role in the Development of Experimental Autoimmune Encephalomyelitis", J. Immunol., vol. 177, 2006, pp. 566-573, and Cover page.

Zili Zhang et al., "Critical Role of IL-17 Receptor Signaling in Acute TNBS-induced Colitis", Inflamm. Bowel Dis. ,vol. 12, No. 5, May 2006, pp. 382-388.

Susumu Nakae et al., "Antigen-Specific T Cell Sensitization Is Impaired in IL-17-Deficient Mice, Causing Suppression of Allergic Cellular and Humoral Responses", Immunity, vol. 17, Sep. 2002, pp. 375-387.

Mi-La Cho et al., "Cyclosporine a Inhibits IL-15-induced IL-17 Production in $CD4^+$ T Cells via Down-regulation of PI3K/Akt and $NF-_{\kappa}B$", Immunology Letters, vol. 108, 2007, pp. 88-96.

Cai Zhang et al., "Cyclosporin A Inhibits the Production of IL-17 by Memory Th17 Cells from Healthy Individuals and Patients with Rheumatoid Arthritis", Cytokine, vol. 42, 2008, pp. 345-352.

Hiroyuki Ushio et al., Phenylpyazoleanilides as Potent Inhibitor of IL-15 Dependent T Cell Proliferation. Part 2: Discovery of a New Drug Candidate, Y-320, Letters in Drug Design & Discovery, vol. 5, 2008, pp. 292-296.

Extended European Search Report issued Oct. 12, 2015 in Patent Application No. 13775747.2.

* cited by examiner

AMIDOPYRIDINE DERIVATIVE AND USE THEREOF

TECHNICAL FIELD

The present invention relates to novel amidopyridine derivatives. More specifically, it relates to an inhibitor for activated lymphocyte proliferation, comprising as the active ingredient a novel amidopyridine derivative or a pharmacologically acceptable salt thereof, or a solvate thereof.

The present invention relates to useful amidopyridine compounds which allow prophylaxis and/or treatment of autoimmune diseases and inflammatory/allergic diseases by inhibiting the production of cytokines from T cells, particularly the production of interleukin 17 (also referred to as "IL-17" hereinafter), and their medical use.

BACKGROUND ART

Autoimmune diseases are believed to be induced by the incomplete removal of self-reactive lymphocytes in thymus glands. Among them, rheumatoid arthritis (also referred to as "RA" hereinafter) is a progressive inflammatory disease where joint pain•swelling•inflammation systemically spread for unknown reasons, and subsequently deformity•destruction of joint becomes advanced as these conditions continue, and finally physical disability is triggered. A major pathology of RA is synovium, and synoviocytes that compose synovium are proliferated, which gradually affects the surrounding cartilage•bone to cause destruction and deformity of joint.

IL-17, and IL-15 which induces the same have been confirmed in high concentrations in synovial fluid of RA patients, and have been indicated to be involved in inflammation, bone destruction (Nonpatent document 1). It has been also reported that the incidence of arthritis in IL-17-deficient mice is significantly suppressed compared to wild-type mice in type II collagen-induced arthritis model (Nonpatent document 2), and that the arthritis scores are significantly suppressed when anti-mouse IL-17-neutralizing antibody is prophylactically or therapeutically administered to type II collagen-induced mice arthritis model (Nonpatent document 3), etc. IL-17 also activates synoviocytes and chondrocytes to promote the production of cytokines or chemokines such as IL-1, TNF-γ and osteoclast differentiation factor (RANKL). Further, IL-17 has been considered to be involved in the induction of collagenolytic enzymes from these cells to induce joint destruction (Nonpatent document 4). Accordingly, it is considered that IL-17 is closely involved in the development and progress of rheumatoid arthritis.

In addition to rheumatoid arthritis, it has been recognized that IL-17 was produced or its expression was increased in multiple sclerosis, systemic lupus erythematosus, psoriasis, inflammatory bowel disease, transplantation rejection, asthma, etc. (Nonpatent document 5). It has been also reported that pathogenesis of mouse experimental encephalomyelitis (EAE) in IL-17-deficient mice is significantly suppressed compared to wild-type mice in EAE model (Nonpatent document 6), and inflammation of bowel in IL-17R-deficient mice is also reduced in TNBS-induced mouse enteritis model as well (Nonpatent document 7). Further, each reaction in IL-17-deficient mice was also reduced compared to wild-type mice in trinitrochlorobenzene-induced contact-type hypersensitivity, methylated bovine serum albumin-induced delayed-type hypersensitivity and ovalbumin-induced reactive airway disease (Nonpatent document 8). These facts indicated that IL-17 is also involved in autoimmune diseases and inflammatory/allergic diseases such as multiple sclerosis, systemic lupus erythematosus, psoriasis, inflammatory bowel disease.

Accordingly, it is considered that controlling the production of IL-17 from T cells is useful for a prophylactic and/or therapeutic agent for autoimmune diseases and inflammatory/allergic diseases such as multiple sclerosis, systemic lupus erythematosus, psoriasis, inflammatory bowel disease as well as rheumatoid arthritis.

As mentioned above, it has been indicated that IL-17 generated from T cells is deeply involved in various autoimmune diseases and inflammatory/allergic diseases including rheumatoid arthritis. Hence, it is believed that compounds controlling the production of IL-17 from T cells show remarkable effects on prophylaxis and/or treatment of various autoimmune diseases and inflammatory/allergic diseases.

Cyclosporin has been known as a compound controlling the production of IL-17 (Nonpatent documents 9, 10). Cyclosporin inhibits the activation of calcineurin by forming a complex with intracellular binding protein, cyclophilin. As a result, the intranuclear localization by dephosphorylation of transcription factor NF-AT such as IL-2 is inhibited, and the production of cytokines from T cells is suppressed. As to cyclosporin, therapeutic effects for autoimmune diseases have been already recognized, but side effects such as renal disorder have been seen as a problem. A therapeutic agent for autoimmune diseases with showing more remarkable therapeutic effects and with fewer side effects has been desired especially in RA area, etc. for which prolonged administration is required.

On the other hand, specific amide derivatives with lymphocytic antiproliferative effects have been reported in Nonpatent document 11 and Patent documents 1 to 4, nevertheless, they have different structures from the present invention. In Patent documents 5 to 7, no lymphocytic antiproliferative effects are mentioned, and compounds with different structures from the present invention are reported.

BACKGROUND ART DOCUMENTS

Patent Documents

Patent document 1: WO 00/047558 pamphlet
Patent document 2: WO 02/012189 pamphlet
Patent document 3: JP-A-2002-338537
Patent document 4: WO 04/002948 pamphlet
Patent document 5: WO 07/060,140 pamphlet
Patent document 6: WO 08/141,976 pamphlet
Patent document 7: WO 10/077,861 pamphlet

Non Patent Documents

Nonpatent document 1: J. Immunol., vol. 164. pp. 2832-2838, 2000
Nonpatent document 2: J. Immunol., vol. 171, pp. 6173-6177, 2003
Nonpatent document 3: Arithritis & Rheum., vol. 50, pp. 650-659, 2004
Nonpatent document 4: Current Opinion in Investigtional Drugs, vol. 4, pp. 572-577, 2003
Nonpatent document 5: Clinical and Experimental Immunol., vol. 148, pp. 32-46, 2007
Nonpatent document 6: J. Immunol., vol. 177, pp. 566-573, 2006

Nonpatent document 7: Inflamm. Bowel Dis., vol. 12, pp. 382-388, 2006

Nonpatent document 8: Immunity, vol. 17, pp. 375-387, 2002

Nonpatent document 9: Immunol Lett., vol. 108, pp. 88-96, 2007

Nonpatent document 10: Cytokine, vol. 42, pp. 345-352, 2008

Nonpatent document 11: Letters in Drug Design & Discovery, vol. 5, pp. 292-296, 2008

SUMMARY OF INVENTION

Problems to be Solved by the Invention

The present invention provides amidopyridine derivatives or pharmacologically acceptable salts thereof as well as IL-17 production inhibitors which are useful for prophylaxis and/or treatment of diseases involving IL-17 production.

Means of Solving the Problems

The present inventors have made intensive studies to solve the above problems, and then have found that specific amidopyridine derivatives may achieve the desired objects such as inhibition of IL-17 production from T cells and avoidance of toxicities represented by hERG inhibitory activity or hepatocyte toxicity and have achieved the present invention.

Particularly, the present invention relates to the following amidopyridine derivatives or pharmacologically acceptable salts thereof, and their use.

The present invention relates to pharmaceuticals, especially to useful amidopyridine derivatives which enable the prophylaxis and/or treatment of autoimmune diseases and inflammatory/allergic diseases by controlling or inhibiting the production of Interleukin 17 (IL-17), or pharmacologically acceptable salts thereof, and their medical use.

(1) A compound of the following general formula (I)

[Chemical Formula 1]

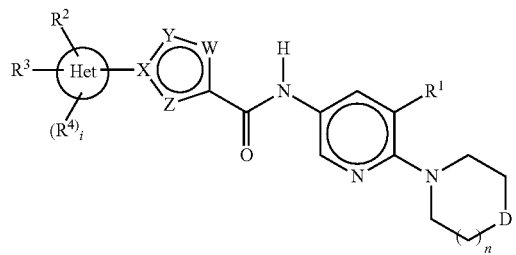

(I)

wherein X is N, or C,

Y is N, N—$R^Y$, S, or C—$R^Y$,

Z is N, N—$R^Z$, S, or C—$R^Z$,

W is N, N—$R^W$, S, or C—$R^W$, provided that at least one of X, Y, Z, W is N or S, $R^Y$, $R^Z$ and $R^W$ are each independently selected from hydrogen atom, alkyl group, haloalkyl group, or cycloalkyl group, $R^1$ is halogen atom, alkyl group, cyano group, or cycloalkyl group, n is an integer of 0 to 2, Het is cycloalkyl group, aryl group, heterocycle group, or heteroaryl group, $R^2$, $R^3$ and $R^4$ are each independently selected from hydrogen atom, halogen atom, cyano group, hydroxy group, alkyl group, haloalkyl group, alkoxy group, or cycloalkyl group.

i is an integer of 0 to 3,

D is any one of the following general formulae

[Chemical Formula 2]

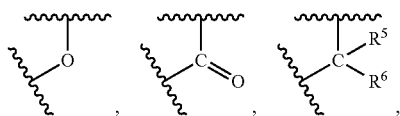

$R^5$ and $R^6$ are each independently selected from hydrogen atom, hydroxy group, cyano group, optionally substituted alkyl group, optionally substituted alkoxy group, optionally substituted cycloalkyl group, -L-$NR^{7a}R^{7b}$, -L-$NR^{7a}$—CO—$R^{7b}$, -L-CO—$NR^{7a}R^{7b}$, or -L-O—CO—$R^{7c}$ [in which $R^{7a}$ and $R^{7b}$ are each independently selected from hydrogen atom or alkyl group. $R^{7c}$ is alkyl group or phenyl group, L is a bond, or —$(CR_A R_B)_j$— (in which j is an integer of 1 to 4, $R_A$ and $R_B$ are each independently selected from hydrogen atom or alkyl group)], or $R^5$ and $R^6$ are optionally combined with each other to form optionally substituted cycloalkyl group, or optionally substituted heterocycle group, or a pharmacologically acceptable salt thereof.

(2) The compound of the above (1), wherein Het is aryl group or heteroaryl group, or a pharmacologically acceptable salt thereof.

(3) The compound of the above (1) or (2), wherein n is 1, or a pharmacologically acceptable salt thereof.

(4) The compound of any one of the above (1) to (3), wherein D is any group of the following general formulae, or a pharmacologically acceptable salt thereof.

[Chemical formula 3]

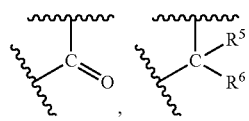

(5) The compound of any one of the above (1) to (4), wherein X is N, or a pharmacologically acceptable salt thereof.

(6) The compound of any one of the above (1) to (5), wherein $R^1$ is alkyl group or cycloalkyl group, or a pharmacologically acceptable salt thereof.

(7) A compound of the following general formula (I)a

[Chemical formula 4]

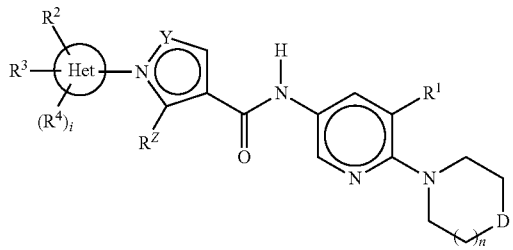

(I)a wherein Y is N or C—$R^Y$, $R^Y$ and $R^Z$ are each independently selected from hydrogen atom, alkyl group, haloalkyl group, or cycloalkyl group, $R^1$ is halogen atom, alkyl group, cyano group, or cycloalkyl group, n is an integer of 0 to 2, Het is cycloalkyl group, aryl group, heterocycle group, or heteroaryl group, $R^2$, $R^3$ and $R^4$ are each independently selected from hydrogen atom, halogen atom, cyano group, hydroxy group, alkyl group, haloalkyl group, alkoxy group, or cycloalkyl group, i is an integer of 0 to 3, D is any group of the following general formulae

[Chemical formula 5]

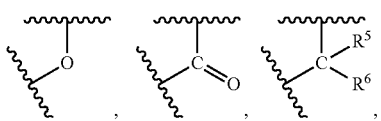

$R^5$ and $R^6$ are each independently selected from hydrogen atom, hydroxy group, cyano group, optionally substituted alkyl group, optionally substituted alkoxy group, optionally substituted cycloalkyl group, -L-$NR^{7a}R^{7b}$, -L-$NR^{7a}$—CO—$R^{7b}$, -L-CO—$NR^{7a}R^{7b}$, or -L-O—CO—$R^{7c}$ [in which $R^{7a}$ and $R^{7b}$ are each independently selected from hydrogen atom or alkyl group, $R^{7c}$ is alkyl group or phenyl group, L is a bond, or —$(CR_AR_B)_j$— (in which j is an integer of 1 to 4, $R_A$ and $R_B$ are each independently selected from hydrogen atom or alkyl group)], or $R^5$ and $R^6$ are optionally combined with each other to form optionally substituted cycloalkyl group, or optionally substituted heterocycle group, or a pharmacologically acceptable salt thereof.

(8) The compound of the above (7), wherein Het is aryl group or heteroaryl group, or a pharmacologically acceptable salt thereof.

(9) The compound of the above (7) or (8), wherein n is 1, or a pharmacologically acceptable salt thereof.

(10) The compound of any one of the above (7) to (9), wherein D is a group of the following general formula, or a pharmacologically acceptable salt thereof.

[Chemical formula 6]

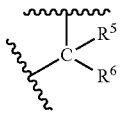

(11) The compound of any of the above (7) to (10), wherein $R^1$ is alkyl group or cycloalkyl group, or a pharmacologically acceptable salt thereof.

(12) A compound selected from the following group or a pharmacologically acceptable salt thereof N-[5-cyclopropyl-6-(4-hydroxypiperidin-1-yl)pyridin-3-yl]-1-(2,4-dichlorophenyl)-5-methyl-1H-pyrazole-4-carboxamide;

N-[6-(4-hydroxypiperidin-1-yl)-5-methylpyridin-3-yl]-5-methyl-1-[4-(trifluoromethyl)phenyl]-1H-pyrazole-4-carboxamide;

1-(4-chlorophenyl)-N-[6-(4-methoxypiperidin-1-yl)-5-methylpyridin-3-yl]-5-methyl-1H-pyrazole-4-carboxamide;

N-{5-cyclopropyl-6-[4-(2-hydroxyethyl)piperidin-1-yl]pyridin-3-yl}-1-(4-fluorophenyl)-5-methyl-1H-pyrazole-4-carboxamide;

acetic acid (1-{5-[1-(4-chlorophenyl)-5-methyl-1H-pyrazole-4-carboxamide]-3-cyanopyridin-2-yl}piperidin-4-yl)ester;

1-(4-chlorophenyl)-N-[5-cyano-6-(4-oxopiperidin-1-yl)pyridin-3-yl]-5-methyl-1H-pyrazole-4-carboxamide;

N-{6-[4-(1-methoxymethyl)piperidin-1-yl]-5-methylpyridin-3-yl}-5-methyl-1-[4-(trifluoromethyl)phenyl]-1H-pyrazole-4-carboxamide;

N-[5-chloro-6-(4-hydroxypiperidin-1-yl)pyridin-3-yl]-1-(4-chlorophenyl)-5-methyl-1H-pyrazole-4-carboxamide;

1-(4-chlorophenyl)-N-[5-cyclopropyl-6-(4-hydroxypiperidin-1-yl)pyridin-3-yl]-5-methyl-1H-pyrazole-4-carboxamide;

acetic acid [2-(1-{5-[1-(4-chlorophenyl)-5-methyl-1H-pyrazole-4-carboxamide]-3-cyanopyridin-2-yl}piperidin-4-yl)ethyl]ester;

1-(4-chlorophenyl)-N-[6-(4-hydroxypiperidin-1-yl)-5-methylpyridin-3-yl]-5-methyl-1H-pyrazole-4-carboxamide;

1-(4-chlorophenyl)-N-[5-cyano-6-(4-hydroxypiperidin-1-yl)pyridin-3-yl]-5-methyl-1H-pyrazole-4-carboxamide;

N-[5-cyano-6-(4-hydroxypiperidin-1-yl)pyridin-3-yl]-5-methyl-1-[4-(trifluoromethyl)phenyl]-1H-pyrazole-4-carboxamide;

1-(5-cyanopyridin-2-yl)-N-{6-[4-(1-hydroxy-1-methylethyl)piperidin-1-yl]-5-methylpyridin-3-yl}-1H-pyrrole-3-carboxamide;

1-(4-chlorophenyl)-N-{5-cyano-6-[4-(2-hydroxyethyl)piperidin-1-yl]pyridin-3-yl}-5-methyl-1H-pyrazole-4-carboxamide.

(13) An IL-17 production inhibitor, comprising as the active ingredient the compound of any of the above (1) to (12) or a pharmacologically acceptable salt thereof.

(14) A prophylactic agent and/or therapeutic agent for autoimmune disease, comprising as the active ingredient the compound of any of the above (1) to (12) or a pharmacologically acceptable salt thereof.

(15) A prophylactic agent and/or therapeutic agent for rheumatoid arthritis, comprising as the active ingredient the compound of any of the above (1) to (12) or a pharmacologically acceptable salt thereof, or a solvate thereof.

Effect of the Invention

The amidopyridine derivatives of the present invention may suppress the cytokine production of T cells and may become a medicament which is effective for the prophylaxis or treatment of diseases involved in the cytokine production from T cells.

The amidopyridine derivatives of the present invention may avoid toxicities represented by hERG inhibitory activity, for example, and may become a medicament which is effective for the prophylaxis and/or treatment of diseases involved in the cytokine production from T cells.

The amidopyridine derivatives of the present invention may avoid hepatocyte toxicity assessed by HepG2 cells, for example, and may become a medicament which is effective for the prophylaxis and/or treatment of diseases involved in the cytokine production from T cells.

DESCRIPTION OF EMBODIMENTS

Herein, "halogen atom" refers to fluorine atom, chlorine atom, bromine atom or iodine atom.

Herein, "alkyl group" refers to a straight- or branched-chain hydrocarbon group having preferably 1 to 10 of carbon atoms, more preferably 1 to 6 of carbon atoms, further preferably 1 to 3 of carbon atoms, and includes, for example, methyl group, ethyl group, normal propyl group, isopropyl group, normal butyl group, isobutyl group, tert-butyl group, normal pentyl group, normal hexyl group, etc.

Herein, "haloalkyl group" refers to a straight- or branched-chain hydrocarbon group having preferably 1 to 6 of carbon atoms, more preferably 1 to 3 of carbon atoms, wherein hydrogen atom is substituted with halogen atom, and includes, for example, fluoromethyl group, difluoromethyl group, trifluoromethyl group, trifluoroethyl group, pentafluoroethyl group, heptafluoroisopropyl group, chloromethyl group, bromomethyl group, etc.

Herein, "alkoxy group" refers to a monovalent group generated by loss of hydrogen atom of hydroxyl group of alcohols, and may be straight- or branched-chain group preferably having 1 to 6 of carbon atoms, more preferably having 1 to 3 carbon atoms, and includes, for example, methoxy group, ethoxy group, normal propoxy group, isopropoxy group, normal butoxy group, isobutoxy group, tert-butoxy group, normal pentyloxy group, normal hexyloxy group, etc.

Herein, "alkoxyalkyl group" refers to a monovalent group wherein the "alkoxy group" defined herein binds to alkyl group via oxygen atom, and the number of carbon atoms of "alkoxyalkyl group" are preferably 2 to 10, more preferably 2 to 6, and each alkyl moiety may be straight- or branched-chain group having preferably 1 to 4 of carbon atoms. For example, it includes methoxymethyl group, ethoxymethyl group, methoxyethyl group, tert-butoxymethyl group, etc.

Herein, "hydroxyalkyl group" refers to a monovalent group wherein hydroxyl group binds to "alkyl group" defined herein, and may be straight- or branched-chain group having preferably 1 to 6 of carbon atoms, more preferably 1 to 3 of carbon atoms, and includes, for example, hydroxymethyl group, hydroxyethyl group, hydroxypropyl group, etc.

Herein, "cycloalkyl group" refers to an alicyclic hydrocarbon ring wherein all of hydrocarbons are saturated, and includes monocyclic hydrocarbon ring, condensed polycyclic hydrocarbon ring, and bridged hydrocarbon ring. The number of carbon atoms generally prefers to 3 to 11, more preferably 3 to 8, further preferably 3 to 6, but is not limited thereto. The carbon atoms on the cycloalkyl group may be partially substituted by oxo group or thioxo group. The cycloalkyl group includes cyclopropyl group, cyclobutyl group, cyclopentyl group, cyclohexyl group, cycloheptyl group, cyclooctyl group, perhydronaphthyl group, adamantyl group, etc.

Herein, "aryl group" refers to a monovalent group of monocyclic aromatic hydrocarbon ring or polycyclic aromatic hydrocarbon ring, and includes, for example, phenyl group, biphenyl group, naphthyl group, anthracenyl group, phenanthryl group, indenyl group, fluorenyl group, azulenyl group, etc. Herein, "aryl group" also refers to a monovalent group of partially saturated aromatic hydrocarbon ring, and includes, for example, 1,2,3,4-tetrahydronaphthyl group, indanyl group, etc.

Herein, "heteroaryl group" refers to a monovalent group of aromatic cyclic compound having at least one heteroatom (e.g. nitrogen, oxygen or sulfur) and carbon atom(s), and includes a monovalent group of 5 to 6-membered monocyclic compound, or 8 to 12-membered condensed cyclic compound condensed or fused with other heterocycle, heteroaryl, cycloalkyl or aryl. In case that a cyclic compound forming heteroaryl group is a condensed cyclic compound, it includes a partially saturated cyclic compound.

The heteroaryl group includes thienyl group, pyrrolyl group, isoxazolyl group, isothiazolyl group, pyrazolyl group, oxazolyl group, oxadiazolyl group, thiazolyl group, thiadiazolyl group, imidazolyl group, triazolyl group, tetrazolyl group, furyl group, triazinyl group, pyrimidinyl group, pyridyl group, benzisooxazolyl group, benzoxazolyl group, benzothiazolyl group, benzisothiazolyl group, benzofuranyl group, dihydrobenzofuranyl group, indolinyl group, isoindolinyl group, pyridazinyl group, indazolyl group, isoindolyl group, indolyl group, indolizinyl group, benzothiophenyl group, dihydrobenzothiophenyl group, benzimidazolyl group, benzotriazolyl group, quinolyl group, quinolizinyl group, phthalazinyl group, naphthyridinyl group, quinoxalinyl group, quinaquizolinyl group, cinnolinyl group, carbazolyl group, dihydrobenzimidazolyl group, indazolyl group, benzisoxazolyl group, benzisothiazolyl group, benzoxazolyl group, benzothiazolyl group, quinazolyl group, isoquinolyl group, quinoxalyl group, pyrrolopyrimidinyl group, pyrrolopyridyl group, imidazopyridyl group, imidazopyrimidyl group, etc.

Herein, "heterocycle group" includes a monovalent group of saturated or partially unsaturated 3 to 6-membered monocyclic compound having at least one heteroatom (e.g., nitrogen, oxygen or sulfur) and carbon atom(s), or 8 to 12-membered condensed cyclic compound condensed or fused with other heterocycle, heteroaryl, cycloalkyl or aryl. The carbon atom(s) or heteroatom(s) on the heterocycle group herein may be partially substituted by oxo group or thioxo group. The heterocycle group includes pyrrolidinyl group, imidazolinyl group, oxazolinyl group, imidazolidinyl group, oxazolidinyl group, pyrazolidinyl group, piperidyl group, piperazyl group, morpholino group, morpholinyl group, dihydrofuryl group, tetrahydrofuryl group, dihydropyryl group, tetrahydropyranyl group, oxetanyl group, oxylanyl group, aziridinyl group, dihydropyrrolyl group, 1,3-dioxolanyl group, 2-oxopyrrolidinyl group, indenyl group, tetrahydroquinolyl group, etc.

n is preferably an integer of 1 to 2, more preferably an integer of 1.

i is preferably an integer of 1 to 2, more preferably an integer of 1.

A substituent group of a five-membered ring in the general formula (I):

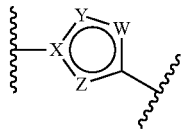

[Chemical formula 7]

is preferably any one of the following groups.

[Chemical formula 8]

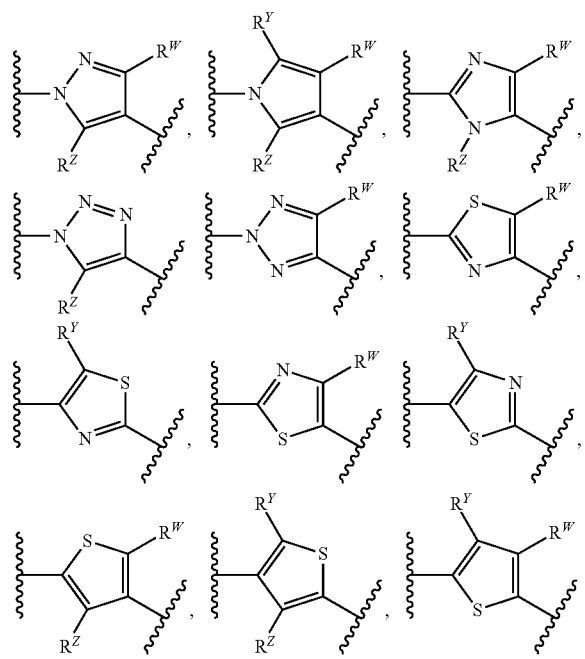

A substituent group of a five-membered ring in the general formula (I):

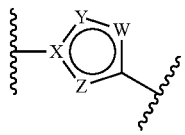

[Chemical formula 9]

is more preferably any group of the following general formulae.

[Chemical formula 10]

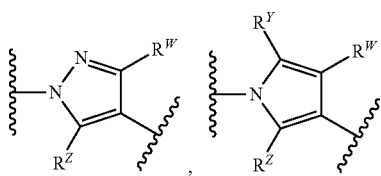

$R^Y$, $R^Z$ and $R^W$ are preferably hydrogen atom, or $C_1$-$C_6$ alkyl group, more preferably hydrogen atom, or $C_1$-$C_3$ alkyl group.

Het is preferably aryl group or heteroaryl group, more preferably phenyl group or pyridyl group.

In the general formula (I) or (I)a, a substituent group of the following formula:

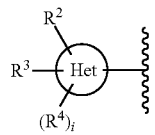

[Chemical formula 11]

is more preferably any group of the following general formulae.

[Chemical formula 12]

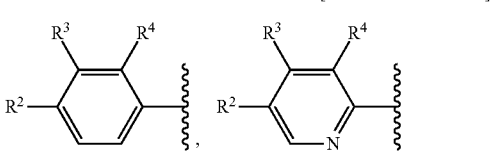

In the general formula (I), a substituent group of the following formula:

[Chemical formula 13]

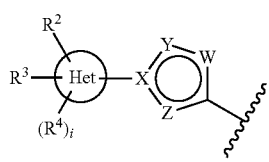

is preferably any group of the following general formulae.

[Chemical formula 14]

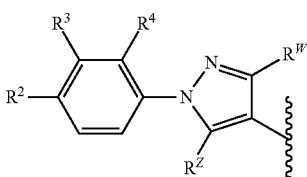

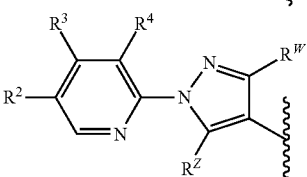

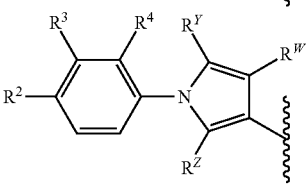

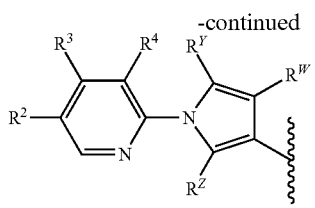

In the general formula (I), a substituent group of the following formula:

[Chemical formula 15]

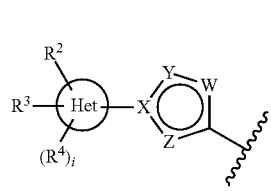

is more preferably any group of the following general formulae.

[Chemical formula 16]

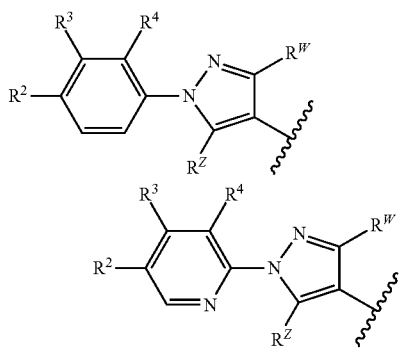

In the general formula (I)a, a substituent group of the following formula:

[Chemical formula 17]

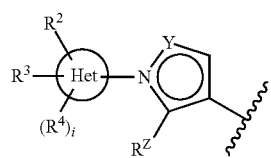

is preferably any group of the following general formulae.

[Chemical formula 18]

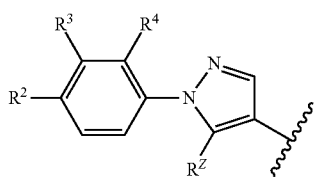

In the general formula (I)a, a substituent group of the following formula:

[Chemical formula 19]

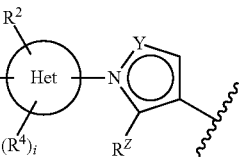

is more preferably any group of the following general formulae.

[Chemical formula 20]

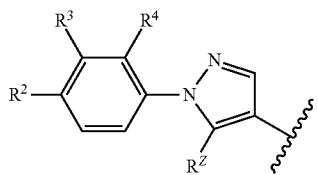

$R^2$ is preferably hydrogen atom, halogen atom, cyano group, hydroxy group, $C_1$-$C_6$ alkyl group, $C_1$-$C_6$ haloalkyl group, $C_1$-$C_6$ alkoxy group, or $C_3$-$C_6$ cycloalkyl group, more preferably hydrogen atom, halogen atom, cyano group, hydroxy group, $C_1$-$C_6$ alkyl group, $C_1$-$C_3$ haloalkyl group, $C_1$-$C_3$ alkoxy group, or $C_3$-$C_6$ cycloalkyl group.

$R^3$ and $R^4$ are preferably hydrogen atom, halogen atom, cyano group, hydroxy group, $C_1$-$C_6$ alkyl group, $C_1$-$C_6$ haloalkyl group, $C_1$-$C_6$ alkoxy group, or $C_3$-$C_6$ cycloalkyl group, more preferably hydrogen atom, halogen atom, cyano group, hydroxy group, $C_1$-$C_6$ alkyl group, $C_1$-$C_3$ haloalkyl group, $C_1$-$C_3$ alkoxy group, or $C_3$-$C_6$ cycloalkyl group, more preferably hydrogen atom, halogen atom.

$R^5$ and $R^6$ are preferably hydrogen atom, hydroxy group, cyano group, optionally substituted $C_1$-$C_6$ alkyl group, optionally substituted $C_1$-$C_6$ alkoxy group, optionally substituted $C_3$-$C_6$ cycloalkyl group, -L-$NR^{7a}R^{7b}$, -L-$NR^{7a}$—CO—$R^{7b}$, -L-CO—$NR^{7a}R^{7b}$, or -L-O—CO—$R^{7c}$ (wherein $R^{7a}$, $R^{7b}$, and $R^{7c}$ have the same meanings as defined above), or $R^5$ and $R^6$ are optionally combined with each other to form optionally substituted $C_3$-$C_6$ cycloalkyl group, or optionally substituted heterocycle group.

A substituent of "optionally substituted alkyl group" of $R^5$ and $R^6$ includes hydroxy group, halogen atom, amino group, alkylamino group, cyano group, $C_1$-$C_6$ alkoxy group, $C_3$-$C_6$ cycloalkyl group, etc. Preferable one is hydroxy group, halogen atom, $C_1$-$C_3$ alkoxy group.

A substituent of "optionally substituted alkoxy group" of $R^5$ and $R^6$ includes hydroxy group, halogen atom, cyano group, amino group, alkylamino group, etc., and preferable one is hydroxy group, halogen atom.

A substituent of "optionally substituted cycloalkyl group" of $R_5$ and $R^6$ includes hydroxy group, halogen atom, $C_1$-$C_6$ alkyl group, $C_1$-$C_6$ alkoxy group, $C_1$-$C_6$ haloalkyl group, $C_1$-$C_6$ alkoxyalkyl group, amino group, $C_1$-$C_6$ alkylamino group, $C_2$-$C_6$ alkylcarbonyl group, etc., and preferable one is halogen atom, hydroxy group, $C_1$-$C_6$ alkyl group.

A substituent of "optionally substituted cycloalkyl group", or "optionally substituted heterocycle group" which $R^5$ and $R^6$ are optionally combined with each other to form includes hydroxy group, halogen atom, $C_1$-$C_6$ alkyl group, $C_1$-$C_6$ alkoxy group, $C_1$-$C_6$ haloalkyl group, $C_1$-$C_6$ alkoxyalkyl group, amino group, $C_1$-$C_6$ alkylamino group, $C_2$-$C_6$ alkylcarbonyl group, etc.

$R^{7a}$ and $R^{7b}$ are preferably hydrogen atom or $C_1$-$C_6$ alkyl group, more preferably hydrogen atom or $C_1$-$C_3$ alkyl group.

$R^{7c}$ is preferably $C_1$-$C_6$ alkyl group or phenyl group.

D is preferably any group of the following general formulae.

[Chemical formula 21]

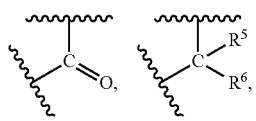

D is more preferably a group of the following general formula.

[Chemical formula 22]

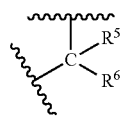

L is preferably a bond or $C_1$-$C_6$ alkylene group, more preferably a bond or $C_1$-$C_3$ alkylene group.

A compound of the general formula (I) or the general formula (I)a or a salt thereof may be synthesized by applying various known synthetic methods with utilizing characteristics based on the basic skeleton or the type of substituent groups. Preparation methods of amidopyridine derivatives of the general formula (I) are illustrated as below, but are not limited thereto.

Depending on the type of functional groups, it may be effective in view of the processing technology that said functional groups may be preliminarily converted at the stage of starting materials or intermediate compounds into appropriate protecting groups, i.e. groups which may be easily reconverted into said functional groups, and the protecting groups may be optionally deprotected to give the desired compounds.

Among compounds of the general formula (I), a compound group wherein X is N, Z is N—$R^Z$ and W is CH is represented by the general formula (I)a, and a compound of the present invention of the general formula (I)a may be also prepared according to the following methods.

[Preparation Method] Synthtic Method of Amidopyridine Derivatives of the Present Invention Method 1: The compound (1) of the present invention may be prepared according to the following method.

[Chemical formula 23]

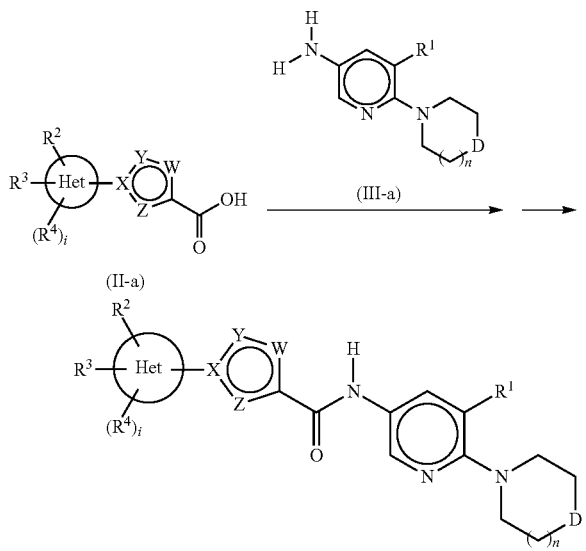

(In the formula, each symbol has the same meaning as defined above.)

The condensation reaction of Compound (II-a) and Compound (III-a) may be carried out by either method selected from the following three processes.

(1) Compound (II-a) is treated by the conventional method using a halogenating agent and converted into the corresponding acid halide, followed by reacting with Compound (III-a) to give the corresponding compound of the general formula (I). The reaction proceeds in an appropriate solvent usually in the range from −20° C. to reflux temperature of the solvent using a base. The reaction time varies depending on starting materials or solvents to be used and reaction temperature, etc., and is usually in the range from 30 minutes to 24 hours. The halogenating agent includes, for example, thionyl chloride, oxalyl chloride, etc. The base includes, for example, triethylamine, pyridine, etc. The solvent includes, for example, dichloromethane, dichloroethane, chloroform. N-methylpyrrolidone, pyridine, toluene, etc. In this reaction, a base to be used may be also used as a solvent.

(2) Compound (II-a) is condensed with Compound (III-a) in the presence of a condensing agent to give the corresponding compound of the general formula (I). The reaction temperature is usually in the range from 0° C. to 100° C. The reaction time varies depending on starting materials or solvents to be used and reaction temperature, etc., and is usually in the range from 30 minutes to 24 hours. The condensing agent includes 1,3-dicyclohexylcarbodiimide, 1-ethyl-3-(3-dimethylaminopropyl)carbodiimide hydrochloride, carbonyldiimidazole, 4-(4,6-dimethoxy[1,3,5]triazin-2-yl)-4-methylmorpholinium chloride hydrate (DMT-MM)), etc. The solvent includes N,N-dimethylformamide, dimethyl sulfoxide, tetrahydrofuran, dichloromethane, chloroform, 1,4-dioxane, methanol, ethanol, isopropyl alcohol, butanol, etc. The reaction may be accelerated by the addition of 1-hydroxybenzotriazole (HOBt). In case that Compound (III-a) forms a salt with an acid, the reaction proceeds by neutralization by the addition of a base. Alternatively, the condensing agent of the reaction includes, for example, diethyl cyanophosphonate, diphenylphosphoryl azide, etc. The reaction proceeds in an appropriate solvent such as N,N-dimethylformamide, dimethyl sulfoxide in the presence of a base (e.g., triethylamine, pyridine, etc.). The reaction temperature is usually in the range from 0° C. to 100° C. The reaction time varies depending on starting materials or solvents to be used and reaction temperature, etc., and is usually in the range from 30 minutes to 24 hours.

(3) Compound (II-a) is converted into a mixed acid anhydride formed with a reagent such as methyl chlorocarbonate, ethyl chlorocarbonate, isobutyloxycarbonyl chloride, pivaloyl chloride, followed by reacting with Compound (III-a) in a solvent in the presence of a base or in a base as a solvent to give a compound of the general formula (I). The solvent includes, for example, methanol, ethanol, isopropyl alcohol, butanol, ethylene glycol, tetrahydrofuran, chloroform, N,N-dimethylformamide, toluene, etc. The base includes, for example, triethylamine, pyridine, N-methylmorpholine, etc. The reaction temperature is usually in the range from 0° C. to 100° C. The reaction time varies depending on starting materials or solvents to be used and reaction temperature, etc., and is usually in the range from 30 minutes to 24 hours.

Method 2: Compound (I) may be synthesized according to the following method using amide compound (II-b) and Compound (III-b).

[Chemical formula 24]

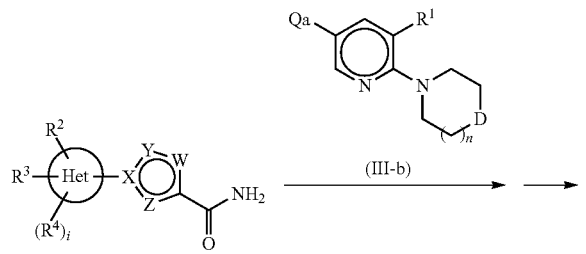

(In the formula, Qa is a chlorine atom, bromine atom, iodine atom, trifluoromethanesulfonyloxy group or p-toluenesulfonyloxy group, and the other symbols have the same meanings as defined above.)

Compound (II-b) which is obtained by treating Compound (II-a) according to Method 1-(1) to convert into an acid halide, followed by treating with aqueous ammonia is reacted with Compound (III-b) in an appropriate solvent under nitrogen atmosphere in the presence of a base, a copper catalyst and a ligand to give the corresponding compound of the general formula (I). The solvent used in the reaction includes, for example, N,N-dimethylformamide, dimethyl sulfoxide, 1,4-dioxane, N-methylpyrrolidone, toluene, tetrahydrofuran, cyclopentyl methyl ether, xylene, 1,2-dimethoxyethane, tert-butanol, etc. The base includes, for example, potassium carbonate, cesium carbonate, potassium acetate, tripotassium phosphate, diisopropylethylamine, sodium tert-butoxide, etc. The copper catalyst includes copper (I) iodide, copper (I) bromide, etc. The ligand includes N,N'-dimethylethylenediamine, trans-N,N'-dimethylcyclohexanediamine, trans-1,2-cyclohexanediamine 1,10-phenanthroline, etc.

The reaction also proceeds in an appropriate solvent under nitrogen atmosphere using a palladium catalyst, a ligand and a base with heating. The solvent used in the reaction includes, for example, N,N-dimethylformamide, dimethyl sulfoxide, 1,4-dioxane, N-methylpyrrolidone, toluene, tetrahydrofuran, cyclopentyl methyl ether, xylene, 1,2-dimethoxyethane, tert-butanol, etc. The base includes, for example, potassium carbonate, cesium carbonate, potassium acetate, tripotassium phosphate, diisopropylethylamine, sodium tert-butoxide, etc. The palladium catalyst includes, for example, palladium (II) acetate, tris(dibenzylideneacetone)dipalladium (0), etc. The ligand includes a phosphine ligand such as 4,5-bis(diphenylphosphino)-9,9-dimethylxanthene, 2-dicyclohexylphosphinobiphenyl, 2-di-tert-butylphosphinobiphenyl, 2-(di-tert-butylphosphino)-3,4,5,6-tetramethyl-2',4',6'-triisopropyl-1,1'-biphenyl, 2-(dicyclohexylphosphino)-2',4',6'-triisopropyl-1,1'-biphenyl, etc.

The reaction temperature is usually in the range from room temperature to reflux temperature of solvent. The reaction time varies depending on starting materials or solvents to be used and reaction temperature, etc., and is usually in the range from 1 hour to 72 hours.

Method 3: Compound (I) may be synthesized according to the following method using Compound (II-c) and Compound (IV-a).

[Chemical formula 25]

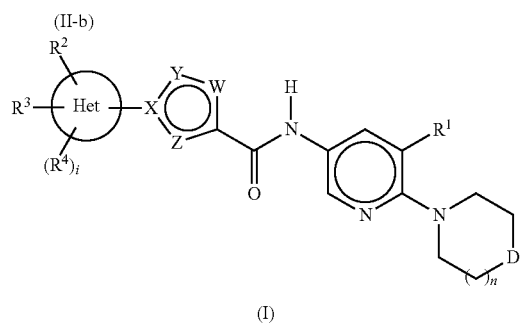

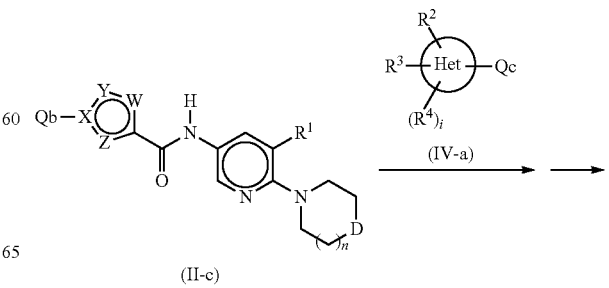

-continued

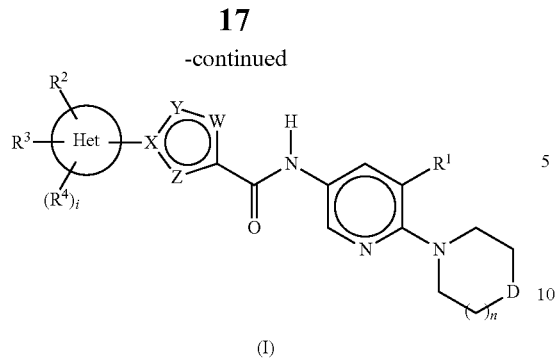

(I)

(In the formula, Qb is a bromine atom, chlorine atom, iodine atom, trifluoromethanesulfonyloxy group or p-toluenesulfonyloxy group, Qc is an active group containing a boron atom such as boron acid, boron acid ester, for example. The other symbols have the same meanings as defined above.)

Compound (II-c) is coupled with Compound (IV-a) under Suzuki reaction conditions to give the corresponding compound of the general formula (I). The reaction proceeds under nitrogen atmosphere using a palladium catalyst, a ligand and a base in an appropriate solvent with heating. The solvent used in the reaction includes, for example, tetrahydrofuran, toluene, acetonitrile, N-methylpyrrolidone, N,N-dimethylformamide, dimethyl sulfoxide, 1,4-dioxane, 1,2-dimethoxyethane, tert-butanol, isopropanol, ethanol, methanol or a mixed solvent of the organic solvent with water, etc. The base includes, for example, potassium carbonate, cesium carbonate, sodium carbonate, potassium acetate, tripotassium phosphate, diisopropylethylamine, sodium tert-butoxide, etc. The palladium catalyst includes, for example, palladium (II) acetate, tris(dibenzylideneacetone)dipalladium (0), etc. The ligand includes a phosphine ligand such as 2-dicyclohexylphosphino-2,6-dimethoxybiphenyl, 2-dicyclohexylphosphinobiphenyl, 2-(di-tert-butylphosphino)biphenyl, 2-(di-tert-butylphosphino)-3,4,5,6-tetramethyl-2',4',6'-triisopropyl-1,1'-biphenyl, 2-(dicyclohexylphosphino)-2',4',6'-triisopropyl-1,1'-biphenyl, 4,5-bis(diphenylphosphino)-9,9-dimethylxanthene, etc. A complex formed by a palladium catalyst and a phosphine ligand may be used, and for example, includes [1,1'-bis(diphenylphosphino)ferrocene]palladium (II) dichloride-dichloromethane complex, dichlorobis(tricyclohexylphosphine)palladium (II), tetrakis(triphenylphosphine)palladium (0), [1,1'-bis(diphenylphosphino)ferrocene]palladium (II) dichloride, dichlorobis(tricyclohexylphosphine)palladium (II), bis(triphenylphosphine)-palladium (II) dichloride, etc. The reaction temperature is usually in the range from room temperature to reflux temperature of solvent. The reaction time varies depending on starting materials or solvents to be used and reaction temperature, etc., and is usually in the range from 1 hour to 24 hours.

Method 4: Compound (I) wherein X is a nitrogen atom may be synthesized according to the following method using Compound (II-d) and Compound (IV-b).

[Chemical formula 26]

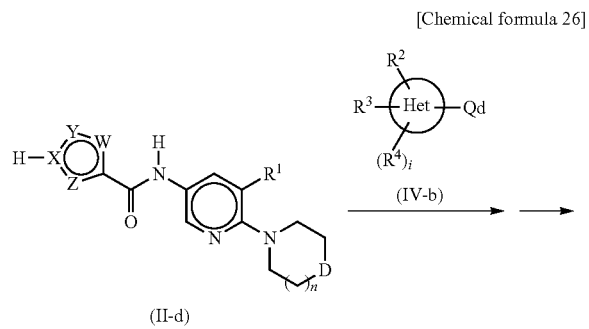

-continued

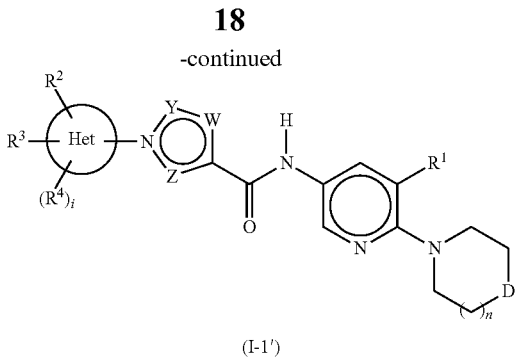

(I-1')

(In the formula, Qd is a fluorine atom, bromine atom, chlorine atom, iodine atom, trifluoromethanesulfonyloxy group, boric acid or boric acid ester. The other symbols have the same meanings as defined above.)

(1) In case that Qd is a bromine atom, chlorine atom or iodine atom, Compound (II-d) is reacted with Compound (IV-b) under nitrogen atmosphere in the presence of a base, a copper catalyst and a ligand to give the corresponding compound of the general formula (I). The solvent used in the reaction includes, for example, N,N-dimethylformamide, dimethyl sulfoxide, 1,4-dioxane, N-methylpyrrolidone, toluene, tetrahydrofuran, cyclopentyl methyl ether, xylene, 1,2-dimethoxyethane, tert-butanol, etc. The base includes, for example, potassium carbonate, cesium carbonate, potassium acetate, tripotassium phosphate, diisopropylethylamine, sodium tert-butoxide, etc. The copper catalyst includes, for example, copper (I) iodide, copper (I) bromide, etc. The ligand includes N,N'-dimethylethylenediamine, trans-N,N'-dimethylcyclohexanediamine, trans-1,2-cyclohexanediamine, 1,10-phenanthroline, etc.

(2) In case that Qd is trifluoromethanesulfonyloxy group, Compound (II-d) is reacted with Compound (IV-b) under nitrogen atmosphere in an appropriate solvent in the presence of a base, a palladium catalyst and a ligand to give the corresponding compound of the general formula (I). The solvent used in the reaction includes, for example, toluene, 1,4-dioxane, tetrahydrofuran, N,N-dimethylformamide and a mixed solvent thereof, etc. The base includes, for example, potassium carbonate, cesium carbonate, tripotassium phosphate, etc. The palladium catalyst includes, for example, tris(dibenzylideneacetone)dipalladium (0), etc. The ligand includes 2,2'-bis(dicyclohexylphosphino)-1,1'-binaphthyl, 2-(dicyclohexylphosphino)-2',4',6'-triisopropyl-1,1'-biphenyl, etc.

(3) In case that Qd is boric acid or boric acid ester, Compound (II-d) is reacted with Compound (IV-b) under nitrogen atmosphere in an appropriate solvent in the presence of a base, a palladium catalyst and a ligand to give the corresponding compound of the general formula (I). The solvent used in the reaction includes, for example, N,N-dimethylformamide, dimethyl sulfoxide, 1,4-dioxane, N-methylpyrrolidone, toluene, tetrahydrofuran, cyclopentyl methyl ether, xylene, 1,2-dimethoxyethane, tert-butanol, etc. The base includes, for example, potassium carbonate, cesium carbonate, potassium acetate, tripotassium phosphate, diisopropylethylamine, sodium tert-butoxide, potassium tert-butoxide, etc. The palladium catalyst includes, for example, palladium (II) acetate, tris(dibenzylideneacetone) dipalladium (0), etc. The ligand includes a phosphine ligand such as 4,5-bis(diphenylphosphino)-9,9-dimethylxanthene, 2-dicyclohexylphosphinobiphenyl, 2-di-tert-butylphosphinobiphenyl, 2-(di-tert-butylphosphino)-3,4,5,6-tetramethyl-2',4',6'-triisopropyl-1,1'-biphenyl, 2-(dicyclohexylphosphino)-2',4',6'-triisopropyl-1,1'-biphenyl, etc. A complex formed by a palladium catalyst and a phosphine ligand may be used, and includes, for example [1,1'-bis(diphenylphosphino)ferrocene]palladium (II) dichloride-dichloromethane complex, dichlorobis(tricyclohexylphosphine)palladium (II), tetrakis(triphenylphosphine)palladium (0), [1,1'-bis(diphenylphosphino)ferrocene]palladium (II) dichloride, dichlorobis-(tricyclohexylphosphine)palladium (II), bis(triphenylphosphine)palladium (II) dichloride, etc.

The reaction temperature is usually in the range from room temperature to reflux temperature of solvent. The reaction time varies depending on starting materials or solvents to be used and reaction temperature, etc., and is usually in the range from 1 hour to 72 hours.

Method 5: Compound (II-a-1) wherein X is a nitrogen atom, Y, Z and W are carbon atoms, $R^Y$, $R^Z$ and $R^W$ are hydrogens and pyrrole is substituted by a carboxyl group on the 3-position among Compound (II-a) may be synthesized according to the following methods.

[Chemical formula 27]

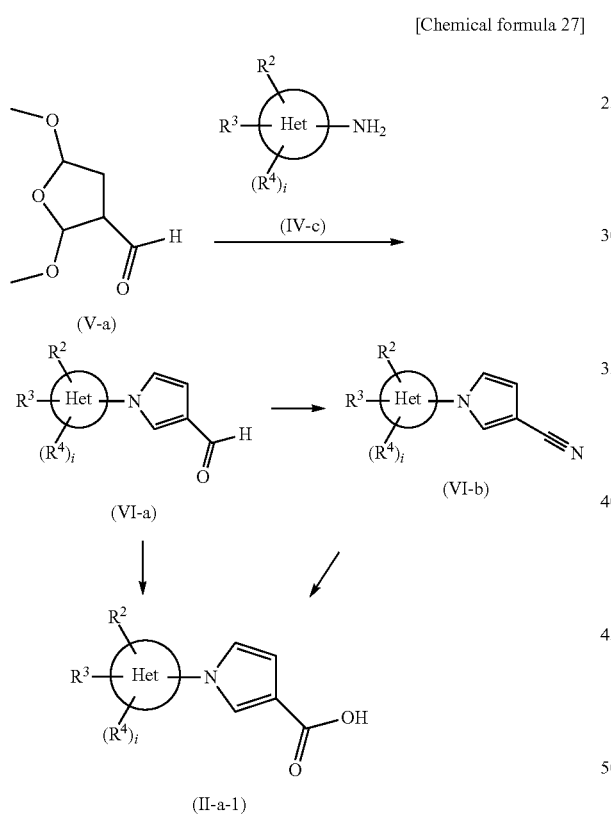

(In the formula, each symbol has the same meaning as defined above.)

(1) Compound (V-a) is reacted with Compound (IV-c) in an appropriate solvent (e.g., acetic acid, water, methanol or a mixed solvent thereof) in the range from room temperature to reflux temperature of solvent for 1 to 24 hours to give Compound (VI-a). Compound (VI-a) is oxidized in the presence of a base (including sodium hydroxide, potassium hydroxide, triethylamine, pyridine) by an oxidizing agent (including manganese dioxide, potassium permanganate, peroxides (including hydrogen peroxide, meta-chloroperoxybenzoic acid)) to give Compound (II-a-1).

(2) Compound (II-a-1) is also obtained according to the following method. Compound (VI-a) is treated by hydroxylamine hydrochloride in an appropriate solvent (e.g., water, methanol, ethanol, acetonitrile, tetrahydrofuran or a mixed solvent thereof) in the presence of a base (including sodium acetate, sodium hydroxide, sodium hydrogen carbonate, potassium carbonate, triethylamine), followed by treatment by an acid anhydride (including acetic anhydride, phthalic acid anhydride) to give Compound (VI-b), and then reacted with a base (including sodium hydroxide, potassium hydroxide) in an appropriate solvent (e.g., ethanol, water, tetrahydrofuran or a mixed solvent thereof) at a reflux temperature of solvent to give Compound (II-a-1).

Method 6: Compound (II-a-1) may be also synthesized according to the following method.

[Chemical formula 28]

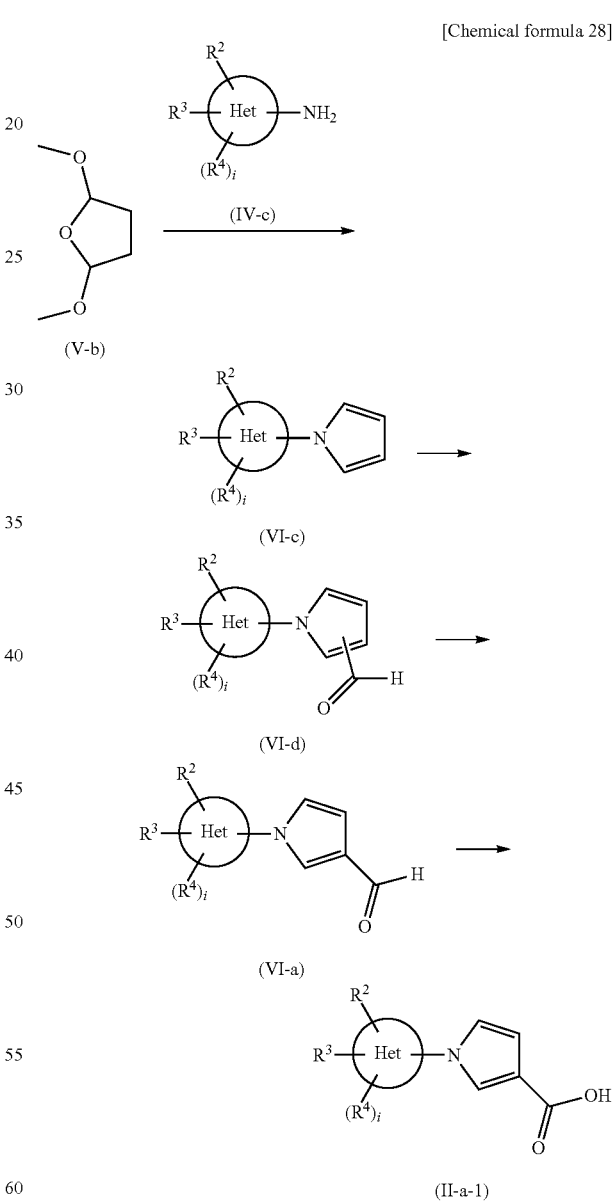

(In the formula, each symbol has the same meaning as defined above.)

Compound (V-b) is reacted with Compound (IV-c) in an appropriate solvent (e.g., acetic acid, water, methanol or a mixed solvent thereof) in the range from room temperature to reflux temperature of solvent for 1 to 24 hours to give Compound (VI-c). Compound (VI-c) is treated with phosphorus oxychloride in the presence of N,N-dimethylformamide or N-methylformanilide in the range from room temperature to 100° C. for 1 to 24 hours to give Compound (VI-d) (Vilsmeier reaction). Compound (VI-d) may be reacted with trifluoromethanesulfonic acid in an appropriate solvent (including methylene chloride, chloroform, dichloroethane, benzene, toluene, xylene) in the range from room temperature to reflux temperature of solvent for 1 to 24 hours to give Compound (VI-a). Compound (VI-a) is oxidized by an oxidizing agent (including manganese dioxide, potassium permanganate, peroxides (including hydrogen peroxide, meta-chloroperbenzoic acid)) in the presence of a base (including sodium hydroxide, potassium hydroxide, triethylamine, pyridine) to give Compound (II-a-1).

Method 7: Compound (II-a-2) wherein X is a nitrogen atom, Y, Z and W are carbons and the 3-position is substituted by a carboxyl group among Compound (II-a) may be synthesized according to the following method.

Method 8: Compound (II-a-3) wherein X is a nitrogen atom and pyrrole is substituted with a carboxyl group at the 3-position among Compound (II-a) may be also synthesized according to the following method.

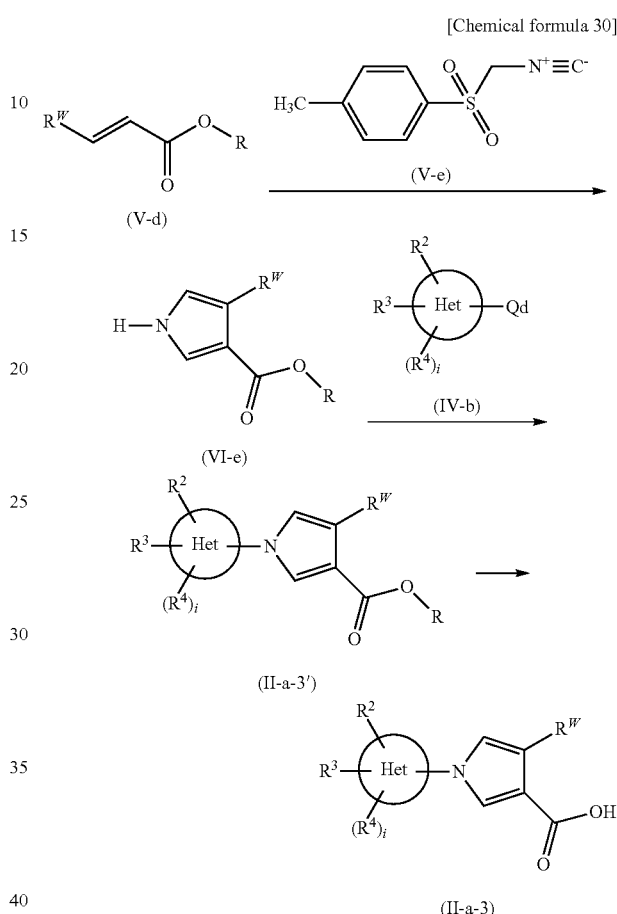

[Chemical formula 29]

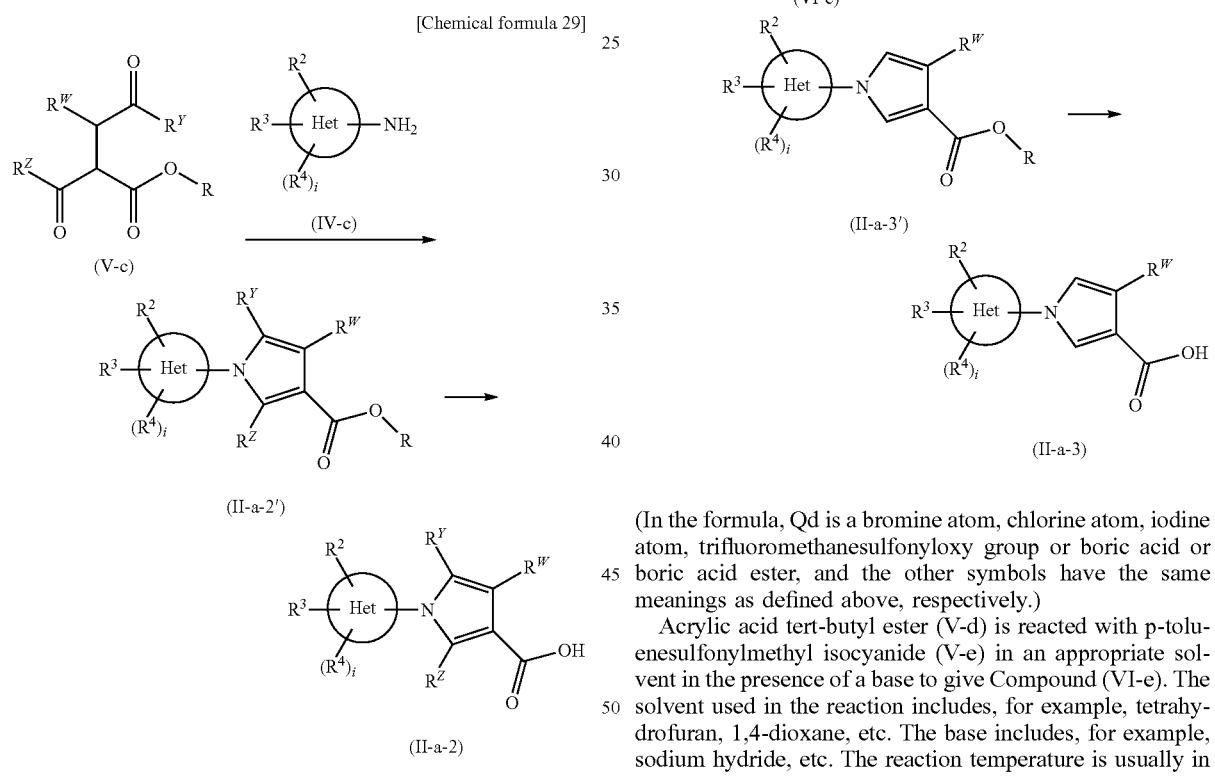

(In the formula, R is alkyl (e.g., methyl, ethyl, tert-butyl). Each symbol has the same meaning as defined above.)

Compound (V-c) may be reacted with Compound (IV-c) in an appropriate solvent (e.g., methanol, ethanol, water or a mixed solvent thereof) in the presence or absence of an acid (including hydrochloric acid, sulfuric acid, nitric acid, acetic acid) in the range from room temperature to 100° C. for 1 to 24 hours to give Compound (II-a-2'), followed by hydrolysis according to the conventional method to give Compound (II-a-2).

(In the formula, Qd is a bromine atom, chlorine atom, iodine atom, trifluoromethanesulfonyloxy group or boric acid or boric acid ester, and the other symbols have the same meanings as defined above, respectively.)

Acrylic acid tert-butyl ester (V-d) is reacted with p-toluenesulfonylmethyl isocyanide (V-e) in an appropriate solvent in the presence of a base to give Compound (VI-e). The solvent used in the reaction includes, for example, tetrahydrofuran, 1,4-dioxane, etc. The base includes, for example, sodium hydride, etc. The reaction temperature is usually in the range from room temperature to 80° C. The reaction time varies depending on starting materials or solvents to be used and reaction temperature, etc., and is usually in the range from 30 minutes to 12 hours.

The second step is a step wherein Compound (VI-e) is reacted with Compound (IV-b) to give Compound (II-a-3').

(1) In case that Qd is a bromine atom, chlorine atom or iodine atom, Compound (VI-e) is reacted with Compound (IV-b) under nitrogen atmosphere in the presence of a base, a copper catalyst and a ligand to give the corresponding Compound (II-a-3'). This reaction proceeds in a similar manner to that of Method 4-(1).

(2) In case that Qd is trifluoromethanesulfonyloxy group. Compound (VI-e) is reacted with Compound (IV-b) under nitrogen atmosphere in an appropriate solvent in the presence of a base, a palladium catalyst and a ligand to give the corresponding Compound (II-a-3'). This reaction proceeds in a similar manner to that of Method 4-(2).

(3) In case that Qd is boric acid or boric acid ester, Compound (VI-e) is reacted with Compound (IV-b) under nitrogen atmosphere in an appropriate solvent in the presence of a base, a palladium catalyst and a ligand to give the corresponding Compound (II-a-3'). This reaction proceeds in a similar manner to that of Method 4-(3).

The obtained Compound (II-a-3') may be hydrolyzed according to the conventional method to give Compound (II-a-3).

Method 9: Compound (II-a-4) wherein X is a nitrogen atom among Compound (II-a) may be synthesized according to the following method.

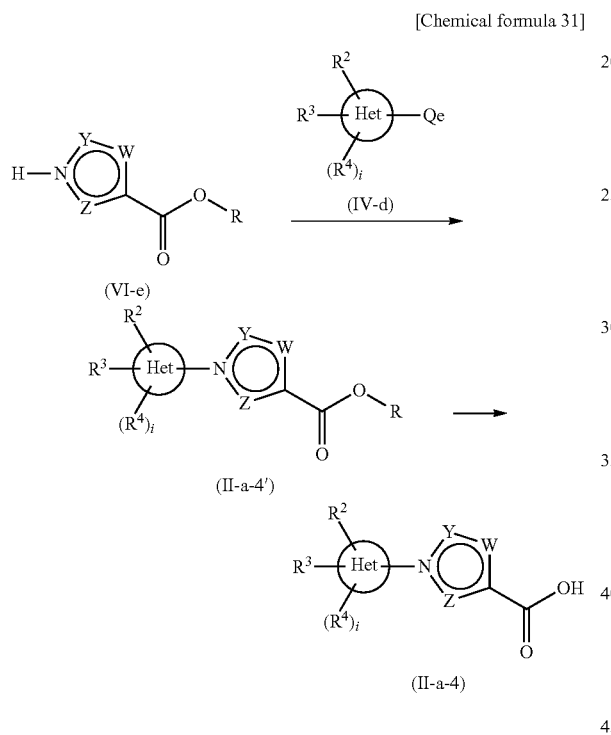

(In the formula, Qe is a fluorine atom, chlorine atom, bromine atom, iodine atom, trifluoromethanesulfonyloxy group or boric acid or boric acid ester. The other symbols have the same meanings as defined above, respectively.)

(1) In case that Qe is fluorine atom, chlorine atom or bromine atom, Compound (VI-e) is treated in an appropriate solvent in the presence of a base, followed by reacting with Compound (IV-d) to give Compound (II-a-4'). Then, according to the conventional method, Compound (II-a-4) may be obtained by hydrolysis. The solvent includes, for example, tetrahydrofuran, N,N-dimethylformamide, etc. The base includes, for example, sodium hydride, potassium carbonate, diisopropylethylamine, sodium tert-butoxide, potassium tert-butoxide, etc. The reaction temperature is usually in the range from 0° C. to reflux temperature of solvent, and the reaction time varies depending on starting materials or solvents to be used and reaction temperature, etc., and is usually in the range from 1 to 24 hours.

(2) In case that Qe is a chlorine atom, bromine atom or iodine atom, Compound (VI-e) is reacted with Compound (IV-d) under nitrogen atmosphere in the presence of a base, a copper catalyst and a ligand to give the corresponding Compound (II-a-4'). The reaction proceeds in a similar manner to that of Method 4-(1).

(3) In case that Qe is trifluoromethanesulfonyloxy group, Compound (VI-e) is reacted with Compound (IV-d) under nitrogen atmosphere in an appropriate solvent in the presence of a base, a palladium catalyst and a ligand to give the corresponding Compound (II-a-4'). The reaction proceeds in a similar manner to that of Method 4-(2).

(4) In case that Qe is boric acid or boric acid ester, Compound (VI-e) is reacted with Compound (IV-d) under nitrogen atmosphere in an appropriate solvent in the presence of a base, a palladium catalyst and a ligand to give the corresponding Compound (II-a-4'). The reaction proceeds in a similar manner to that of Method 4-(3).

The obtained Compound (II-a-4') may be hydrolyzed according to the conventional method to give Compound (II-a-4).

Method 10: Compound (II-a) may be obtained by hydrolyzing according to the conventional method Compound (II-a') which is obtained by coupling Compound (VI-t) and Compound (IV-a).

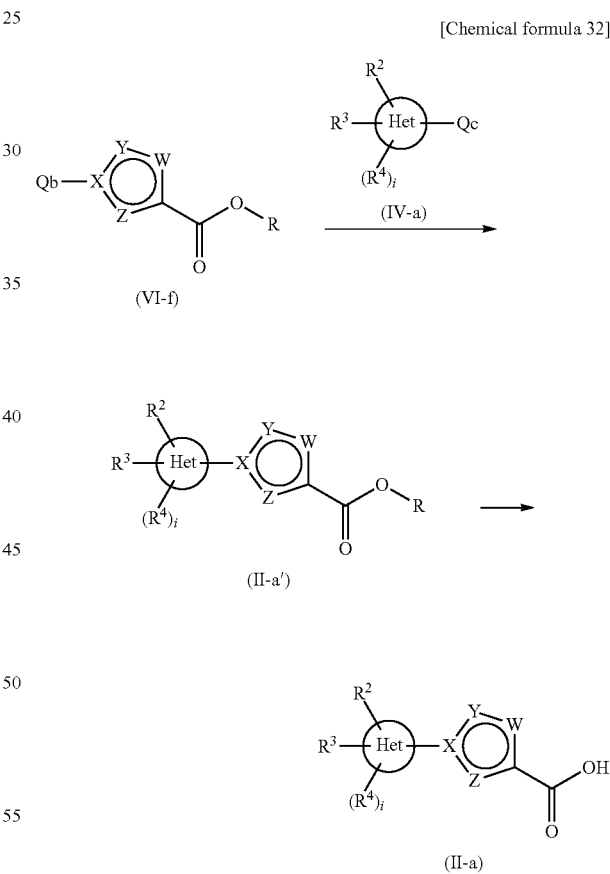

(In the formula, each symbol has the same meaning as defined above.)

Compound (VI-f) is coupled with Compound (IV-a) according to Suzuki reaction to give the corresponding Compound (II-a'). The reaction proceeds in a similar manner to that of Method 3. The obtained Compound (II-a') may be hydrolyzed according to the conventional method to give Compound (II-a).

Method 11: Compound (II-a-5) which is Compound (II-a) wherein X and Y are nitrogen atoms, W and Z are carbon atoms, and the 4-position is substituted by a carboxyl group may be synthesized according to the following method.

[Chemical formula 33]

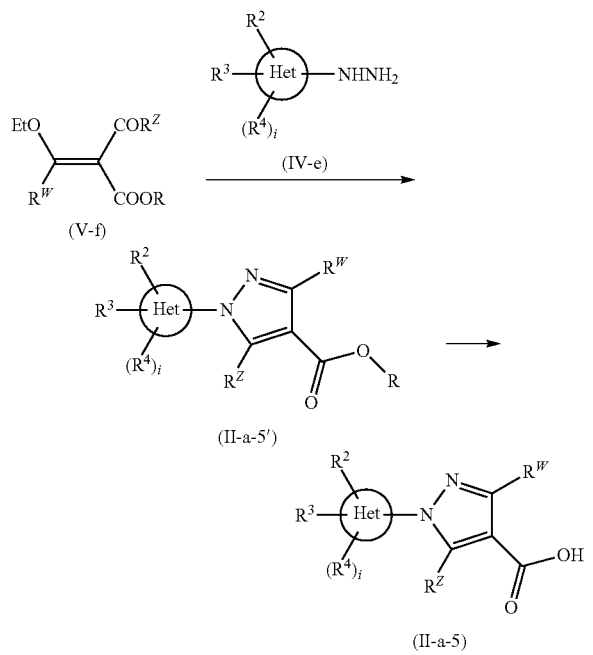

(In the formula, each symbol has the same meaning as defined above.)

Compound (V-f) may be reacted with Compound (IV-e) in an appropriate solvent (such as water, methanol, ethanol, isopropyl alcohol, butanol, ethylene glycol, acetic acid or a mixed solvent thereof) in the range from room temperature to reflux temperature of solvent for 1 to 24 hours to give Compound (II-a-5'). Compound (II-a-4') may be reacted in an appropriate solvent (such as water, methanol, ethanol, tetrahydrofuran or a mixed solvent thereof) using an acid (such as hydrochloric acid, sulfuric acid) or a base (such as sodium hydroxide, potassium hydroxide) in the range from room temperature to reflux temperature of solvent for 1 to 24 hours to give Compound (II-a-5).

Method 12: Compound (II-a-7) which is Compound (II-a) wherein X and Y are nitrogen atoms, W and Z are carbon atoms, and the 4-position of pyrazole is substituted by a carboxyl group may be synthesized according to the following method.

[Chemical formula 34]

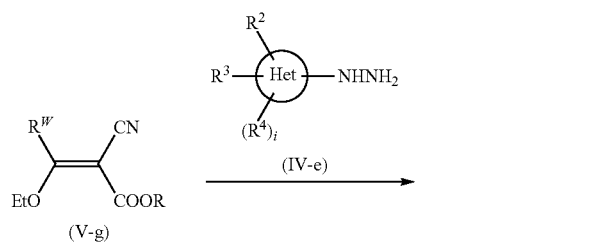

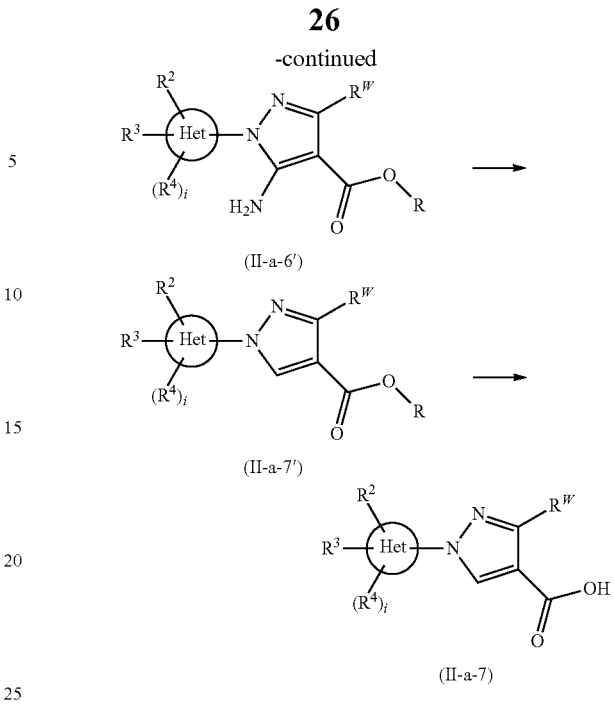

(In the formula, each symbol has the same meaning as defined above.)

Compound (V-g) may be reacted with Compound (IV-e) in an appropriate solvent (such as water, methanol, ethanol, isopropyl alcohol, butanol, ethylene glycol, acetic acid or a mixed solvent thereof) in the range from room temperature to reflux temperature of solvent for 1 to 24 hours to give Compound (II-a-6').

Compound (II-a-6') may be treated in an appropriate solvent (such as water, acetic acid, methanol, ethanol, isopropyl alcohol, butanol, ethylene glycol, tetrahydrofuran or a mixed solvent thereof) in the presence or absence of aqueous hypophosphorous acid solution by addition of isoamyl nitrite, etc., followed by reacting at 0° C. to 5° C. for 1 to 3 hours, then at room temperature for 4 to 12 hours to give Compound (II-a-7'). Compound (II-a-7') may be reacted in an appropriate solvent (such as water, methanol, ethanol, tetrahydrofuran or a mixed solvent thereof) using an acid (such as hydrochloric acid, sulfuric acid) or an alkali (such as sodium hydroxide, potassium hydroxide) in the range from room temperature to reflux temperature of solvent for 1 to 24 hours to give Compound (II-a-7).

Method 13: Compound (II-a-5) which is Compound (II-a) wherein X and Y are nitrogen atoms, W and Z are carbon atoms, and the 4-position is substituted by a carboxyl group may be also prepared according to the following method.

[Chemical formula 35]

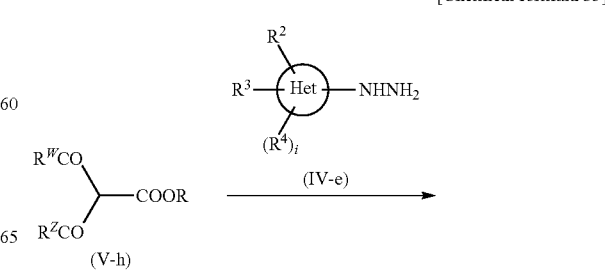

-continued

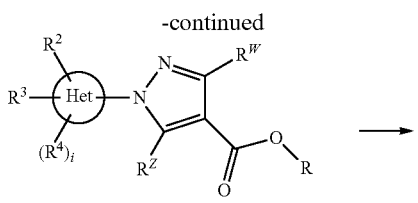

(II-a-8′)

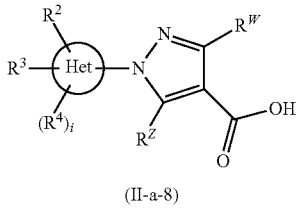

(II-a-8)

(In the formula, each symbol has the same meaning as defined above.)

Compound (V-h) may be reacted with Compound (IV-e) in an appropriate solvent (such as water, methanol, ethanol, isopropyl alcohol, butanol, ethylene glycol, acetic acid or a mixed solvent thereof) in the range from −20° C. to reflux temperature of solvent for 1 to 24 hours to give Compound (II-a-8′). Compound (II-a-8′) may be reacted in an appropriate solvent (such as water, methanol, ethanol, tetrahydrofuran or a mixed solvent thereof) using an acid (such as hydrochloric acid, sulfuric acid) or an alkali (such as sodium hydroxide, potassium hydroxide) in the range from room temperature to reflux temperature of solvent for 1 to 24 hours to give Compound (II-a-8).

Method 14: Compound (III-a) may be synthesized according to the following method.

[Chemical formula 36]

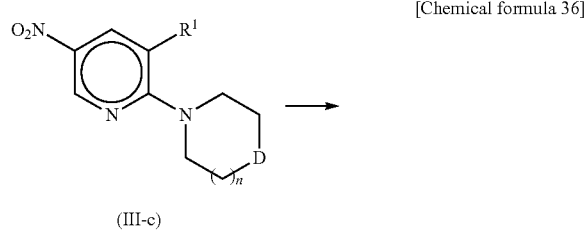

(In the formula, each symbol has the same meaning as defined above.)

Any conventional reduction method in organic synthetic chemistry which may produce Compound (III-a) from Compound (III-c) may be applicable. For example, a treatment with diluted hydrochloric acid or a catalytic amount of ammonium chloride in an appropriate solvent (such as water, methanol, ethanol, propanol, butanol, ethylene glycol, tetrahydrofuran, 1,4-dioxane or a mixed solvent thereof) using iron powder as a catalyst, or a catalytic reduction method wherein a hydrogenation is carried out in the presence of a catalyst such as nickel, palladium, platinum is included. As to the reaction conditions, the reaction temperature is usually in the range from room temperature to reflux temperature of solvent, and the reaction time usually includes in the range from 1 to 24 hours.

Method 15: Compound (III-a) may be also synthesized according to the following method.

[Chemical formula 37]

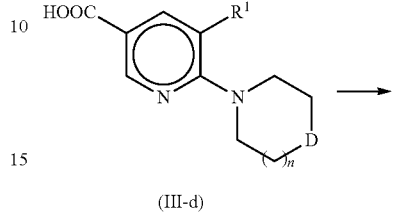

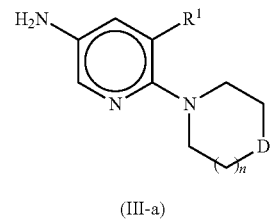

(III-a)

(In the formula, each symbol has the same meaning as defined above.)

Compound (III-d) is treated with sodium azide and strong acid (such as sulfuric acid, trifluoroacetic acid) in an appropriate solvent (water, methanol, ethanol, propanol, butanol, tertiary butyl alcohol, ethylene glycol, benzene, toluene, xylene, preferably benzene) in the range from room temperature to reflux temperature of solvent for 1 to 24 hours by utilizing Curtius rearrangement or Schmidt rearrangement, or reacted with triethylamine and diphenylphosphoryl azide in an appropriate solvent (methanol, ethanol, isopropyl alcohol, butanol, tertiary butanol, preferably tert-butanol) in the range from room temperature to reflux temperature of solvent for 1 to 24 hours, followed by being treated with acid (such as hydrochloric acid, sulfuric acid) to give Compound (III-a).

Method 16: Compound (III-a) may be also synthesized according to the following method.

[Chemical formula 38]

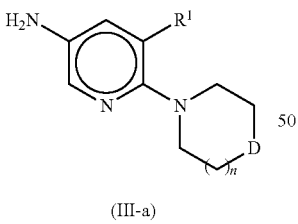

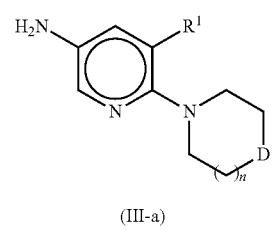

(In the formula, each symbol has the same meaning as defined above.)

(1) Compound (III-b) is reacted in an appropriate solvent (such as toluene, tetrahydrofuran, 1,4-dioxane) in the presence of catalyst (such as dibenzylideneacetone palladium, palladium acetate), ligand (such as triphenylphosphine, tris(tertiary butyl)phosphine) and lithium bis(trimethylsilyl)amide in the range from −20° C. to reflux temperature of solvent, followed by treating with tributylammonium fluoride, potassium fluoride, etc. to give Compound (III-a).

Compound (III-b) is also reacted in an appropriate solvent (such as toluene, tetrahydrofuran, 1,4-dioxane, 1,2-dimethoxyethane) under the condition using catalyst (such as tris(dibenzylideneacetone)dipalladium (0), palladium acetate), ligand (such as 2,2'-bis(diphenylphosphino)-1,1'-binaphthyl, 2-di-tert-butylphosphino-2',4',6'-triisopropyl-biphenyltriphenylphosphine), benzophenoneimine, and base (such as sodium tert-butoxide, tripotassium phosphate) in the range from room temperature to reflux temperature of solvent for 1 to 24 hours, followed by treating in an appropriate solvent (e.g., toluene, 1,4-dioxane, 1.2-dimethoxyethane, tetrahydrofuran, etc.) by adding acid such as 1N aqueous hydrochloric acid solution to give Compound (III-a).

(2) Compound (III-b) may be also reacted in an appropriate solvent (such as N,N-dimethylformamide) in the presence of catalyst (such as bis(acetylacetonate)copper (II)), acetylacetone, ammonia water and cesium carbonate as base in the range from 60° C. to 150° C. for 3 to 60 hours in a sealed tube to give Compound (III-a).

Method 17: Compound (III-c) may be synthesized according to the following method.

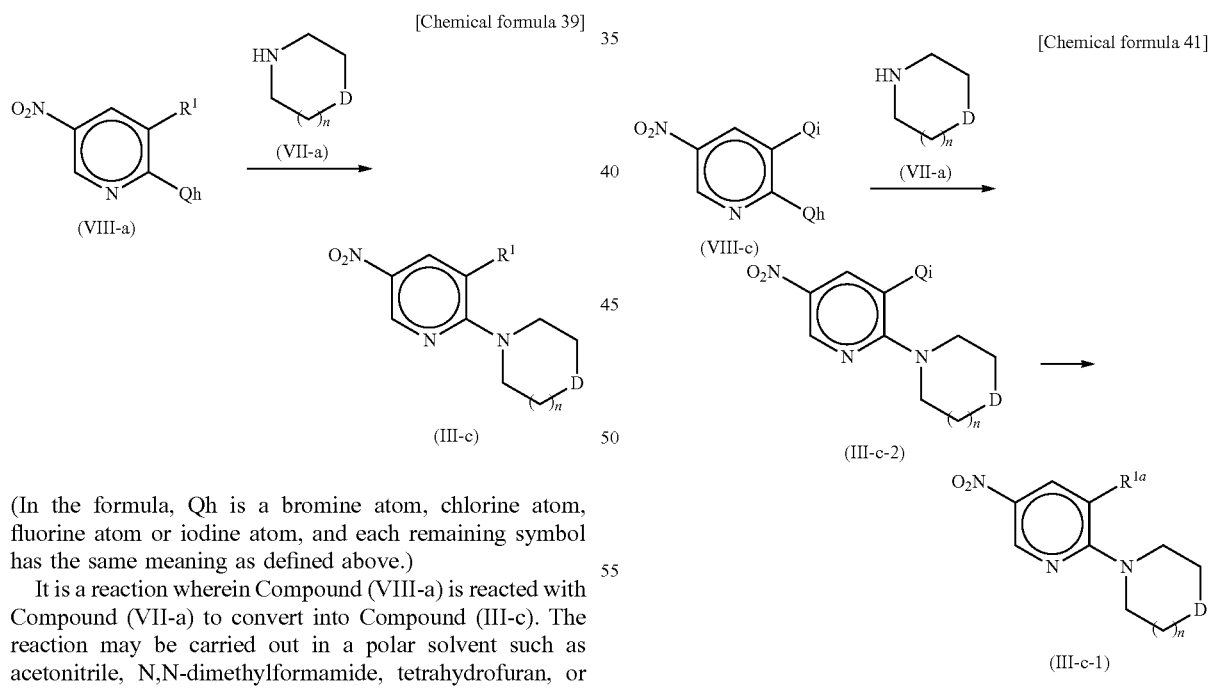

(In the formula, Qh is a bromine atom, chlorine atom, fluorine atom or iodine atom, and each remaining symbol has the same meaning as defined above.)

It is a reaction wherein Compound (VIII-a) is reacted with Compound (VII-a) to convert into Compound (III-c). The reaction may be carried out in a polar solvent such as acetonitrile, N,N-dimethylformamide, tetrahydrofuran, or an alcoholic solvent such as ethanol by using a base such as cesium carbonate or potassium carbonate, triethylamine or diisopropylethylamine. The reaction conditions are in the range from room temperature to reflux temperature for around 30 minutes to 24 hours. After the reaction, purification, etc. may be carried out according to the conventional method to give a desired compound. The reaction may be carried out by using Compound (VII-a) as a base.

Method 18: Compound (III-b) may be synthesized by using Compound (VIII-b) instead of Compound (VIII-a) in Method 17.

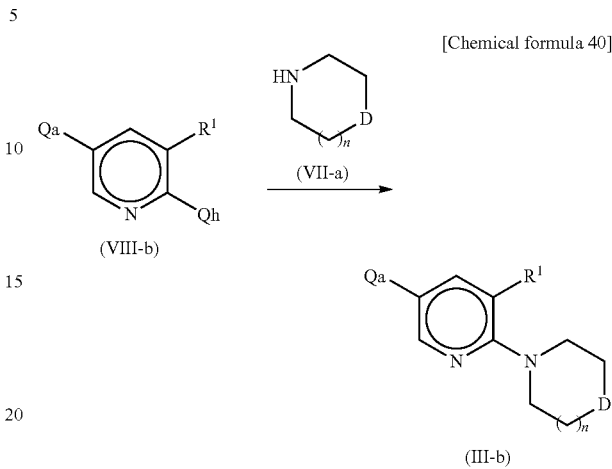

(In the formula, each symbol has the same meaning as defined above.)

Any appropriate combination may be used for Qa and Qh to give Compound (III-b) under a similar condition to that of Method 17.

Method 19: Compound (III-c-1) which is Compound (III-c) wherein $R^1$ is substituted by an alkyl group, cyano group or cycloalkyl group may be also synthesized according to the following method.

(In the formula, Qi is a bromine atom or chlorine atom, and $R^{1a}$ is an alkyl group, cyano group or cycloalkyl group. Each remaining symbol has the same meaning as defined above.)

The first step is a reaction wherein Compound (VIII-c) is reacted with Compound (VII-a) to convert into Compound (III-c-2), and may include similar reaction reagents and reaction conditions to those of Method 17.

The reaction wherein an intermediate (III-c-2) is converted into Compound (III-c-1) includes Suzuki coupling with boron acid or boron acid ester in case that $R^{1a}$ is an alkyl group or a cycloalkyl group. Specifically, the reaction may be carried out in a high polar solvent such as an ether type solvent such as 1,2-dimethoxyethane or tetrahydrofuran, or a hydrocarbon solvent such as toluene, N,N-dimethylformamide in the presence of a base such as cesium carbonate, tripotassium phosphate and palladium catalyst such as bis(tricyclohexylphosphine)palladium (II) dichloride. The reaction may be also carried out in an aqueous or biphasic solvent such as tetrahydrofuran and water, 1,2-dimethoxyethane and water in the presence of a base such as sodium hydroxide, sodium carbonate and palladium catalyst. Further, a reaction auxiliary such as 2-dicyclohexylphosphino-2',6'-dimethoxybiphenyl or 2-(di-t-butylphosphino)biphenyl may be optionally added thereto. The reaction conditions are in the range from room temperature to reflux temperature for around 30 minutes to 24 hours.

In case that $R^{1a}$ is a cyano group, reaction conditions using cyano zinc and a palladium catalyst such as tetrakis-triphenylphosphine palladium or tris(dibenzylideneacetone) palladium are included. A polar solvent such as N,N-dimethylformamide, dimethylacetamide in the range from 80° C. to reflux for around 2 to 48 hours is an option. Further, a reaction adjuvant such as 1,1'-bis(biphenylphosphino) ferrocene or 9,9-dimethyl4,5-bis(biphenylphosphino)xanthene may be optionally added thereto. Further, a conversion by copper iodide and sodium cyanide or potassium cyanide may be also carried out.

Method 20: Compound (III-b-2) which is Compound (III-b) wherein D is substituted by a carbonyl group and Compound (III-b-1) which is Compound (III-b) wherein $R^5$ is a hydroxy group, $R^6$ is a hydrogen atom may be synthesized according to the following method.

Compound (III-b-3) may be reacted with acid to give Compound (III-b-2). The acid used in the reaction includes trifluoroacetic acid, trifluoroacetic acid-water, aqueous hydrochloric acid solution, etc. If necessary, tetrahydrofuran, etc. may be added as solvent, for example. If necessary, a conventional quenching procedure is carried out. The reaction temperature is usually in the range from 0° C. to reflux temperature of solvent, and the reaction time varies depending on starting materials or solvents to be used, reaction temperature, and usually in the range from 1 to 24 hours.

Then, the reaction proceeds by adding a reducing agent to Compound (III-b-2) in an appropriate solvent to give Compound (III-b-1). The solvent used in the reaction includes, for example, methanol, ethanol, tetrahydrofuran, etc. The reducing agent includes, for example, sodium borohydride, lithium borohydride, lithium aluminum hydride, etc. The reaction temperature is usually in the range from −78° C. to reflux temperature of solvent, and the reaction time varies depending on starting materials or solvents to be used, reaction temperature, etc. and is usually in the range from 10 minutes to 24 hours.

Method 21: Compound (III-b-4) which is Compound (III-b) wherein $R_5$ is an amino group, and $R^6$ is a hydrogen atom may be synthesized according to the following method.

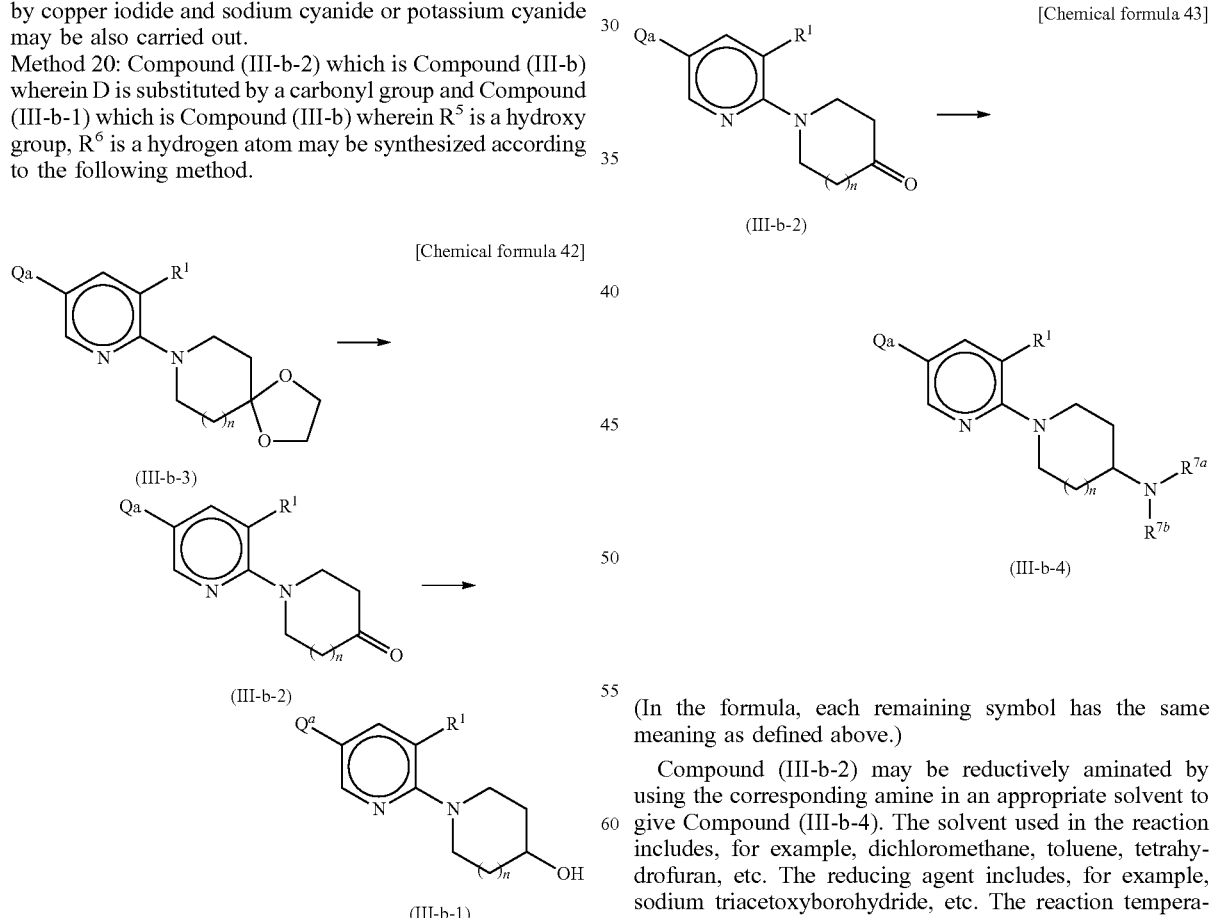

(In the formula, each symbol has the same meaning as defined above.)

(In the formula, each remaining symbol has the same meaning as defined above.)

Compound (III-b-2) may be reductively aminated by using the corresponding amine in an appropriate solvent to give Compound (III-b-4). The solvent used in the reaction includes, for example, dichloromethane, toluene, tetrahydrofuran, etc. The reducing agent includes, for example, sodium triacetoxyborohydride, etc. The reaction temperature is usually in the range from 0° C. to reflux temperature of solvent, and the reaction time varies depending on starting materials or solvents to be used, reaction temperature, etc. and is usually in the range from 1 to 48 hours.

Method 22: Compound (III-b-5) which is Compound (III-b) wherein $R^5$ is substituted by a hydroxy group may be synthesized according to the following method.

[Chemical formula 44]

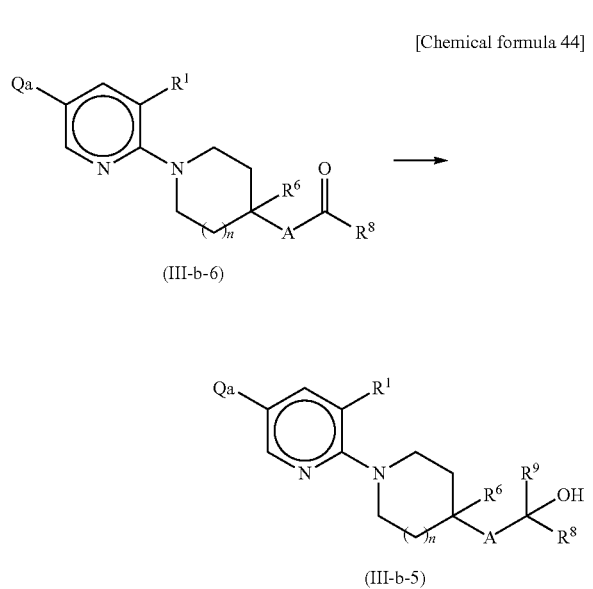

(III-b-6)

(III-b-5)

(In the formula, -A-C(OH)($R^8$)($R^9$) is $R^5$. A is a bond or alkylene group. $R^8$ is a hydrogen atom, alkyl group, cycloalkyl group. $R^9$ is a hydrogen atom, alkyl group, cycloalkyl group. Each remaining symbol has the same meaning as defined above.)

Compound (III-b-6) may be reacted with a metal organic reagent such as $R^9$MgBr or $R^9$Li to give Compound (III-b-5). The former is known as Grignard reaction, and Compound (III-b-6) is reacted with the corresponding magnesium halide in an appropriate solvent (such as tetrahydrofuran, diethyl ether, benzene, toluene, dichloromethane) in the range from −78° C. to reflux temperature for 30 minutes to 24 hours to give Compound (III-b-5). The magnesium halide reagent may be also generated in situ from metal magnesium and the corresponding halide. In case that $R^9$Li is used, Compound (III-b-6) is reacted with the corresponding lithium reagent in an appropriate solvent (such as tetrahydrofuran, diethyl ether, benzene, toluene) in the range from −78° C. to reflux temperature for 30 minutes to 24 hours to give Compound (III-b-5).

In case that $R^9$ is hydrogen, the reaction may proceed by adding a reducing agent in an appropriate solvent to give Compound (III-b-5). The solvent used in the reaction includes, for example, methanol, ethanol, tetrahydrofuran, etc. The reducing agent includes, for example, sodium borohydride, lithium borohydride, lithium aluminum hydride, etc. The reaction temperature is usually in the range from −78° C. to reflux temperature of solvent, and the reaction time varies depending on starting materials or solvents to be used, reaction temperature, etc. and is usually in the range from 10 minutes to 24 hours.

Method 23: Compound (II-b-7) which is Compound (II-b-5) wherein $R^8$ and $R^9$ are hydrogen atoms may be also synthesized according to the following method.

[Chemical formula 45]

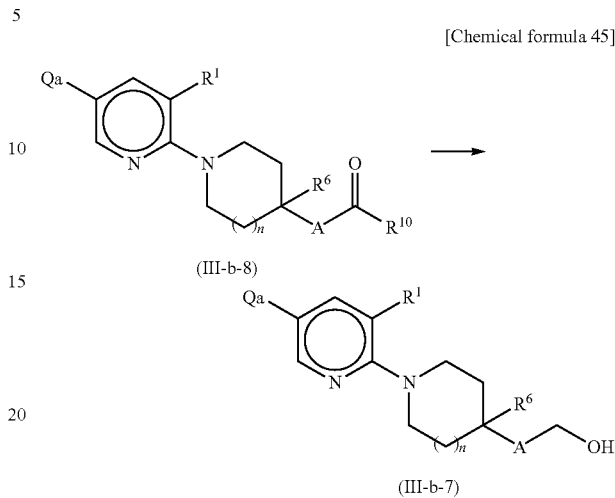

(III-b-8)

(III-b-7)

(In the formula, -A-$CH_2$—OH is $R^5$. $R^{10}$ is a hydrogen atom, hydroxy group or alkoxyl group. Each remaining symbol has the same meaning as defined above.)

The reaction may proceed by adding a reducing agent to Compound (III-b-8) in an appropriate solvent to give Compound (III-b-7). The solvent used in the reaction includes, for example, methanol, ethanol, tetrahydrofuran, etc. The reducing agent includes, for example, sodium borohydride, lithium borohydride, lithium aluminum hydride, etc. The reaction temperature is usually in the range from −78° C. to reflux temperature of solvent, and the reaction time varies depending on starting materials or solvents to be used, reaction temperature, etc. and is usually in the range from 10 minutes to 24 hours.

Method 24: Compound (III-b-9) which is Compound (III-b-7) wherein the hydroxy group in $R^5$ is an alkoxyl group may be synthesized according to the following method.

[Chemical formula 46]

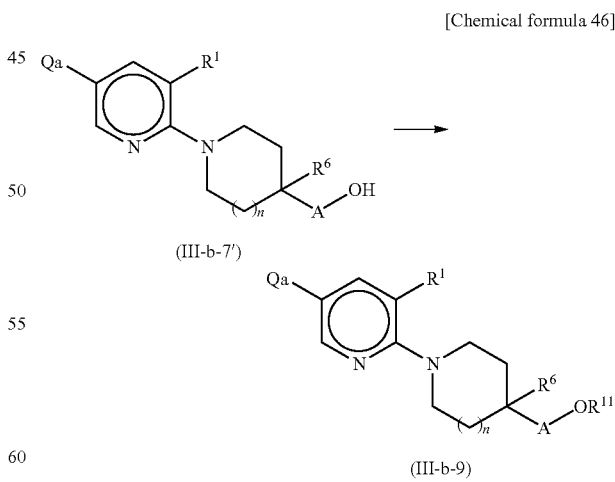

(III-b-7')

(III-b-9)

(In the formula, -A-$OR^{11}$ is $R^5$, and $OR^{11}$ is an optionally substituted alkoxyl group. Each remaining symbol has the same meaning as defined above.)

The reaction may proceed by adding a base and $R^{11}$—X (wherein X is a leaving group such as a halogen atom or trifluoromethanesulfonyloxy group, p-toluenesulfonyloxy group) to Compound (III-b-7') in an appropriate solvent to give Compound (III-b-9). The base includes inorganic bases such as sodium hydroxide or potassium carbonate, sodium hydride. The reaction conditions include conditions using polar solvents such as N,N-dimethylformamide, ether type solvents such as tetrahydrofuran or alcoholic solvents such as ethanol under ice cooling to reflux temperature for around 30 minutes to 12 hours. Mitsunobu reaction using phosphine compounds such as triphenylphosphine and azodicarboxylic acid derivatives such as azodicarboxylic acid diisopropyl ester may be also used. Any reaction condition which is usually used in this reaction may be used without limitation, and include, for example, the addition of the corresponding alcohol or carboxylic acid in a solvent such as tetrahydrofuran, toluene, dichloromethane under ice cooling to reflux temperature for around 30 minutes to 12 hours.

Method 25: Compound (III-b-10) which is Compound (III-b) wherein $R^5$ is substituted by a fluorine atom may be synthesized according to the following method.

[Chemical formula 47]

(III-b-5)

(III-b-10)

(In the formula, -A-CF($R^8$)($R^9$) is $R^5$. Each symbol has the same meaning as defined above.)

The hydroxy group of Compound (III-b-5) may be fluorinated to give a fluoride (III-b-10). The reagent used in the fluorination may include diethylaminosulfur trifluoride (DAST) or 2,2-difluoro-1,3-dimethylimidazolidine (DFI), etc. In the present step, the reaction may be carried out in a halogen type solvent such as methylene chloride, or hydrocarbon solvent such as hexane. The reaction conditions include the range from −78° C. to room temperature for around 30 minutes to 12 hours. After the reaction, purification in a conventional manner, etc. may give the desired compound.

The present step may be also carried out by converting the hydroxy group into the corresponding sulfonate, followed by treating with a fluoride ion. For example, in case that p-toluenesulfonyl fluoride and tetrabutylammonium fluoride (TBAF) are used, the reaction is carried out in an ether type solvent such as tetrahydrofuran in the range from room temperature to 80° C. for around 1 to 24 hours. A dehydrating agent such as molecular sieves may be added in the reaction. After the reaction, purification in a conventional manner, etc. may give the desired compound.

Method 26: Compound (III-a) which is Compound (III-b) of Methods 20 to 25 wherein Qa is an amino group (or a precursor thereof, e.g. a protected compound), Compound (III-c) which is Compound (III-b) wherein Qa is a nitro group, and Compound (III-d) which is Compound (III-b) wherein Qa is a hydroxycarbonyl group (or a precursor thereof, e.g. ester) may be synthesized from the corresponding compound, respectively. Then, a compound wherein Qa is structure (II) may be also used to synthesize.

[Chemical formula 48]

(II)

Method 27: Compound (II-a-8) which is Compound (II-a) wherein Y and Z are nitrogen atoms, X and W are carbon atoms, and the 4 position of imidazole is substituted by a carboxyl group may be also synthesized according to the following method.

[Chemical formula 49]

(V-i)

(IV-f)

(II-a-8')

(II-a-8)

(In the formula, each symbol has the same meaning as defined above.)

Compound (V-i) and Compound (IV-f) may be reacted in an appropriate solvent (including an alcohol type solvent such as methanol, ethanol, ether type solvent such as diphenylether, hydrocarbon type solvent such as toluene, benzene, or a mixed solvent thereof) under reflux for 1 to 48 hours to give Compound (II-a-8'), followed by hydrolysis in a conventional manner to give Compound (II-a-8). They may be also reacted with an organic base such as triethylamine, inorganic base such as potassium carbonate in the range from room temperature to reflux for 1 to 24 hours to give Compound (II-a-8').

Method 28: Compound (II-a-9) which is Compound (II-a) wherein X, Y and W are nitrogen atoms. Z is a carbon atom, and the 4 position of triazole is substituted by a carboxyl group may be synthesized according to the following method.

Method 29: Compound (II-a-10) which is Compound (II-a) wherein X, Y and Z are nitrogen atoms, W is a carbon atom, and the 4 position of triazole is substituted by a carboxyl group may be synthesized according to the following method.

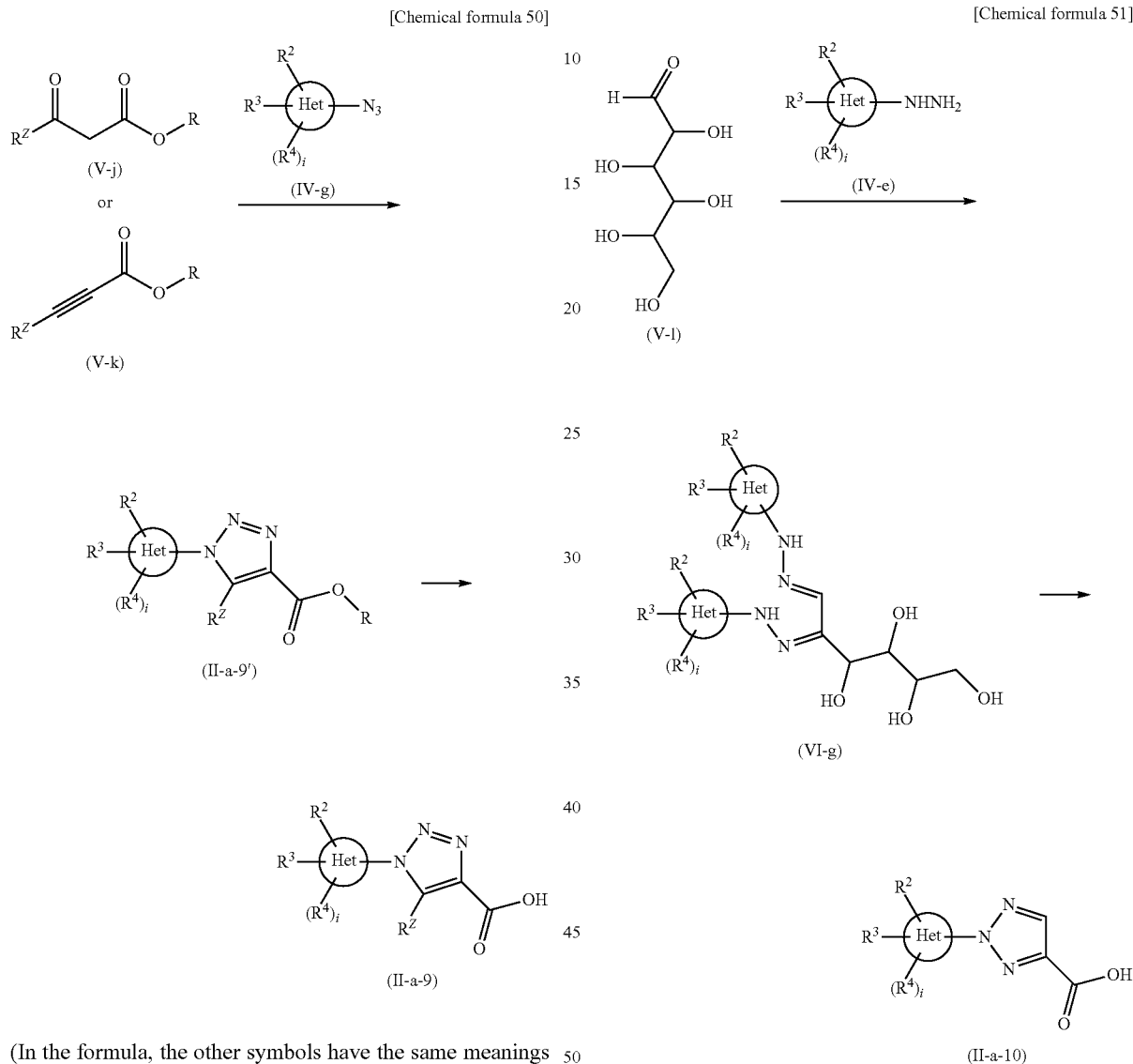

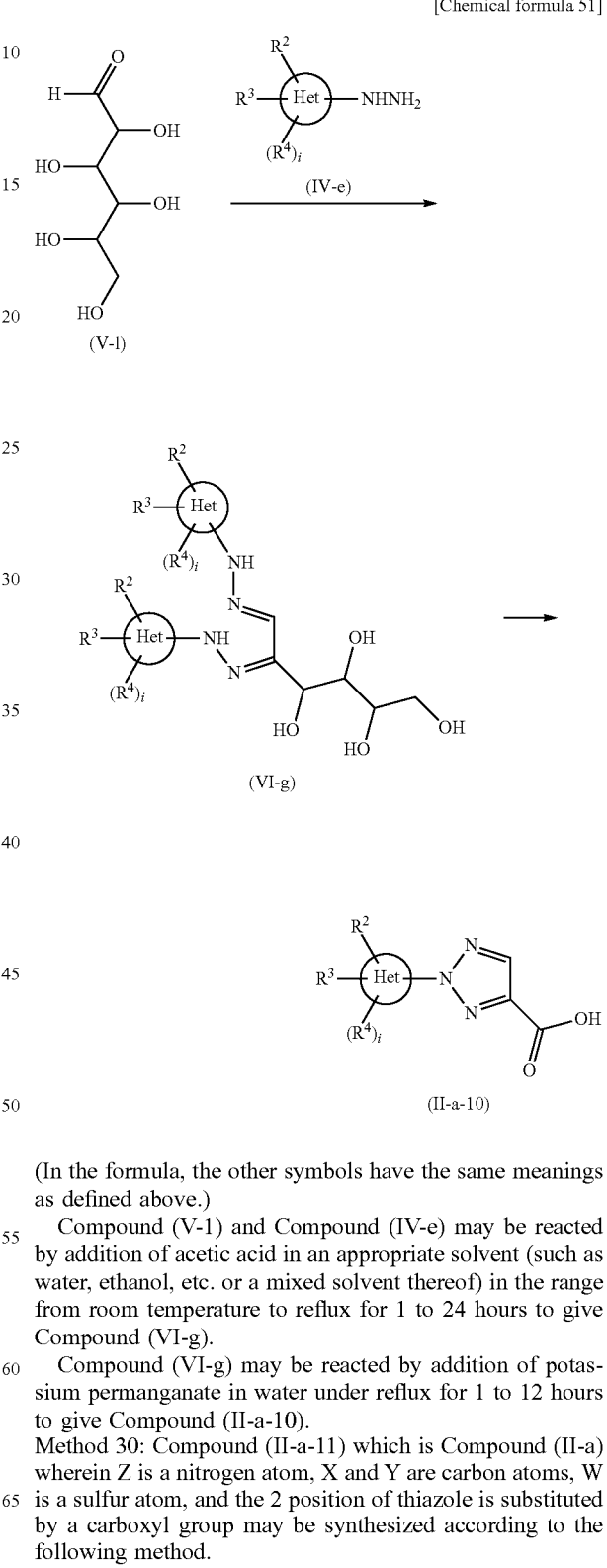

(In the formula, the other symbols have the same meanings as defined above.)

Compound (V-j) and Compound (IV-g) may be reacted by addition of an inorganic base such as potassium carbonate, sodium ethoxide, organic base such as triethylamine in an appropriate solvent (such as N,N-dimethylformamide or dimethylsulfoxide, ethanol, etc.) in the range from room temperature to reflux for 1 to 48 hours to give Compound (II-a-9'), followed by hydrolysis according to the conventional method to give Compound (II-a-9).

Compound (V-k) may be also reacted instead of Compound (V-j) under a similar condition to that of Method 27 to give Compound (II-a-9'). The reaction may be also carried out using a copper reagent such as copper iodide or copper acetate and an organic base such as triethylamine to give Compound (II-a-9').

(In the formula, the other symbols have the same meanings as defined above.)

Compound (V-1) and Compound (IV-e) may be reacted by addition of acetic acid in an appropriate solvent (such as water, ethanol, etc. or a mixed solvent thereof) in the range from room temperature to reflux for 1 to 24 hours to give Compound (VI-g).

Compound (VI-g) may be reacted by addition of potassium permanganate in water under reflux for 1 to 12 hours to give Compound (II-a-10).

Method 30: Compound (II-a-11) which is Compound (II-a) wherein Z is a nitrogen atom, X and Y are carbon atoms, W is a sulfur atom, and the 2 position of thiazole is substituted by a carboxyl group may be synthesized according to the following method.

[Chemical formula 52]

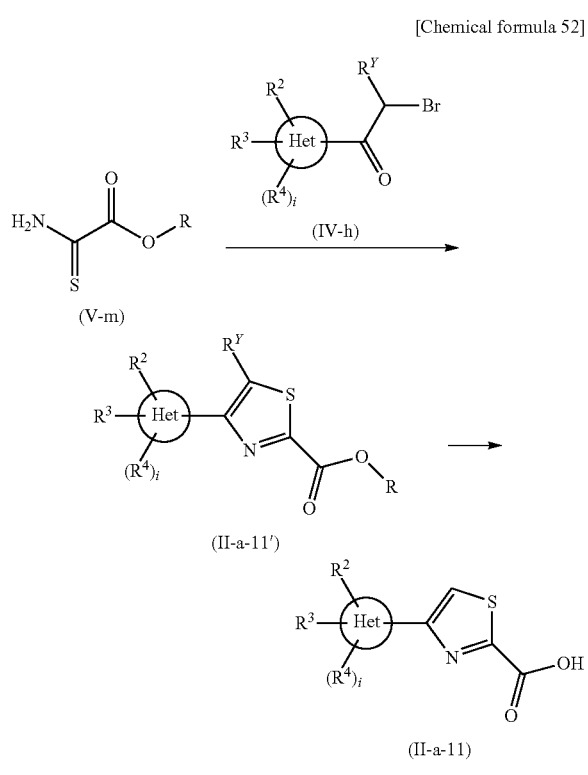

(In the formula, the other symbols have the same meanings as defined above.)

Compound (V-m) and Compound (IV-h) may be reacted in an appropriate solvent (ethanol, N,N-dimethylformamide, acetonitrile, etc. or a mixed solvent thereof) in the range from room temperature to reflux for 1 to 24 hours to give Compound (II-a-11'), followed by hydrolysis according to the conventional method to give Compound (II-a-11).

Method 31: Compound (II-a-12) which is Compound (II-a) wherein Z is a nitrogen atom, X and W are carbon atoms, Y is a sulfur atom, and the 4 position of thiazole is substituted by a carboxyl group may be also synthesized according to the following method.

[Chemical formula 53]

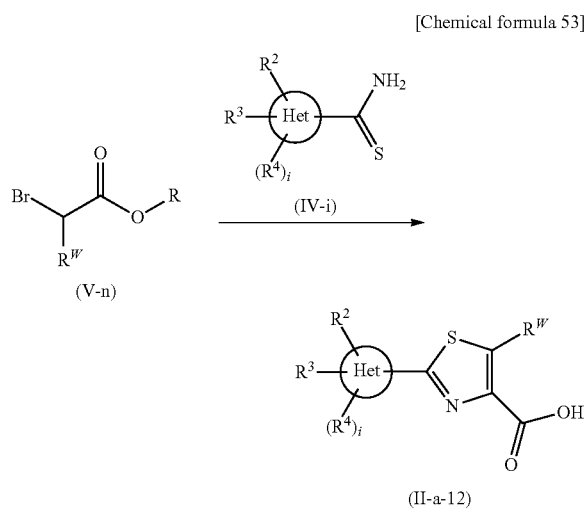

(In the formula, the other symbols have the same meanings as defined above.)

Compound (V-n) and Compound (IV-i) may be reacted in an appropriate solvent (ethanol, 1,4-dioxane, acetonitrile, water, etc. or a mixed solvent thereof) in the range from room temperature to reflux for 1 to 24 hours to give Compound (II-a-12).

Method 32: Compound (II-a-13) which is Compound (II-a) wherein Z is a nitrogen atom, X and Y are carbon atoms, W is a sulfur atom, and the 2 position of thiazole is substituted by a carboxyl group may be synthesized according to the following method.

[Chemical formula 54]

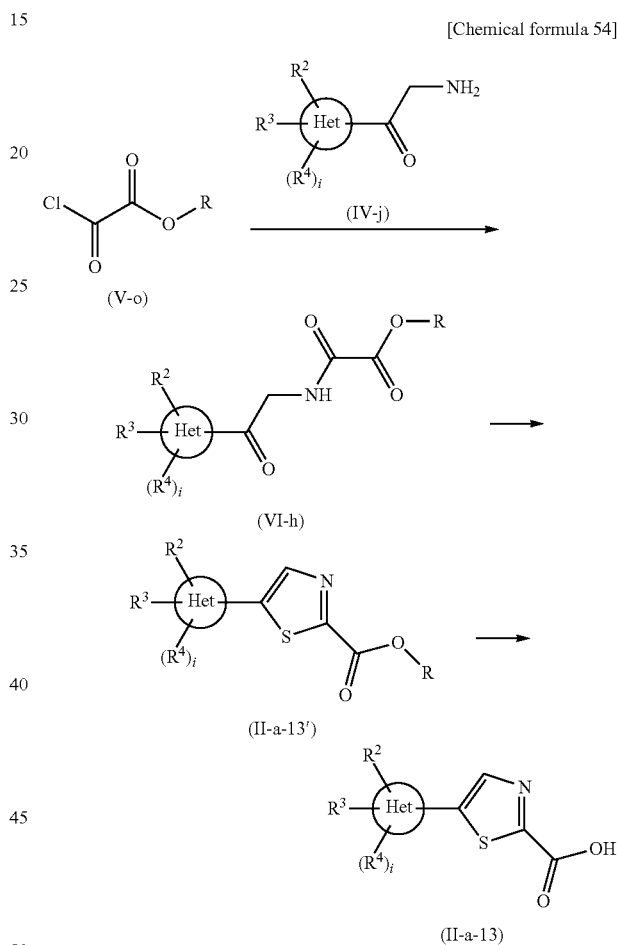

(In the formula, other symbols have the same meanings as defined above.)

(1) Compound (V-o) and Compound (IV-j) may be reacted in the presence of an organic base such as triethylamine, pyridine, N,N-diisopropylmethylamine or an inorganic base such as potassium carbonate, sodium hydrogen carbonate in an appropriate solvent (e.g., dichloromethane, tetrahydrofuran, toluene, N,N-dimethylformamide, water, etc. or a mixed solvent thereof) in the range from 0° C. to reflux for 1 to 12 hours to give Compound (VI-h).

(2) Compound (VI-h) is reacted with a sulfur introducing agent in an appropriate solvent (e.g., 1,4-dioxane, tetrahydrofuran, dichloromethane, toluene, methanol or a mixed solvent thereof, etc.) in the range from 0° C. to reflux for 1 to 24 hours to give Compound (II-a-13'). The sulfur introducing agent includes, for example, Lawesson's reagent or phosphorus pentasulfide. Compound (II-a-13') may be hydrolyzed according to the conventional method to give Compound (II-a-13).

A compound group which is the general formula (I) wherein X is N, Z is N—$R^Z$, and W is CH is represented by the general formula (I)a, and the compound group of the general formula (I)a as mentioned above may be also prepared.

In the methods as mentioned above, protection or deprotection of substituents may be optionally carried out in any stage.

The compound of the present invention or a salt thereof includes both solvates or hydrates thereof. The compound of the present invention may be optionally converted into an acid addition salt by treating with inorganic or organic acid in a conventional manner, and a base addition salt by treating with inorganic or organic base in a conventional manner in an appropriate solvent. It may be also converted into the corresponding metal salt by treating with alkali metal salt or alkali earth metal salt, etc. in a conventional manner. It may be also converted into the corresponding hydrate or solvate by treating with water, aqueous solvent or other solvents in a conventional manner. It may be also converted into N-oxide compound by treating with an oxidizing agent such as hydrogen peroxide, metachloroperbenzoic acid in a conventional manner.

The compounds and each intermediate obtained in the above are isolated and purified by conventional chemical operations or known methods in the organic synthetic chemistry such as extraction, crystallization, recrystallization, various chromatography methods.

An acid addition salt or a base addition salt may be used as a pharmacologically acceptable salt of the compound of the above general formula (I) or (I)a, and the type of salts may not be limited as long as it is acceptable as a medicine. A pharmacologically acceptable salt of the compound of the general formula (I) or (I)a also includes a solvate.

A pharmacologically acceptable salt of the compound of the general formula (I) or (I)a, or a solvate thereof may be prepared from amidopyridine derivative of the general formula (I) according to the known method. For example, a pharmacologically acceptable salt of the compound of the general formula (I) or (I)a may be obtained by reacting the compound of the general formula (I) or (I)a with inorganic acid, organic acid, inorganic base or organic base, and a solvate of the compound of the general formula (I) or (I)a or a physiologically acceptable salt thereof may be obtained by reacting the compound of the general formula (I) or (I)a or a physiologically acceptable salt thereof with organic solvent such as water or ethanol.

In case that the compound of the general formula (I) or (I)a, or a salt thereof is a racemate or includes optically active compounds, it may be separated into individual optical isomer by the conventional optical resolution means. For example, it may be divided into the desired optically active compounds by fractional crystallization by a salt formation with an optically active acid or base, or by passing through a column loaded with optically active carriers. Alternatively, an optically active compound of the compound of the general formula (I), or a salt thereof may be synthesized by using optically pure starting materials or compounds which configurations are known.

One or more of the compound of the present invention or a pharmacologically acceptable salt thereof, or a solvate thereof may be directly administered to patients, and may be preferably provided as a formulation in the form well known to a skilled person by adding the active ingredient and pharmacologically and pharmaceutically acceptable additives.

The compound of the present invention or a pharmacologically acceptable salt thereof, or a solvate thereof is useful for prophylaxis or treatment of autoimmune diseases or inflammatory/allergic diseases, since it inhibits the production of cytokines from T cells (e.g., productions of IL-17 or other inflammatory cytokines (including IFN-γ), etc.). Herein, the autoimmune disease includes rheumatoid arthritis, multiple sclerosis, systemic lupus crythematosus, psoriasis, inflammatory bowel disease, transplantation rejection, etc., and the inflammatory/allergic disease includes asthma, etc. In the present invention, "prophylaxis" refers to the action administering the compound of the present invention or a pharmaceutical composition comprising the same to an individual wherein diseases, disorders or symptoms have not been developed. "Treatment" refers to the action administering the compound of the present invention or a pharmaceutical composition comprising the same to an individual wherein diseases, disorders or symptoms have been already developed. Thus, the action administering to an individual wherein diseases, disorders or symptoms have been already developed for the purpose of prevention of degradation, attack or relapse of symptoms, etc. is one embodiment of "treatment".

The compound of the present invention or a pharmacologically acceptable salt thereof, or a solvate thereof may be optionally used in combination with other immunosuppressants, steroid drugs, anti-allergic drugs, etc.

Timing of administration of the compound of the present invention or a pharmacologically acceptable salt thereof, or a solvate thereof and a combined drug is not intended to be limited, and they may be administered to subjects concurrently or with temporal intervals. Further, the compound of the present invention and a combined drug may be administered as two types of formulations each of which contains each active ingredient or as a single formulation comprising both active ingredients.

The dosage amounts of the combined drug may be optionally selected on the basis of clinically used dosages. Combination ratios of the compound of the present invention and the combined drug may be optionally selected depending on administration subjects, administration routes, subject diseases, conditions, a combination thereof, etc. For example, when the administration subject is human, 0.01 to 100% by weight of the combined drug to 1 part by weight of the compound of the present invention may be used.

The compound of the present invention may be prepared in an appropriate dosage form (including powders, injections, tablets, capsules or topical external preparations) together with appropriate conventional diluents and other additives, followed by being administered to human or animals by appropriate administration routes depending on its dosage form (e.g., intravenous administration, oral administration, cutaneous administration or topical administration, etc.).

As the pharmacologically and pharmaceutically acceptable additive, excipients, disintegrants, binders, lubricants, coating agents, pigments, diluents, bases and tonicity agents, etc. may be used.

A preparation appropriate for oral administration may include tablets, capsules, powders, fine granules, granules, liquids or syrups, etc. and a preparation appropriate for parenteral administration may include injections, drops or suppositories, etc.

In the preparation appropriate for oral administration, additives such as excipients, disintegrants, binders, lubricants, coating agents or bases, etc. may be used. When the compound of the present invention is administered to patients as a therapeutic subject, other drugs appropriate for treating the subject disease may be used concurrently with the compound of the present invention.

An administration route of the medicine of the present invention is not limited specifically, and it may be either orally or parenterally administered. Dosage amounts are determined by taking into account age, weight, general health condition, sex, diet, administration time, administration method, excretory time, combination of drugs, conditions of disease under treatment at the time, or other factors. The compound of the present invention, optical isomers thereof or pharmaceutically acceptable salts thereof may be safely used with low toxicity. The dosage amounts per day differ depending on conditions and weight of patients, kinds of compounds, administration routes, etc., and, for example, about 0.1 to 1000 mg/person/day, preferably 1 to 500 mg/person/day are parenterally administered via subcutaneously, intravenously, intramuscularly or rectally, and about 0.1 to 1000 mg/person/day, preferably 1 to 500 mg/person/day are orally administered.

The present invention is explained by Examples of the present invention in more detail as below, but the scope of the present invention is not intended to be limited thereto.

The "room temperature" in the following Examples refers to 10 to 30° C. The solvent ratios in a mixed solvent refer to volume ratios.

Mass spectra were determined by LCMS (liquid chromatograph mass spectrometer) using the following (1), (2) or (3) instrument, and conditions. ESI (electrospray ionization) method, or APCI (atmospheric pressure chemical ionization) method was used as a MS measurement mode. Unless otherwise specified, each compound was determined by ESI method. Unless otherwise specified, each compound was determined by ESI method.

(1) LC-2010 (manufactured by Shimadzu Corporation) was used as an instrument, and Chromolith SpeedROD RP-18e (4.6 mmϕ×50 mm) (manufactured by Merck) was used as a column. For the measurement conditions, a gradient elution was carried out under 2.0 ml/min of a flow rate and a mixed solvent of solution A (0.05% trifluoroacetic acid/water) and solution B (0.05% trifluoroacetic acid/acetonitrile) as a solvent from solution A:solution B=95:5 to solution A:solution B=0:100 for 4 minutes;
(2) Acquity/ZQ (manufactured by Waters) or SQD was used as an instrument, and Acquity UPLC BEH C18 (2.1 mmϕ× 50 mm) (manufactured by Waters) was used as a column. For the measurement conditions, a gradient elution was carried out under 0.6 ml/min of a flow rate and a mixed solvent of solution A (0.05% trifluoroacetic acid/water) and solution B (0.05% trifluoroacetic acid/acetonitrile) or a mixed solvent of solution A (0.05% formic acid/water) and solution B (0.05% formic acid/acetonitrile) as a solvent from solution A:solution B=95:5 to solution A:solution B=2:98 for 1 minute.
(3) LXQ (manufactured by Thermo Fisher Scientific) was used as an instrument, and for the measurement conditions, 0.2 ml/min of a flow rate and a mixed solvent of 80% methanol/water were used, and samples were injected by flow injection method using a LC instrument without separation by column chromatography.

$^1$H-NMR (proton nuclear magnetic resonance spectra) was measured at 400 MHz or 300 MHz. Relative delta (δ) values of chemical shifts of $^1$H-NMR were represented by ppm using tetramethylsilane (TMS) as an internal standard. s refers to singlet, d refers to doublet, t refers to triplet, q refers to quartet, m refers to multiplet, broad refers to a broad absorption peak, and brs refers to a broad singlet.

Other abbreviations used herein refer to the following meanings.

CDCl$_3$: deuterochloroform

DMSO-d$_6$: hexadeuterodimethyl sulfoxide

As to a nomenclature of compounds, in case that a compound has benzimidazole, etc. as a substituent group, its tautomers may exist. Thus, in such case, substituent positions were described as "-5(6)-yl", for example.

EXAMPLES

Reference Example 1

5-methyl-1-[5-(trifluoromethyl)pyridin-2-yl]-1H-pyrazole-4-carboxylic acid chloride (1) To ethanol (60 ml) were added 2-chloro-5-(trifluoromethyl)pyridine (25 g) and hydrazine hydrate (100%) (100 ml), and the mixture was stirred at 100° C. for 3 hours. Then, the reaction solution was concentrated under reduced pressure, and to the residue were added chloroform and water. The organic layer was separated, and dried over anhydrous sodium sulfate, and then solvent was removed under reduced pressure. To the residue was added 4N hydrochloric acid-ethanol solution to give 5-(trifluoromethyl)pyridin-2-ylhydrazine hydrochloride (15.4 g). MS(ESI) m/z: 178 (M+H)$^+$.
(2) Then, ethyl 2-ethoxymethylene acetoacetate (6.1 g) synthesized according to the method described in J. Chem. Soc. Perkin trans. I, p. 1875 (1988) and 5-(trifluoromethyl)pyridin-2-ylhydrazine hydrochloride (7.0 g) mentioned above were added to a mixed solvent of water (40 ml) and ethanol (40 ml), and stirred at reflux temperature for 3 hours, and then to the reaction solution was added sodium hydroxide (2.6 g). The mixture was stirred for additional 1 hour. The reaction solution was treated with 1N aqueous hydrochloric acid solution, and the precipitated solid was purified by a mixed solvent of ethyl acetate-n-hexane to give 5-methyl-1-[5-(trifluoromethyl)pyridin-2-yl]-1H-pyrazole-4-carboxylic acid (6.5 g). MS(ESI) m/z: 272 (M+H)$^+$.
(3) To a solution of 5-methyl-1-[5-(trifluoromethyl)pyridin-2-yl]-1H-pyrazole-4-carboxylic acid (40.0 g) in toluene (147 ml) were added N,N-dimethylformamide (catalytic amount) and thionyl chloride (52.6 g) at room temperature, and the mixture was stirred at 80° C. for 4.5 hours. After the completion of reaction, solvent and excess thionyl chloride were distilled away, and the resultant was subjected to azeotropy with toluene twice, followed by being dried under reduced pressure to give the titled compound as a pale yellow solid. $^1$H-NMR (400 MHz, CDCl$_3$) δ: 3.00 (3H, s), 8.08-8.16 (2H, m) 8.20 (1H, s), 8.79 (1H, s).

Reference Example 2

1-(5-chloropyridin-2-yl)-5-methyl-1H-pyrazole-4-carboxylic acid

In Reference example 1, 2,5-dichloropyridine was used instead of 2-chloro-5-(trifluoromethyl)pyridine to be reacted and treated in a similar manner to (1) and (2) to give the titled compound. MS(ESI) m/z: 238 (M+H)$^+$.

Reference Example 3

1-(3,5-dichloropyridin-2-yl)-5-methyl-1H-pyrazole-4-carboxylic acid (1) 2,3,5-Trichloropyridine (25 g) and hydrazine monohydrate (109.8 g) were added to ethanol (20 ml), and the mixture was stirred at 100° C., and then let stand to be cooled to room temperature. The resulted solid was filtered to give 3,5-dichloropyridin-2-ylhydrazine (24.07 g).
(2) Then, to ethyl 2-ethoxymethylene acetoacetate (25.1 g) synthesized according to the method described in J. Chem. Soc. Perkin trans. I. p. 1875 (1988) was added a solution of 1N aqueous hydrochloric acid solution (135 ml) and 3,5-dichloropyridin-2-ylhydrazine (24.02 g) mentioned above in ethanol (135 ml), and the mixture was stirred at reflux temperature for 3 hours, and then let stand to be cooled to room temperature. To the reaction solution was added water, and the resulted solid was filtered and purified by a mixed solvent of ethyl acetate/n-hexane to give 1-(3,5-dichloropyridin-2-yl)-5-methyl-1H-pyrazole-4-carboxylic acid ethyl ester.
(3) To 1-(3,5-dichloropyridin-2-yl)-5-methyl-1H-pyrazole-4-carboxylic acid ethyl ester (1.0 g) were added 4N aqueous sodium hydroxide solution (10 ml) and water (10 ml), and the mixture was stirred at 80° C. for 2.5 hours. The reaction solution was washed with ethyl acetate, and then to the aqueous layer was added 1N aqueous hydrochloric acid solution at 0° C. The precipitated solid was filtered and washed with water to give the titled compound (680 mg) as a white solid. MS(ESI) m/z: 272 (M+H)$^+$.

Reference Example 4

1-(4-fluorophenyl)-5-methyl-1H-pyrazole-4-carboxylic acid

To a solution of ethyl 2-ethoxymethylene acetoacetate (28.63 g) synthesized according to the method described in J. Chem. Soc. Perkin trans. I, p. 1875 (1988) in ethanol (75 ml) was added a solution of 4-fluorophenylhydrazine hydrochloride (25 g) in 1N aqueous hydrochloric acid solution (75 ml), and the mixture was stirred at reflux temperature for 3 hours. Ethanol was distilled away, and then to the residue was added sodium hydroxide (12 g), and the mixture was stirred at reflux temperature for 3 hours. After the reaction, solvent was distilled away, and thereto was added diluted hydrochloric acid, and then the resulted solid was washed with ethyl acetate to give the titled compound (16.08 g). MS(ESI) m/z: 221 (M+H)$^+$.

Reference Example 5

5-methyl-1-(4-methylphenyl)-1H-pyrazole-4-carboxylic acid

To a solution of ethyl 2-ethoxymethylene acetoacetate (16.67 g) synthesized according to the method described in J. Chem. Soc. Perkin trans. I, p. 1875 (1988) in ethanol (70 ml) and water (70 ml) was added 4-methylphenylhydrazine hydrochloride (14.2 g), and the mixture was stirred at reflux temperature for 7.5 hours, and then thereto was added sodium hydroxide (8.5 g), and the mixture was stirred at reflux temperature for additional 1 hour. After the reaction, solvent was distilled away and thereto was added diluted hydrochloric acid, and then the mixture was extracted with ethyl acetate. The organic layer was dried over anhydrous magnesium sulfate, and then solvent was distilled away. The residue was washed with n-hexane to give the titled compound (11.17 g). MS(ESI) m/z: 217 (M+H)$^+$.

Reference Example 6

1-(4-chlorophenyl)-5-methyl-1H-pyrazole-4-carboxylic acid

In Reference example 4, 4-chlorophenylhydrazine sulfate was used instead of 4-fluorophenylhydrazine hydrochloride to be reacted and treated in a similar manner to give the titled compound. MS(ESI) m/z: 237 (M+H)$^+$.

Reference Example 7

1-(2,4-dichlorophenyl)-5-methyl-1H-pyrazole-4-carboxylic acid

In Reference example 4, 2,4-dichlorophenylhydrazine hydrochloride was used instead of 4-fluorophenylhydrazine hydrochloride to be reacted and treated in a similar manner to give the titled compound. MS(ESI) m/z: 271 (M+H)$^+$.

Reference Example 8

1-(4-chlorophenyl)-5-(trifluoromethyl)-1H-pyrazole-4-carboxylic acid

In Reference example 4, ethyl ethoxymethylene-3-oxo-4,4,4-trifluorobutyrate was used instead of ethyl 2-ethoxymethylene acetoacetate and 4-chlorophenylhydrazine hydrochloride was used instead of 4-fluorophenylhydrazine hydrochloride to be reacted and treated in a similar manner to give the titled compound. MS(ESI) m/z: 291 (M+H)$^+$.

Reference Example 9

1-(3-chlorophenyl)-5-methyl-1H-pyrazole-4-carboxylic acid

In Reference example 4, 3-dichlorophenylhydrazine was used instead of 4-fluorophenylhydrazine hydrochloride to be reacted and treated in a similar manner to give the titled compound. MS(EI) m/z: 236 (M+H)$^+$.

Reference Example 10

5-methyl-1-[4-(trifluoromethyl)phenyl]-1H-pyrazole-4-carboxylic acid

In Reference example 4, 4-(trifluoromethyl)phenylhydrazine was used instead of 4-fluorophenylhydrazine hydrochloride to be reacted and treated in a similar manner to give the titled compound. MS(ESI) m/z: 271 (M+H)$^+$.

Reference Example 11

1-(4-methoxyphenyl)-5-methyl-1H-pyrazole-4-carboxylic acid

In Reference example 4, 4-methoxyphenylhydrazine hydrochloride was used instead of 4-fluorophenylhydrazine hydrochloride to be reacted and treated in a similar manner to give the titled compound. MS(ESI) m/z: 233 (M+H)$^+$.

Reference Example 12

1-(4-chlorophenyl)-5-cyclopropyl-1H-pyrazole-4-carboxylic acid (1) To a solution of 3-cyclopropyl-3-oxopropanoic acid methyl ester (4.9 g) in ethyl acetate (50 ml) was added N,N-dimethylformamidedimethylacetal (4.31 g) at room temperature, and the mixture was stirred at 75° C. for 3 hours. Then, the mixture was cooled to room temperature, then thereto were added 4-chlorophenylhydrazine hydrochloride (7.52 g) and triethylamine (7.0 ml), and the mixture was stirred at 75° C. for 4 hours. After the completion of the reaction, to the mixture was added water, and the mixture was extracted with ethyl acetate and washed with water twice. The organic layer was dried, and then solvent was distilled away. The resulted residue was purified by silica gel column chromatography (chloroform:methanol) to give a mixture (7.7 g).

(2) To a solution of the resulted compound (7.7 g) in methanol (45 ml) was added at room temperature 4N aqueous sodium hydroxide solution (8.4 ml), and the mixture was stirred for 1 hour under reflux. After the completion of the reaction, the mixture was cooled to room temperature, and thereto were added water (100 ml) and activated carbon (1 g), and then the mixture was stirred at room temperature for 0.25 hour. After the completion of the reaction, the mixture was filtered, and to the resulted aqueous layer was added 1N aqueous hydrochloric acid solution (until about pH3), and the mixture was extracted with ethyl acetate twice. The organic layer was washed with saturated saline, dried over anhydrous sodium sulfate, and then solvent was distilled away to some extent. To the resulted solution was added n-hexane, and the mixture was stirred at 0° C., and then filtered to give the titled compound (5.8 g) as a white solid. MS(ESI) m/z: 263 (M+H)$^+$.

Reference Example 13

1-(4-tert-butylphenyl)-5-methyl-1H-pyrazole-4-carboxylic acid

To a solution of ethyl 2-ethoxymethylene acetoacetate (13.92 g) synthesized according to the method described in J. Chem. Soc. Perkin trans. I, p. 1875 (1988) in ethanol (45 ml) was added an aqueous solution (45 ml) of 4-tert-butylphenylhydrazine hydrochloride (15.0 g), and the mixture was stirred at reflux temperature for 4 hours. To the reaction solution was added water, and then the mixture was extracted with ethyl acetate, washed with saturated saline and solvent was distilled away under reduced pressure. To the residue were added sodium hydroxide (5.9 g), water (45 ml) and ethanol (45 ml), and the mixture was stirred at reflux temperature for 2 hours. After the reaction, solvent was distilled, and the resultant was washed with toluene and was acidified by adding diluted hydrochloric acid to the aqueous layer, followed by being extracted with ethyl acetate. The resultant was dried over anhydrous magnesium sulfate, and then solvent was distilled away under reduced pressure. The precipitated solid was re-purified by ethyl acetate/n-hexane solvent to give the titled compound (4.50 g). MS(ESI) m/z: 259 (M+H)$^+$.

Reference Example 14

1-(5-cyanopyridin-2-yl)-1H-pyrrole-3-carboxylic acid (1) To a suspension of sodium hydride (6.14 g) in tetrahydrofuran (250 ml) were added dropwise a solution of acrylic acid tert-butyl ester (16.4 g) and 4-toluenesulfonylmethyl isocyanide (25.0 g) in tetrahydrofuran (250 mL) at 70° C. over 0.5 hour, and then the mixture was stirred at the same temperature for 2 hours. After the completion of reaction, solvent was distilled away, and thereto was added water, and the mixture was extracted with ethyl acetate three times. The organic layer was dried over anhydrous magnesium sulfate, and then solvent was distilled away. The resulted residue was purified by silica gel column chromatography (n-hexane:ethyl acetate), and then recrystallized in a mixed solvent of ethyl acetate/n-hexane to give 1H-pyrrole-3-carboxylic acid tert-butyl ester (10.6 g) as a white solid. MS(ESI) (m/z): 12 (M+H–$^t$Bu)$^+$.

(2) To a solution of 1H-pyrrole-3-carboxylic acid tert-butyl ester (1.21 g) in N,N-dimethylformamide (14 ml) was added sodium hydride (346 mg) at room temperature, and the mixture was stirred at the same temperature for 0.5 hour. Then, thereto was added 2-chloro-5-cyanopyridine (1.0 g), and the mixture was stirred at the same temperature for 1 hour. After the completion of reaction, and after adding water, the precipitated solid was filtered.

(3) To a solution of the resulted solid in dichloromethane (14.0 ml) was added trifluoroacetic acid (7.0 ml) at room temperature, and the mixture was stirred at room temperature for 1 hour. After the completion of reaction, and after adding water, the precipitated solid was filtered, and suspended and washed with ethanol to give the titled compound (1.42 g) as a white solid. MS(ESI) (m/z): 214 (M+H)$^+$.

Reference Example 15

1-(5-cyclopropylpyridin-2-yl)-5-methyl-1H-pyrazole-4-carboxylic acid (1) To ethanol (75 ml) were added 5-bromo-2-fluoropyridine (25.12 g) and hydrazine hydrate (100%) (91 g), and the mixture was stirred under refluxing for 4 hours, and then thereto was added water, and the resulted solid was washed with water to give 5-bromopyridin-2-ylhydrazine (25.3 g) as a white solid. MS(ESI) m/z: 188, 190 (M+H)$^+$.

(2) To a mixed solvent of 1N aqueous hydrochloric acid solution (320 ml) and ethanol (370 ml) were added 5-bromopyridin-2-ylhydrazine (25.3 g) and ethyl 2-ethoxymethylene acetoacetate (26.3 g) synthesized according to the method described in J. Chem. Soc. Perkin trans. I, p. 1875 (1988), and the mixture was stirred at reflux temperature for 4.5 hours, and then solvent was distilled away under reduced pressure. To the residue was added water, and the resulted solid was washed with water, and then recrystallized in a mixed solvent of ethyl acetate/n-hexane to give 1-(5-bromopyridin-2-yl)-5-methyl-1H-pyrazole-4-carboxylic acid ethyl ester (30.6 g) as a pale yellow solid. MS(ESI) m/z: 310, 312 (M+H)$^+$.

(3) A suspension of 1-(5-bromopyridin-2-yl)-5-methyl-1H-pyrazole-4-carboxylic acid ethyl ester (18 g), cyclopropylboronic acid (9.96 g), dichlorobis(tricyclohexylphosphine)-palladium (II) (2.14 g), and tripotassium phosphate (49.2 g) in 1,4-dioxane (120 ml) was stirred at 110° C. for 3 hours. After the completion of reaction, the mixture was let stand to be cooled, and thereto was added chloroform, and the mixture was filtered through Celite, and then to the filtrate was added saturated aqueous ammonium chloride solution, and the mixture was extracted with chloroform. The organic layer was dried over anhydrous sodium sulfate, and solvent was distilled away under reduced pressure. The resulted residue was purified by silica gel chromatography (n-hexane:ethyl acetate) to give 1-(5-cyclopropylpyridin-2- yl)-5-methyl-1H-pyrazole-4-carboxylic acid ethyl ester (14 g) as a yellow solid. MS(ESI) m/z: 272 (M+H)+.

(4) To a solution of 1-(5-cyclopropylpyridin-2-yl)-5-methyl-1H-pyrazole-4-carboxylic acid ethyl ester (14 g) in methanol (70 ml) and tetrahydrofuran (70 ml) were added 4N aqueous sodium hydroxide solution (70 ml) and water (50 ml), and the mixture was stirred at room temperature overnight. After the completion of reaction, the organic solvent was distilled away under reduced pressure, and then thereto were added water and diethyl ether, and the aqueous layer was separated. The aqueous layer was adjusted to be pH5 by the addition of concentrated hydrochloric acid under ice cooling, and the precipitated solid was filtered and ventilated to be dried with heat at 60° C. to give the titled compound (12.4 g) as a white solid. MS(ESI) m/z: 244 (M+H)+.

Structures of Reference example 1 to Reference example 15 are shown as follows.

Reference Example 16

1-(3,4-difluorophenyl)-5-methyl-1H-pyrazole-4-carboxylic acid

In Reference example 4, 3,4-difluorophenylhydrazine was used instead of 4-fluorophenylhydrazine hydrochloride to be reacted and treated in a similar manner to give the titled compound. MS(ESI) m/z: 239 (M+H)$^+$.

Reference Example 17

5-methyl-1-phenyl-1H-pyrazole-4-carboxylic acid

In Reference example 4, phenylhydrazine was used instead of 4-fluorophenylhydrazine hydrochloride to be reacted and treated in a similar manner to give the titled compound. MS(ESI) m/z: 203 (M+H)$^+$.

Reference Example 18

5-methyl-1-(pyridin-2-yl)-1H-pyrazole-4-carboxylic acid

To a solution of 1-(5-bromopyridin-2-yl)-5-methyl-1H-pyrazole-4-carboxylic acid (30 mg) described in Reference example 15 in N,N-dimethylformamide (1 ml) was added 10% palladium carbon (containing about 50% moisture) (10 mg) at room temperature, and the mixture was stirred under hydrogen at the same temperature for 30 minutes. After the completion of reaction, the reaction solution was filtered through Celite, and then solvent was distilled away under reduced pressure, and the resultant was concentrated by azeotropy with toluene solution to give the titled compound (23 mg) as a white solid. MS(ESI) m/z: 204 (M+H)$^+$.

Reference Example 19

1-(5-fluoropyridin-2-yl)-5-methyl-1H-pyrazole-4-carboxylic acid

In Reference example 1, 2,5-difluoropyridine was used instead of 2-chloro-5-(trifluoromethyl)pyridine to be reacted and treated in a similar manner to (1) and (2) to give the titled compound. MS(ESI) m/z: 222 (M+H)$^+$.

Reference Example 20

5-methyl-1-(5-methylpyridin-2-yl)-1H-pyrazole-4-carboxylic acid (1) A suspension of 1-(5-bromopyridin-2-yl)-5-methyl-1H-pyrazole-4-carboxylic acid ethyl ester (4 g) of Reference example 15(2), methylboronic acid (1.54 g), 1,1'-bis(di-tert-butylphosphino)ferrocene (306 mg), palladium acetate (145 mg) and tripotassium phosphate (11 g) in 1,4-dioxane (30 ml) was stirred with refluxing. After the completion of reaction, the mixture was let stand to be cooled, and thereto were added ice water and saturated aqueous ammonium chloride solution, and the mixture was extracted with ethyl acetate. The organic layer was dried over anhydrous sodium sulfate, and solvent was distilled away under reduced pressure. The resulted residue was purified by silica gel chromatography (n-hexane:ethyl acetate) to give 5-methyl-1-(5-methylpyridin-2-yl)-1H-pyrazole-4-carboxylic acid ethyl ester (2.81 g) as a white solid. MS(ESI) m/z: 246 (M+H)$^+$.

(2) In Reference example 15(4), 5-methyl-1-(5-methylpyridin-2-yl)-1H-pyrazole-4-carboxylic acid ethyl ester (2.81 g) was used instead of 1-(5-cyclopropylpyridin-2-yl)-5-methyl-1H-pyrazole-4-carboxylic acid ethyl ester to be reacted and treated in a similar manner to give the titled compound (2.19 g) as a white solid. MS(ESI) m/z: 218 (M+H)$^+$.

Reference Example 21

5-methyl-1-(4-methylphenyl)-1H-pyrazole-4-carboxylic acid amide

To a solution of 5-methyl-1-(4-methylphenyl)-1H-pyrazole-4-carboxylic acid (5.41 g) of Reference example 5 in dichloroethane (35 ml) were added thionyl chloride (3.57 g) and N,N-dimethylformamide (catalytic amount) at room temperature, and the mixture was stirred at 70° C., and then solvent and excess thionyl chloride were distilled away. To the resulted reaction mixture was added a solution of 7N ammonia in methanol (30 ml) under ice cooling, and the mixture was stirred at room temperature for 2 hours. After the completion of reaction, solvent and excess ammonia were distilled away to give the titled compound (3.53 g) as a solid. 1H-NMR (400 MHz, DMSO-d6) δ: 2.38 (3H, s), 2.47 (3H, s), 7.00 (1H, brs), 7.33-7.39 (4H, m), 7.54 (1H, brs), 8.06 (1H, s).

Reference Example 22

1-(4-chlorophenyl)-5-methyl-1H-pyrazole-4-carboxylic acid amide 1-(4-Chlorophenyl)-5-methyl-1H-pyrazole-4-carboxylic acid of Reference example 6 was used instead of 5-methyl-1-(4-methylphenyl)-1H-pyrazole-4-carboxylic acid of Reference example 21 to be reacted and treated in a similar manner to give the titled compound as a solid. $^1$H-NMR (400 MHz, DMSO-d$_6$) δ: 2.51 (3H, s), 7.07 (1H, brs), 7.54-7.76 (5H, m), 8.11 (1H, s).

Reference Example 23

1-(4-fluorophenyl)pyrrole-3-carboxylic acid (1) To acetic acid (120 ml) were added 4-fluoroaniline (117 g) and 2,5-dimethoxytetrahydrofuran (139 g), and the mixture was stirred at reflux temperature for 1 hour, and then the reaction solution was added to ice water (1 l). The precipitated solid was filtered and dissolved in methanol, and thereto was added water. Again, the precipitated solid was filtered to give 1-(4-fluorophenyl)pyrrole (122.7 g).

(2) To N,N-dimethylformamide (250 ml) containing 1-(4-fluorophenyl)pyrrole (136.5 g) was slowly added dropwise phosphorus oxychloride (136.3 g) under ice cooling so that temperature of the reaction solution did not extend beyond 50° C., and then the mixture was stirred at room temperature all night and all day. The reaction solution was added to aqueous potassium carbonate solution under ice cooling to be alkalized, and then extracted with ethyl acetate, washed with water, saturated saline, and solvent was distilled away under reduced pressure. To the residue was added n-hexane, and the precipitated solid was filtered to give 1-(4-fluorophenyl)-2-formylpyrrole (152 g).

(3) To a solution of 1-(4-fluorophenyl)-2-formylpyrrole (50.4 g) in dichloroethane (680 ml) was added dropwise trifluoromethanesulfonic acid (100 g) at room temperature, and then the mixture was stirred at reflux temperature for 13 hours. The reaction solution was added to ice water, and then the mixture was alkalized by the addition of potassium carbonate. The mixture was extracted with chloroform, and dried over anhydrous magnesium sulfate, and then solvent was distilled away under reduced pressure. The residue was purified by silica gel chromatography (n-hexane:ethyl acetate) to give 1-(4-fluorophenyl)-3-formylpyrrole (34.5 g).
(4) To potassium permanganate (28.7 g) were added N,N-dimethylformamide (300 ml) and water (100 ml), and thereto was added 1-(4-fluorophenyl)-3-formylpyrrole (34.4 g) under ice cooling, and then thereto was further added potassium permanganate (14.4 g), and the mixture was warmed to room temperature and stirred for 2 hours. To the reaction solution was added 1N aqueous sodium hydroxide solution (300 ml), and the mixture was stirred at room temperature for 0.5 hour, and then washed with ethyl acetate, neutralized by hydrochloric acid and extracted with ethyl acetate, and then solvent was distilled away under reduced pressure. To the residue was added isopropylether, and the precipitated solid was filtered to give the titled compound (15.2 g). MS(ESI) m/z: 205 (M+H)$^+$.

Reference Example 24

2-[4-(trifluoromethyl)phenyl]-1H-imidazole-4-carboxylic acid (1) To a solution of 4-(trifluoromethyl)benzonitrile (10 g) in ethanol (100 ml) was added 50% aqueous hydroxylamine solution (11.6 g), and the mixture was stirred at 80° C. overnight. After the completion of reaction, solvent was distilled away, and thereto was added water. The insoluble was filtered and then dried to give N-hydroxy-4-(trifluoromethyl)benzamidine (12.6 g). MS(ESI) m/z: 205 (M+H)$^+$.
(2) To a solution of N-hydroxy-4-(trifluoromethyl)benzamidine (3.0 g) in ethanol (30 ml) was added ethyl acetylenecarboxylate (1.44 g), and the mixture was stirred at 80° C. for 26 hours. Solvent was distilled away, and then thereto was added diphenylether (15 ml), and the mixture was stirred at 180° C. for additional 5.5 hours. After the completion of reaction, the mixture was let stand to be cooled to room temperature, and thereto was added n-hexane. The insoluble was filtered and washed with n-hexane, and then dried to give 2-[4-(trifluoromethyl)phenyl]-1H-imidazole-4-carboxylic acid ethyl ester (1.84 g). MS(ESI) m/z: 285 (M+H)$^+$.
(3) To a solution of 2-[4-(trifluoromethyl)phenyl]-1H-imidazole-4-carboxylic acid ethyl ester (300 mg) in methanol (4 ml) was added 1N aqueous sodium hydroxide solution (4 ml) at room temperature, and the mixture was stirred at 80° C. for 6.5 hours. After the completion of reaction, thereto was added 1N aqueous hydrochloric acid solution (4 ml), and solvent was distilled away. The resulted residue was washed with water, and dried under reduced pressure, and then the titled compound (141 mg) was obtained as a pale brown solid. MS(ESI) m/z: 257 (M+H)$^+$.

Reference Example 25

3-methyl-2-[4-(trifluoromethyl)phenyl]-3H-imidazole-4-carboxylic acid (1) To 2-bromo-3-methyl-3H-imidazole-4-carboxylic acid methyl ester (800 mg) were added 4-(trifluoromethyl)benzeneboronic acid (1.04 g) and tetrakis(triphenylphosphine)palladium (422 mg) and tetrahydrofuran (9 ml), saturated sodium carbonate water (3 ml) and water (1.5 ml) as solvent, and the mixture was stirred under microwave at 120° C. for 30 minutes. After the completion of reaction, to the reaction solution was added water, and the mixture was extracted with ethyl acetate. The organic layer was dried over anhydrous magnesium sulfate, and solvent was distilled away. The resulted residue was purified by silica gel column chromatography (n-hexane:ethyl acetate) to give 3-methyl-2-[4-(trifluoromethyl)phenyl]-3H-imidazole-4-carboxylic acid methyl ester (980 mg) as a yellow solid. MS(ESI) m/z: 285 (M+H)$^+$.
(2) To a solution of 3-methyl-2-[4-(trifluoromethyl)phenyl]-3H-imidazole-4-carboxylic acid methyl ester (962 mg) in tetrahydrofuran (10 ml) was added at room temperature 1N aqueous sodium hydroxide solution (10 ml), and the mixture was stirred at 80° C. for 1.5 hours. After the completion of reaction, thereto was added 1N aqueous hydrochloric acid solution (10 ml), and solvent was distilled away. The resulted residue was washed with water, and dried over under reduced pressure to give the titled compound (788 mg) as a gray solid. MS(ESI) m/z: 271 (M+H)$^+$.

Reference Example 26

5-methyl-1-[5-(trifluoromethyl)pyridin-2-yl]-1H-[1,2,3]triazole-4-carboxylic acid (1) To a solution of 2-chloro-5-(trifluoromethyl)pyridine (3.0 g) in dimethylsulfoxide (80 ml) was added sodium azide (1.61 g) at room temperature, and the mixture was stirred at 70° C. for 8.5 hours. After the completion of reaction, to the reaction solution was added ethyl acetate, and the mixture was washed with water and saturated aqueous sodium chloride solution. The organic layer was dried over anhydrous magnesium sulfate, and then solvent was distilled away to give a yellow solid (2.22 g).
(2) To a solution of the resulted solid (1.09 g) in ethanol (15 ml) were added 3-oxobutanoic acid ethyl ester (754 mg) and sodium ethoxide (1.18 g) at room temperature, and the mixture was stirred at 70° C. for 40 minutes. After the completion of reaction, to the reaction solution was added ethyl acetate, and the mixture was washed with water and saturated aqueous sodium chloride solution. The organic layer was dried over anhydrous magnesium sulfate, and then solvent was distilled away. The resulted residue was purified by silica gel column chromatography (hexane:ethyl acetate) to give 5-methyl-1-[5-(trifluoromethyl)pyridin-2-yl]-1H-[1,2,3]triazole-4-carboxylic acid ethyl ester (692 mg) as a white solid. MS(ESI) m/z: 301 (M+H)$^+$.
(3) To a solution of 5-methyl-1-[5-(trifluoromethyl)pyridin-2-yl]-1H-[1,2,3]triazole-4-carboxylic acid ethyl ester (681 mg) in tetrahydrofuran (10 ml) was added 1N aqueous sodium hydroxide solution (10 ml) at room temperature, and the mixture was stirred at 80° C. for 9 hours. After the completion of reaction, thereto was added 1N aqueous hydrochloric acid solution (10 ml), and solvent was distilled away. The resulted residue was washed with water, and dried under reduced pressure to give the titled compound (396 mg) as a brown solid. MS(ESI) m/z: 273 (M+H)$^+$.

Reference Example 27

2-(4-chlorophenyl)thiophene-4-carboxylic acid

A solution of 4-chlorophenylboronic acid (1.09 g), 2-bromothiophene-4-carboxylic acid (1.04 g), 1,1-bis(diphenylphosphino)ferrocene-palladium (II) dichloride-dichloromethane complex (204 mg) and cesium carbonate (2.28 g) in 1,2-dimethoxyethane (7.5 ml) and ethanol (7.5 ml) was stirred for 11 hours under heating and refluxing. After the completion of reaction, the reaction solution was concentrated, and thereto was added 1N aqueous hydrochloric acid solution, and the mixture was extracted with ethyl acetate. The organic layer was dried over magnesium sulfate, and then concentrated and suspended to be washed with diethyl ether to give a solid (0.74 g). The resulted solid was dissolved into 1N aqueous sodium hydroxide solution, and washed with ethyl acetate. The aqueous layer was acidified by 1N aqueous hydrochloric acid solution, and the precipitated solid was filtered and washed with water, then dried to give the titled compound (0.54 g) as a white solid. MS(ESI) m/z: 237 (M–H)⁻.

Reference Example 28

2-(4-chlorophenyl)thiazole-5-carboxylic acid (1) To a solution of 4-chlorophenylboronic acid (4.17 g), 2-bromothiazole-5-carboxylic acid methyl ester (4.93 g) and tripotassium phosphate•monohydrate (17.7 g) in 1,2-dimethoxyethane (140 ml) was added under nitrogen atmosphere 1,1-bis(diphenylphosphino)ferrocene-palladium (II) dichloride-dichloromethane complex (1.79 g), and the mixture was stirred under heating and refluxing for 7 hours. After the completion of reaction, the reaction solution was filtered through Celite and concentrated. The resulted residue was purified by silica gel column chromatography (n-hexane:ethyl acetate) to give a white solid (2.95 g).
(2) A solution of the resulted white solid (2.69 g) in 1N aqueous sodium hydroxide solution (32 ml) and methanol (106 ml) was stirred under heating and refluxing for 1.5 hours. After the completion of reaction, methanol in the reaction solution was distilled away under reduced pressure, and the resultant was acidified by the addition of 1N aqueous hydrochloric acid solution and extracted with ethyl acetate. The organic layer was dried over magnesium sulfate and concentrated to give the titled compound (2.52 g) as a white solid. MS(ESI) m/z: 240 (M+H)⁺.

Reference Example 29

2-(4-chlorophenyl)thiazole-4-carboxylic acid

A solution of 3-bromopyruvic acid (5.07 g) and 4-chlorothiobenzamide (5.21 g) in 1,4-dioxane (150 ml) was stirred under heating and refluxing for 2 hours. After the completion of reaction, the reaction solution was concentrated under reduced pressure, and thereto was added ice water, and the precipitated solid was filtered. The resulted solid was washed with water, and dried under reduced pressure to give the titled compound (7.2 g) as a pale brown solid. MS(ESI) m/z: 240 (M+H)⁺.

Reference Example 30

4-(4-chlorophenyl)thiazole-2-carboxylic acid (1) A solution of 4-chlorophenacyl bromide (8.91 g) and ethyl thiooxamate (5.08 g) in ethanol (60 ml) was stirred under heating and refluxing for 0.5 hour. After the completion of reaction, the reaction solution was ice cooled, and the precipitated solid was filtered and washed with diethyl ether to give a white solid (6.58 g).
(2) A solution of the resulted white solid (5.35 g) in 1N aqueous sodium hydroxide solution (60 ml) and ethanol (200 ml) was stirred under heating and refluxing for 0.5 hour. After the completion of reaction, ethanol in the reaction solution was distilled away under reduced pressure, and thereto was added water. Then, the mixture was acidified by the addition of aqueous hydrochloric acid solution, and the precipitated solid was filtered and washed with water. The resulted solid was dried under reduced pressure to give the titled compound (4.72 g) as a pale yellow solid. MS(ESI) m/z: 240 (M+H)⁺.

Reference Example 31

5-(4-chlorophenyl)thiazole-2-carboxylic acid (1) To a solution of 2-amino-4'-chloroacetophenone hydrochloride (1.19 g) and triethylamine (1.7 ml) in methylene chloride (12 ml) was added ethyloxalyl chloride (0.8 g) under ice cooling, and the mixture was stirred under ice cooling for 1 hour. After the completion of reaction, the reaction solution was extracted with methylene chloride, and the organic layer was dried over magnesium sulfate, and then concentrated. The resulted residue was purified by silica gel column chromatography (chloroform) to give a solid (1.42 g).
(2) To a solution of the resulted solid (1.42 g) in 1,4-dioxane (30 ml) was added Lawesson's reagent (2.13 g), and the mixture was stirred under heating and refluxing for 2 hours. After the completion of reaction, to the reaction solution was added ice water, and then the mixture was neutralized by the addition of saturated aqueous sodium carbonate solution. The mixture was extracted with ethyl acetate, and the organic layer was washed with saturated aqueous sodium chloride solution, dried over magnesium sulfate, and then concentrated. The resulted residue was purified by silica gel column chromatography (n-hexane:ethyl acetate) to give a white solid (1.14 g).
(3) A solution of the resulted white solid (1.10 g) in 1N aqueous sodium hydroxide solution (17 ml) and tetrahydrofuran (29 ml) was stirred at room temperature for 0.5 hour. After the completion of reaction, to the reaction was added 1N aqueous hydrochloric acid solution, and the mixture was extracted with ethyl acetate. The organic layer was dried over magnesium sulfate and concentrated to give the titled compound (0.98 g) as a white solid. MS(ESI) m/z: 240 (M+H)⁺.

Reference Example 32

2-(4-chlorophenyl)-2H-[1,2,3]triazole-4-carboxylic acid (1) A solution of 4-chlorophenylhydrazine (24.5 g) and D-glucose (30.92 g) in water (215 ml) and acetic acid (8.6 ml) was stirred at room temperature overnight. After the completion of reaction, the insoluble was filtered. The filtrate was extracted with ethyl acetate, and the organic layer was dried over magnesium sulfate and concentrated to give a solid. The resulted solid was mixed with the resulted insoluble filtered before and washed with methanol to give a solid (3.9 g).
(2) To the resulted solid (3.9 g) was added water (50 ml), and thereto was gradually added potassium permanganate (8.4 g) under heating and refluxing. After the completion of reaction, the reaction solution was filtered through Celite, and to the filtrate was added 1N aqueous hydrochloric acid solution, and the mixture was extracted with ethyl acetate. The organic layer was dried over sodium sulfate, and then concentrated to give the titled compound (0.1 g). MS(ESI) m/z: 222 (M−H)⁻.

The structures of Reference example 16 to Reference example 32 are shown below.

TABLE 2

| Ref. Ex. No | Structure |
|---|---|
| 16 | (3,4-difluorophenyl)-5-methyl-1H-pyrazole-4-carboxylic acid |
| 17 | 5-methyl-1-phenyl-1H-pyrazole-4-carboxylic acid |
| 18 | 5-methyl-1-(pyridin-2-yl)-1H-pyrazole-4-carboxylic acid |
| 19 | 1-(5-fluoropyridin-2-yl)-5-methyl-1H-pyrazole-4-carboxylic acid |
| 20 | 5-methyl-1-(5-methylpyridin-2-yl)-1H-pyrazole-4-carboxylic acid |
| 21 | 5-methyl-1-(4-methylphenyl)-1H-pyrazole-4-carboxamide |
| 22 | 1-(4-chlorophenyl)-5-methyl-1H-pyrazole-4-carboxamide |
| 23 | 1-(4-fluorophenyl)-1H-pyrrole-3-carboxylic acid |

TABLE 2-continued

| Ref. Ex. No | Structure |
|---|---|
| 24 | 2-(4-(trifluoromethyl)phenyl)-1H-imidazole-4-carboxylic acid |
| 25 | 1-methyl-2-(4-(trifluoromethyl)phenyl)-1H-imidazole-5-carboxylic acid |
| 26 | 5-methyl-1-(5-(trifluoromethyl)pyridin-2-yl)-1H-1,2,3-triazole-4-carboxylic acid |
| 27 | 5-(4-chlorophenyl)thiophene-3-carboxylic acid |
| 28 | 2-(4-chlorophenyl)thiazole-5-carboxylic acid |
| 29 | 2-(4-chlorophenyl)thiazole-4-carboxylic acid |
| 30 | 4-(4-chlorophenyl)thiazole-2-carboxylic acid |
| 31 | 5-(4-chlorophenyl)thiazole-2-carboxylic acid |
| 32 | 2-(4-chlorophenyl)-2H-1,2,3-triazole-4-carboxylic acid |
| blank | blank |

Example 1

N-[5-cyclopropyl-6-(4-hydroxypiperidin-1-yl)pyridin-3-yl]-5-methyl-1-[5-(trifluoromethyl)pyridin-2-yl]-1H-pyrazole-4-carboxamide

[Chemical formula 55]

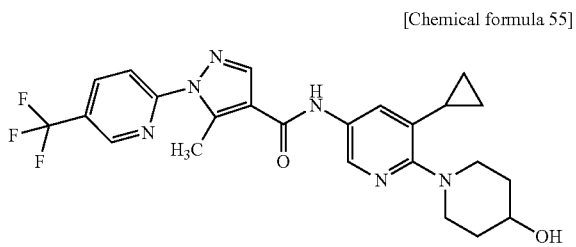 [SMILES: Cc1c(C(=O)Nc2cnc(N3CCC(O)CC3)c(C3CC3)c2)cnn1-c1ccc(C(F)(F)F)cn1]

(1) To a solution of 2,3-dichloro-5-nitropyridine (1.0 g) in N,N-dimethylformamide (5.1 ml) was added 4-hydroxypiperidine (1.05 g) at room temperature, and the mixture was stirred at 50° C. for 0.5 hour. After the completion of reaction, the mixture was cooled to room temperature, and thereto was added water, and then the precipitated solid was filtered. The resulted solid was suspended and washed with ethanol to give 1-(3-chloro-5-nitropyridin-2-yl)piperidin-4-ol (905 mg) as a yellow solid. MS(ESI) (m/z): 258 (M+H)$^+$.

(2) To a solution of 1-(3-chloro-5-nitropyridin-2-yl)piperidin-4-ol (905 mg) in pyridine (7.0 ml) was added benzoyl chloride (0.49 ml) under ice cooling, and the mixture was stirred at room temperature for 1.5 hours. After the completion of reaction, thereto was added water, and then the precipitated solid was filtered. The resulted solid was recrystallized in a mixed solvent of n-hexane/ethyl acetate. Then, the resulted solid was purified by silica gel column chromatography (n-hexane:ethyl acetate), and then the resulted solid was dissolved in ethyl acetate and washed with 1N aqueous sodium hydroxide solution and water, and the organic layer was dried over anhydrous sodium sulfate, and then solvent was distilled away to give benzoic acid [1-(3-chloro-5-nitropyridin-2-yl)piperidin-4-yl]ester (1.13 g) as a yellow solid. MS(ESI) (m/z): 362 (M+H)$^+$.

(3) To a solution of benzoic acid [1-(3-chloro-5-nitropyridin-2-yl)piperidin-4-yl]ester (1.13 g), cyclopropylboronic acid (350 mg), bis(tricyclohexylphosphine)palladium (II) dichloride (116 mg) and tripotassium phosphate (2.33 g) in toluene (12 ml) was added water (1.0 ml), and the mixture was stirred at 100° C. for 1 hour. After the completion of reaction, the mixture was cooled to room temperature, and thereto was added water, and then the mixture was extracted with ethyl acetate. The organic layer was washed with saturated aqueous sodium chloride solution and dried over anhydrous sodium sulfate, and then solvent was distilled away. The resulted residue was purified by silica gel column chromatography (n-hexane:ethyl acetate) to give benzoic acid [1-(3-cyclopropyl-5-nitropyridin-2-yl)piperidin-4-yl]ester (1.04 g) as a yellow solid. MS(ESI) (m/z): 368 (M+H)$^+$.

(4) To a solution of benzoic acid [1-(3-cyclopropyl-5-nitropyridin-2-yl)piperidin-4-yl]ester (1.04 g) in tetrahydrofuran (10 ml) and methanol (10 ml) was added 10% palladium carbon (209 mg), and the mixture was stirred under hydrogen gas flow at room temperature for 4 hours. After the completion of reaction, the mixture was filtered through Celite, and then solvent was distilled away. The resulted residue was purified by silica gel column chromatography (n-hexane:ethyl acetate) to give benzoic acid [1-(5-amino-3-cyclopropylpyridin-2-yl)piperidin-4-yl]ester (0.94 g) as a brown viscous body. MS(ESI) (m/z): 338 (M+H)$^+$.

(5) To a solution of benzoic acid [1-(5-amino-3-cyclopropylpyridin-2-yl)piperidin-4-yl]ester (150 mg) in pyridine (4.0 ml) was added 5-methyl-1-[5-(trifluoromethyl)pyridin-2-yl]-1H-pyrazole-4-carboxylic acid chloride (152 mg) of Reference example 1 at room temperature, and the mixture was stirred at 40° C. for 1 hour, and then the mixture was stirred at 60° C. for 0.5 hour. After the completion of reaction, the mixture was cooled to room temperature, and thereto was added water, and then the mixture was extracted with ethyl acetate. The organic layer was washed with saturated aqueous sodium chloride solution and dried over anhydrous sodium sulfate, and then solvent was distilled away. The resulted residue was recrystallized in a mixed solvent of ethanol/ethyl acetate to give benzoic acid [1-(3-cyclopropyl-5-{5-methyl-1-[5-(trifluoromethyl)pyridin-2-yl]-1H-pyrazole-4-carboxamide}pyridin-2-yl)piperidin-4-yl]ester (155 mg) as a yellow solid. MS(ESI) (m/z): 591 (M+H)$^+$.

(6) To a solution of benzoic acid [1-(3-cyclopropyl-5-{5-methyl-1-[5-(trifluoromethyl)pyridin-2-yl]-1H-pyrazole-4-carboxamide}pyridin-2-yl)piperidin-4-yl]ester (155 mg) in ethanol (3.0 ml) and 1,4-dioxane (3.0 ml) was added 1N aqueous sodium hydroxide solution (0.3 ml) at room temperature, and the mixture was stirred at 90° C. for 2 hours. After the completion of reaction, thereto was added water under ice cooling, and then the precipitated solid was filtered to give the titled compound (107 mg) as a white solid. MS(ESI) (m/z): 487 (M+H)$^+$.

Example 2

1-(3-chlorophenyl)-N-[6-(4-hydroxypiperidin-1-yl)-5-methylpyridin-3-yl]-5-methyl-1H-pyrazole-4-carboxamide

[Chemical formula 56]

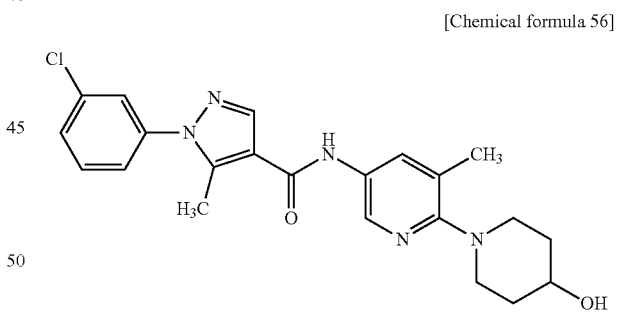

(1) To a solution of 2-chloro-3-methyl-5-nitropyridine (2.0 g) in N,N-dimethylformamide (4 ml) were added 4-piperidinol (1.42 g) and potassium carbonate (2.07 g), and the mixture was stirred for 2 hours with warming from 0° C. to 65° C. To the reaction solution was added water, and the precipitated yellow solid (2.77 g) was filtered.

(2) To a solution of the resulted yellow solid (2.75 g) in pyridine (12 ml) was added under ice cooling benzoyl chloride (1.80 g), and the mixture was stirred overnight with gradually warming from ice cooling to room temperature. To the reaction solution was added water, and the precipitated solid (4.0 g) was filtered.

(3) To a solution of the resulted solid (3.96 g) in tetrahydrofuran (30 ml) and methanol (15 ml) was added 10% palladium carbon (400 mg), and the mixture was stirred under hydrogen at room temperature for 2 hours. The reaction solution was filtered through Celite and concentrated, and then subjected to column chromatography to give a viscous body (3.6 g).

(4) To a solution of the resulted viscous body (374 mg) in pyridine (6 ml) was added acid chloride (337 mg) prepared from 1-(3-chlorophenyl)-5-methyl-1H-pyrazole-4-carboxylic acid of Reference example 9 in a similar manner to the method of Reference example 1(3) under ice cooling, and the mixture was stirred at the same temperature for 15 minutes. To the reaction solution was added triethylamine (1.2 equivalents), and the mixture was stirred at room temperature overnight. To the reaction solution was added water, and the mixture was extracted with ethyl acetate, and then concentrated. To the resulted residue were added ethanol (8 ml) and 1N aqueous sodium hydroxide solution (2 ml), and the mixture was stirred at 70° C. for 1 hour. To the reaction solution was added water, and the mixture was extracted with methylene chloride, dried over anhydrous sodium sulfate, and then concentrated. The resulted residue was purified by silica gel column chromatography (chloroform:methanol) to give the titled compound (351 mg) as a white solid. MS(ESI) m/z: 426 (M+H)$^+$.

Example 3

1-(5-chloropyridin-2-yl)-N-{6-[4-(2-methoxyethyl)piperidin-1-yl]-5-methylpyridin-3-yl}-5-methyl-1H-pyrazole-4-carboxamide

[Chemical formula 57]

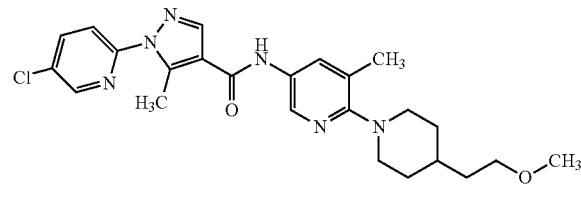

(1) To a solution of 2-chloro-3-methyl-5-nitropyridine (5.0 g) in N,N-dimethylformamide (29 ml) were added 4-piperidineethanol (3.74 g) and potassium carbonate (8.01 g) at room temperature, and the mixture was stirred at 80° C. for 8 hours. After the completion of reaction, the mixture was cooled to room temperature, and thereto was added water, and then the precipitated solid was filtered to give 2-[1-(3-methyl-5-nitropyridin-2-yl)piperidin-4-yl]ethanol (7.1 g) as a yellow solid. MS(ESI) (m/z): 266 (M+H)$^+$.

(2) To a solution of 2-[1-(3-methyl-5-nitropyridin-2-yl)piperidin-4-yl]ethanol (2.0 g) in N,N-dimethylformamide (15 ml) was added sodium hydride (362 mg) at room temperature, and the mixture was stirred at the same temperature for 0.5 hour. Then, thereto was added methyl iodide (1.41 ml), and the mixture was stirred at 80° C. for 1 hour, and then thereto was added additional methyl iodide (1.41 ml), and the mixture was stirred at 80° C. for 3 hours. After the completion of reaction, the mixture was cooled to room temperature, and then thereto was added water, and the mixture was extracted with ethyl acetate. The organic layer was dried over anhydrous sodium sulfate, and then solvent was distilled away.

(3) To a solution of the resulted solid (2.11 g) in tetrahydrofuran (30 ml) were added at room temperature palladium acetate (II) (169 mg) and an aqueous solution (7.5 ml) of potassium fluoride (1.75 g) and was gradually added dropwise poly(methylhydrosiloxane) (1.8 ml), and then the mixture was stirred at the same temperature for 1 hour. After the completion of reaction, thereto was added diethyl ether (30 ml), and the mixture was filtered through Celite, and then solvent was distilled away. To the resulted residue was added water, and the mixture was extracted with ethyl acetate. The organic layer was dried over anhydrous sodium sulfate, and then solvent was distilled away. The resulted residue was purified by silica gel column chromatography (chloroform:methanol) to give a brown viscous body (1.22 g).

(4) To a solution of 1-(5-chloropyridin-2-yl)-5-methyl-1H-pyrazole-4-carboxylic acid (476 mg) of Reference example 2 in toluene (10 ml) were added thionyl chloride (716 mg) and N,N-dimethylformamide (catalytic amount) at room temperature, and the mixture was stirred at 80° C. for 1 hour, and then solvent and excess thionyl chloride were distilled away. To the resulted reaction mixture was added pyridine (5.0 ml), and then thereto was added a solution of a viscous body (500 mg) obtained in (3) in pyridine (5.0 ml), and the mixture was stirred at 50° C. 1 hour. After the completion of reaction, thereto were added triethylamine (2.0 ml) and water, and the precipitated solid was filtered. The resulted solid was suspended and washed with ethanol to give the titled compound (463 mg) as a white solid. MS(ESI) m/z: 469 (M+H)$^+$.

Example 4

1-(5-chloropyridin-2-yl)-N-{6-[4-(1-hydroxymethyl)piperidin-1-yl]-5-methylpyridin-3-yl}-5-methyl-1H-pyrazole-4-carboxamide

[Chemical formula 58]

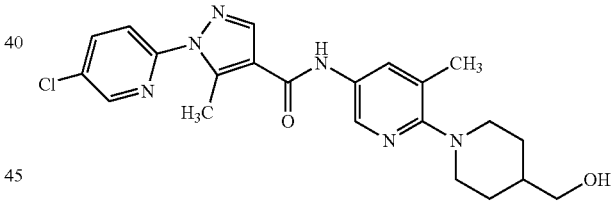

(1) To a solution of 2-chloro-3-methyl-5-nitropyridine (7.49 g) in N,N-dimethylformamide (43 ml) were added 4-piperidinemethanol (5.0 g) and potassium carbonate (12 g) at room temperature, and the mixture was stirred at 80° C. for 3 hours. After the completion of reaction, the mixture was cooled to room temperature, and thereto was added water, and then the precipitated solid was filtered to give a yellow solid (10.2 g).

(2) To a solution of the resulted solid (7.0 g) in pyridine (28 ml) was added acetic anhydride (14 ml) at room temperature, and the mixture was stirred at the same temperature for 3 hours. After the completion of reaction, thereto was added water, and then the precipitated solid was filtered.

(3) To a solution of the resulted solid (7.83 g) in tetrahydrofuran (110 ml) were added at room temperature palladium acetate (II) (599 mg) and an aqueous solution (27 ml) of potassium fluoride (6.2 g) and gradually added dropwise poly(methylhydrosiloxane) (6.38 ml), and then the mixture was stirred at the same temperature for 1 hour. After the completion of reaction, thereto was added diethyl ether (110 ml), and the mixture was filtered through Celite, and then solvent was distilled away. To the resulted residue was added water, and the mixture was extracted with ethyl acetate. The organic layer was dried over anhydrous sodium sulfate, and then solvent was distilled away. The resulted residue was purified by silica gel column chromatography (chloroform: methanol) to give a brown solid (6.39 g).

(4) To a solution of 1-(5-chloropyridin-2-yl)-5-methyl-1H-pyrazole-4-carboxylic acid (226 mg) of Reference example 2 in toluene (5 ml) were added thionyl chloride (339 mg) and N,N-dimethylformamide (catalytic amount) at room temperature, and the mixture was stirred at 80° C. for 1 hour, and then solvent and excess thionyl chloride were distilled away. To the resulted reaction mixture was added pyridine (5.0 ml), then a solution of a solid (250 mg) obtained in (3) in pyridine (5.0 ml), and the mixture was stirred at 50° C. for 1 hour. After the completion of reaction, thereto were added triethylamine (2.0 ml) and water, and the precipitated solid was filtered. The resulted solid was purified by silica gel column chromatography (chloroform:methanol) to give acetic acid [(1-{5-[1-(5-chloropyridin-2-yl)-5-methyl-1H-pyrazole-4-carboxamide]-3-methylpyridin-2-yl}piperidin-4-yl)methyl]ester (337 mg) as a pale red solid. MS(ESI) m/z: 483 (M+H)$^+$.

(5) To a solution of acetic acid [(1-{5-[1-(5-chloropyridin-2-yl)-5-methyl-1H-pyrazole-4-carboxamide]-3-methylpyridin-2-yl}piperidin-4-yl)methyl]ester (290 mg) in ethanol (6.0 ml) and tetrahydrofuran (3.0 ml) was added 1N aqueous sodium hydroxide solution (1.8 ml) at room temperature, and the mixture was stirred at 50° C. for 0.5 hour. After the completion of reaction, the mixture was cooled to room temperature, and thereto was added water, and then the precipitated solid was filtered to give the titled compound (231 mg) as a white solid. MS(ESI) (m/z): 441 (M+H)$^+$.

Example 5

N-[5-cyano-6-(4-hydroxypiperidin-1-yl)pyridin-3-yl]-1-(4-methoxyphenyl)-5-methyl-1H-pyrazole-4-carboxamide

[Chemical formula 59]

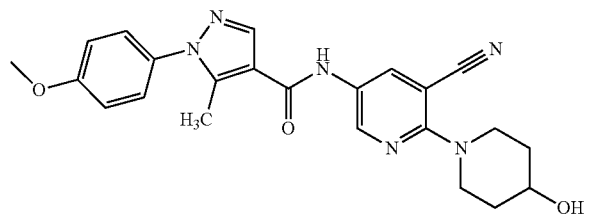

(1) To 2-chloro-3-cyanopyridine (120 g) was added 3N aqueous hydrochloric acid solution (1.74 l), and the mixture was refluxed for 10 hours. After the completion of reaction, the mixture was stirred under ice cooling for 1 hour, and thereto was added water, and the solid was filtered.

(2) To the resulted solid was added concentrated sulfuric acid (900 ml), and then was added concentrated nitric acid (95.4 g) under ice cooling, and the mixture was stirred at room temperature for 25 hours. After the completion of reaction, the reaction solution was added to ice water, and solid was filtered and washed with water, and then dried to give a solid (80.35 g).

(3) To the resulted solid (15 g) was added phenylphosphoryl dichloride (60 ml), and the mixture was stirred at 170° C. for 4 hours. After the completion of reaction, the mixture was cooled to room temperature, and the reaction solution was added to 0.5N aqueous sodium hydroxide solution (600 ml), and the mixture was stirred at room temperature for 0.5 hour, and solid was filtered. To the resulted solid were added water (30 ml) and saturated sodium bicarbonate water (30 ml), and the mixture was stirred at room temperature for 0.25 hour, and solid was filtered, and then dried to give a solid (10.57 g).

(4) To a solution of the resulted solid (1.84 g) in N,N-dimethylformamide (20 ml) was added 4-hydroxypiperidine (2.43 g) at room temperature, and the mixture was stirred at 50° C. for 1 hour. After the completion of reaction, the mixture was cooled to room temperature, and thereto was added water, and then the mixture was extracted with ethyl acetate. The organic layer was washed with water, dried over anhydrous sodium sulfate, and then solvent was distilled away. The resulted residue was suspended and washed with a mixed solvent of ethyl acetate/diisopropylether to give 1-(3-cyano-5-nitropyridin-2-yl)piperidin-4-ol (1.9 g) as a yellow solid. $^1$H-NMR (400 MHz, DMSO-d$_6$) δ: 1.53-1.46 (2H, m), 1.86-1.89 (2H, m), 3.63-3.68 (2H, m), 3.71-3.85 (1H, m), 4.20-4.27 (2H, m), 4.88 (1H, d, J=5.6 Hz), 8.80 (1H, d, J=3.6 Hz), 9.09 (1H, d, J=3.6 Hz).

(5) To a solution of 1-(3-cyano-5-nitropyridin-2-yl)piperidin-4-ol (3.25 g) in pyridine (16 ml) was added benzoyl chloride (2.02 g) under ice cooling, and the mixture was stirred at room temperature for 2 hours. After the completion of reaction, thereto was added water, and then the precipitated solid was filtered to give a yellow solid (4.65 g).

(6) To a solution of the resulted solid (4.61 g) in tetrahydrofuran (50 ml) and methanol (10 ml) was added 10% palladium carbon (200 mg), and the mixture was stirred under hydrogen gas flow at room temperature for 2 hours. After the completion of reaction, the mixture was filtered through Celite, and then solvent was distilled away. The resulted residue was purified by silica gel column chromatography (n-hexane:ethyl acetate) to give a solid (4.0 g).

(7) The reaction mixture (276 mg) obtained by reacting and treating using 1-(4-methoxyphenyl)-5-methyl-1H-pyrazole-4-carboxylic acid of Reference example 11 instead of 5-methyl-1-[5-(trifluoromethyl)pyridin-2-yl]-1H-pyrazole-4-carboxylic acid in a similar manner to Reference example 1(3) was added to a solution of a solid (323 mg) obtained in (6) in pyridine under ice cooling, and the mixture was stirred at the same temperature for 0.25 hour, and then thereto was added triethylamine (122 mg), and the mixture was stirred at room temperature for 2 hours. After the completion of reaction, the mixture was subjected to aftertreatment, and the resulted residue was purified by silica gel column chromatography to give a solid (500 mg).

(8) To a solution of the resulted solid (500 mg) in ethanol (8.0 ml) was added 1N aqueous sodium hydroxide solution (2.0 ml) at room temperature, and the mixture was stirred at 55° C. for 1.5 hours. After the completion of reaction, the mixture was cooled to room temperature, and thereto was added water, and then the precipitated solid was filtered. The resulted solid was suspended and washed with ethanol to give the titled compound (352 mg) as a white solid. MS(ESI) (m/z): 433 (M+H)$^+$.

Example 6 acetic acid [(1-{3-methyl-5-[5-methyl-1-(4-methylphenyl)-1H-pyrazole-4-carboxamide]pyridin-2-yl}piperidin-4-yl)methyl]ester

[Chemical formula 60]

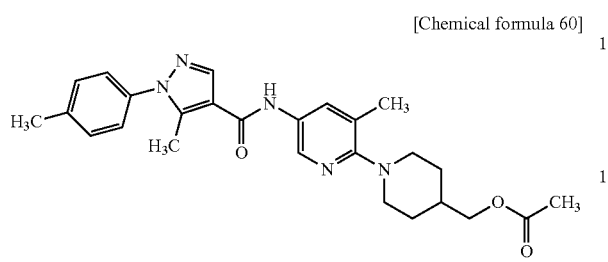

In Example 4(4), 5-methyl-1-(4-methylphenyl)-1H-pyrazole-4-carboxylic acid (205 mg) of Reference example 5 was used instead of 1-(5-chloropyridin-2-yl)-5-methyl-1H-pyrazole-4-carboxylic acid to be reacted and treated in a similar manner to give the titled compound (241 mg) as a pale red color. MS(ESI) m/z: 462 (M+H)$^+$.

Example 7

1-(4-chlorophenyl)-N-[5-cyano-6-(1,4-dioxa-8-azaspiro[4,5]dec-8-yl)pyridin-3-yl]-5-methyl-1H-pyrazole-4-carboxamide

[Chemical formula 61]

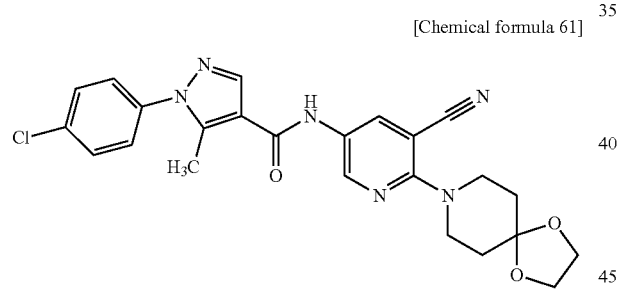

(1) To a solution of 5-bromo-2-chloro nicotinic acid nitrile (6.52 g) in N,N-dimethylformamide (30 ml) were added 1,4-dioxa-8-azaspiro[4,5]decane (5.0 g) and potassium carbonate (4.83 g) at room temperature, and the mixture was stirred at 80° C. for 1.5 hours. After the completion of reaction, the mixture was cooled to room temperature, and thereto was added water, and then the mixture was filtered to give a solid (9.65 g).

(2) A solution of 1-(4-chlorophenyl)-5-methyl-1H-pyrazole-4-carboxylic acid amide (389 mg) of Reference example 22, the solid obtained in (1) (487 mg), copper iodide (22 mg), N,N'-dimethylethylenediamine (20 mg) and potassium carbonate (415 mg) in 1,4-dioxane (2.0 ml) was stirred at 110° C. for 7 hours. After the completion of reaction, the mixture was cooled to room temperature, and thereto was added water, and the mixture was extracted with dichloromethane. The organic layer was dried over anhydrous sodium sulfate, and then solvent was distilled away. The resulted residue was purified by silica gel column chromatography (chloroform:methanol), and the resulted solid was suspended and washed with ethanol to give the titled compound (197 mg) as a solid. MS(ESI) m/z: 479 (M+H)$^+$.

Example 8

N-[5-cyano-6-(4-hydroxypiperidin-1-yl)pyridin-3-yl]-5-methyl-1-(4-methylphenyl)-1H-pyrazole-4-carboxamide

[Chemical formula 62]

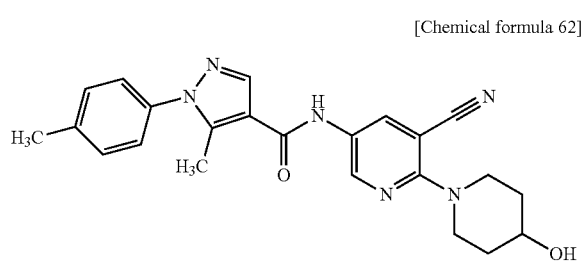 [SMILES: Cc1ccc(-n2ncc(C(=O)Nc3cnc(N4CCC(O)CC4)c(C#N)c3)c2C)cc1]

(1) To a solution of 5-bromo-2-chloro nicotinic acid nitrile (6.52 g) in N,N-dimethylformamide (40 ml) were added 4-piperidinol (3.64 g) and potassium carbonate (4.14 g) at room temperature, and the mixture was stirred at 70° C. for 2 hours. After the completion of reaction, the mixture was cooled to room temperature, and thereto was added water, and then the mixture was extracted with ethyl acetate. The organic layer was washed with water, and then dried over anhydrous sodium sulfate, and then solvent was distilled away to give an oil.

(2) A solution of 5-methyl-1-(4-methylphenyl)-1H-pyrazole-4-carboxylic acid amide (237 mg) of Reference example 21, the oil obtained in (1) (283 mg), copper iodide (10 mg), N,N'-dimethylethylenediamine (9 mg) and potassium carbonate (277 mg) in 1,4-dioxane (1.5 ml) was stirred at 110° C. for 8 hours. After the completion of reaction, the mixture was cooled to room temperature, and the precipitated solid was filtered. The resulted solid was purified by silica gel column chromatography (chloroform:methanol), and the resulted solid was suspended and washed with ethanol to give the titled compound (256 mg) as a pale yellow solid. MS(ESI) m/z: 417 (M+H)$^+$.

Example 9

N-[5-cyclopropyl-6-(4-hydroxypiperidin-1-yl)pyridin-3-yl]-1-(2,4-dichlorophenyl)-5-methyl-1H-pyrazole-4-carboxamide

[Chemical formula 63]

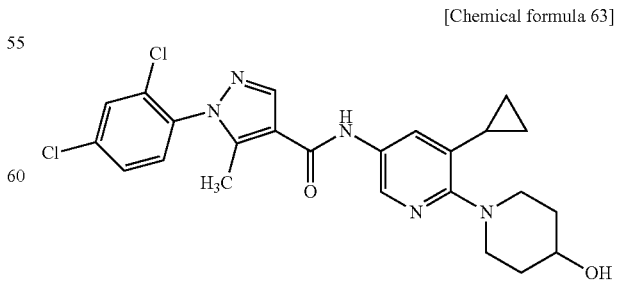

To a solution of 1-(2,4-dichlorophenyl)-5-methyl-1H-pyrazole-4-carboxylic acid (181 mg) of Reference example 7 in toluene (5 ml) were added thionyl chloride (185 mg) and N,N-dimethylformamide (catalytic amount) at room temperature, and the mixture was stirred at 80° C. for 1 hour, and then solvent and excess thionyl chloride were distilled away. To the resulted reaction mixture was added pyridine (2.5 ml), and then thereto was added a solution of benzoic acid [1-(5-amino-3-cyclopropylpyridin-2-yl)piperidin-4-yl]ester (150 mg) obtained in Example 1(4) in pyridine (2.5 ml), and the mixture was stirred at 60° C. for 0.5 hour. After the completion of reaction, thereto were added triethylamine (5.0 ml) and water, and the mixture was extracted with ethyl acetate. The organic layer was dried over anhydrous sodium sulfate, and then solvent was distilled away. The resulted residue was purified by silica gel column chromatography (n-hexane:ethyl acetate). To a solution of the resulted solid in ethanol (10 ml) and 1,4-dioxane (10 ml) was added 1N sodium hydroxide at room temperature, and the mixture was stirred at 90° C. for 1 hour. After the completion of reaction, thereto was added water, and then the precipitated solid was filtered. The resulted solid was recrystallized by ethanol/water to give the titled compound (45 mg) as a white solid. MS(ESI) m/z: 486 (M+H)$^+$.

Example 10

1-(4-chlorophenyl)-N-[5-cyano-6-(4-cyanopiperidin-1-yl)pyridin-3-yl]-5-methyl-1H-pyrazole-4-carboxamide

[Chemical formula 64]

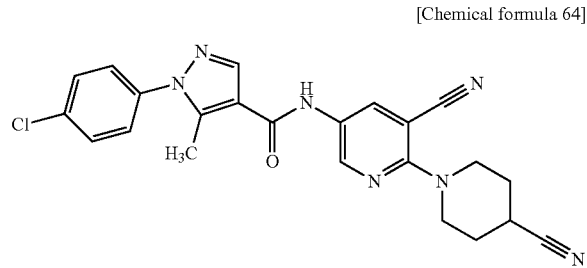 [SMILES: Cc1c(C(=O)Nc2cnc(N3CCC(C#N)CC3)c(C#N)c2)cnn1-c1ccc(Cl)cc1]

(1) To a suspension of 4-cyanopiperidine hydrochloride (587 mg) and potassium carbonate (1.1 g) in N,N-dimethylformamide was added 2-chloro-5-nitronicotinic acid nitrile (609 mg) under ice cooling, and the mixture was stirred at 60° C. After the completion of reaction, the mixture was cooled to room temperature, and thereto was added water, and then the precipitated solid was filtered.
(2) To a solution of the resulted solid in tetrahydrofuran (14 ml) and methanol (7.0 ml) was added 10% palladium carbon, and the mixture was stirred under hydrogen gas flow at room temperature for 1.5 hours. After the completion of reaction, the mixture was filtered through Celite, and then solvent was distilled away. The resulted residue was purified by silica gel column chromatography to give 1-(5-amino-3-cyanopyridin-2-yl)-4-cyanopiperidine (710 mg). $^1$H-NMR (400 MHz, DMSO-d$_6$) δ: 1.81-1.84 (2H, m), 1.95-1.99 (2H, m), 3.05-3.10 (3H, m), 3.11-3.33 (2H, m), 5.30 (2H, brs), 7.24 (1H, d, J=4.0 Hz), 7.89 (1H, d, J=4.0 Hz).
(3) The reaction mixture (281 mg) obtained by reacting and treating in a similar manner to Reference example 1(3) using 1-(4-chlorophenyl)-5-methyl-1H-pyrazole-4-carboxylic acid of Reference example 6 instead of 5-methyl-1-[5-(trifluoromethyl)pyridin-2-yl]-1H-pyrazole-4-carboxylic acid was added under ice cooling to a solution of 1-(5-amino-3-cyanopyridin-2-yl)-4-cyanopiperidine (228 mg) in pyridine, and the mixture was stirred at the same temperature for 0.25 hour, and then thereto was added triethylamine, and the mixture was stirred at room temperature for 2 hours. After the completion of reaction, thereto was added water, and the precipitated solid was filtered, and then suspended and washed to give the titled compound (425 mg) as a white solid. MS(ESI) m/z: 446 (M+H)$^+$.

Example 11 acetic acid [2-(1-{5-[1-(4-chlorophenyl)-5-(trifluoromethyl)-1H-pyrazole-4-carboxamide]-3-cyanopyridin-2-yl}piperidin-4-yl)ethyl]ester

[Chemical formula 65]

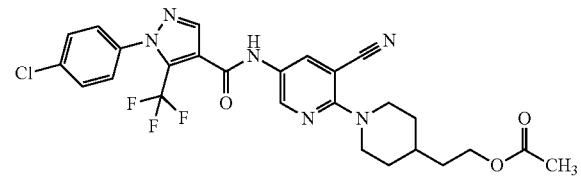

(1) To a solution of 4-piperidineethanol (3.1 g) and potassium carbonate (3.3 g) in N,N-dimethylformamide (20 ml) was added under ice cooling 2-chloro-5-nitronicotinic acid nitrile (3.7 g), and the mixture was stirred at 55° C. for 1.5 hours. After the completion of reaction, the mixture was cooled to room temperature, and thereto was added water, and then the precipitated solid was filtered.
(2) To a solution of the resulted solid in pyridine (30 ml) was added acetic anhydride (1.63 ml) at room temperature, and the mixture was stirred at the same temperature. After the completion of reaction, thereto was added water, and then the precipitated solid was filtered.
(3) To a solution of the resulted solid in 1,4-dioxane (30 ml) and methanol (20 ml) was added 10% palladium carbon at room temperature, and the mixture was stirred under hydrogen gas flow at room temperature for 2 hours. After the completion of reaction, the mixture was filtered through Celite, and solvent was distilled away, and then the resultant was suspended and washed with methanol to give a solid (4.91 g).
(4) The reaction mixture (408 mg) obtained by reacting and treating in a similar manner to Reference example 1(3) using 1-(4-chlorophenyl)-5-(trifluoromethyl)-1H-pyrazole-4-carboxylic acid of Reference example 8 instead of 5-methyl-1-[5-(trifluoromethyl)pyridin-2-yl]-1H-pyrazole-4-carboxylic acid was added under ice cooling to a solution of the solid obtained in (3) (346 mg) in pyridine (6.0 ml), and the mixture was stirred at the same temperature for 0.25 hour, and then thereto was added triethylamine, and the mixture was stirred at room temperature for 2 hours. After the completion of reaction, thereto was added water, and the precipitated solid was filtered, and then suspended and washed to give the titled compound (489 mg) as a solid. MS(ESI) m/z: 561 (M+H)$^+$.

Example 12

1-(3,5-dichloropyridin-2-yl)-N-{6-[4-(1-methoxymethyl)piperidin-1-yl]-5-methylpyridin-3-yl}-5-methyl-1H-pyrazole-4-carboxamide

[Chemical formula 66]

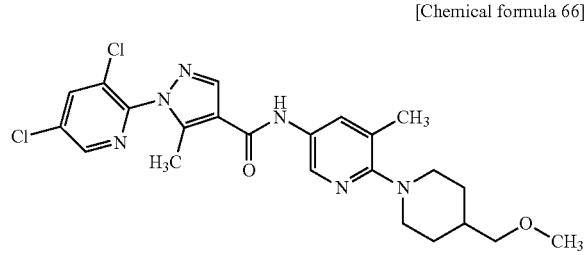 [SMILES: COCC1CCN(c2ncc(NC(=O)c3cnn(-c4ncc(Cl)cc4Cl)c3C)cc2C)CC1]

(1) To a solution of 2-chloro-3-methyl-5-nitropyridine (7.49 g) in N,N-dimethylformamide (43 ml) were added 4-piperidinemethanol (5.0 g) and potassium carbonate (12 g) at room temperature, and the mixture was stirred at 80° C. for 3 hours. After the completion of reaction, the mixture was cooled to room temperature, and thereto was added water, and then the precipitated solid was filtered to give a yellow solid (10.2 g).
(2) To a solution of the resulted solid (4.1 g) in N,N-dimethylformamide (16 ml) was added sodium hydride (783 mg) at room temperature, and the mixture was stirred at the same temperature for 0.5 hour. Then, thereto was added methyl iodide (3.1 ml), and the mixture was stirred at 80° C. for 1 hour, and then thereto was added additional methyl iodide (3.1 ml), and the mixture was stirred at 80° C. for 3 hours. After the completion of reaction, the mixture was cooled to room temperature, and thereto was added water, and the mixture was filtered to give a solid (4.33 g).
(3) To a solution of the resulted solid (4.33 g) in tetrahydrofuran (65 ml) were added at room temperature palladium acetate (II) (366 mg) and an aqueous solution (16 ml) of potassium fluoride (3.79 g), and then gradually added dropwise poly(methylhydrosiloxane) (3.9 ml), and then the mixture was stirred at the same temperature for 1 hour. After the completion of reaction, thereto was added diethyl ether (65 ml), and the mixture was filtered through Celite, and then solvent was distilled away. To the resulted residue was added water, and the mixture was extracted with ethyl acetate. The organic layer was dried over anhydrous sodium sulfate, and then solvent was distilled away. The resulted residue was purified by silica gel column chromatography (chloroform:methanol) to give a brown viscous body (2.27 g).
(4) To a solution of 1-(3,5-dichloropyridin-2-yl)-5-methyl-1H-pyrazole-4-carboxylic acid (256 mg) of Reference example 3 in toluene (5.0 ml) were added thionyl chloride (336 mg) and N,N-dimethylformamide (catalytic amount) at room temperature, and the mixture was stirred at 80° C. for 1 hour, and then solvent and excess thionyl chloride were distilled away. To the resulted reaction mixture was added pyridine (5.0 ml), and then thereto was added a solution of a viscous body (250 mg) obtained in (3) in pyridine (5.0 ml), and the mixture was stirred at 50° C. for 1 hour. After the completion of reaction, thereto were added triethylamine (2.0 ml) and water, and then the mixture was extracted with chloroform. The organic layer was dried over anhydrous sodium sulfate, and then solvent was distilled away. The resulted residue was purified by silica gel column chromatography (chloroform:methanol) to give the titled compound (394 mg) as a white solid. MS(ESI) m/z: 489 (M+H)+.

Example 13

N-[5-cyano-6-(4-cyanopiperidin-1-yl)pyridin-3-yl]-5-methyl-1-[4-(trifluoromethyl)phenyl]-1H-pyrazole-4-carboxamide

[Chemical formula 67]

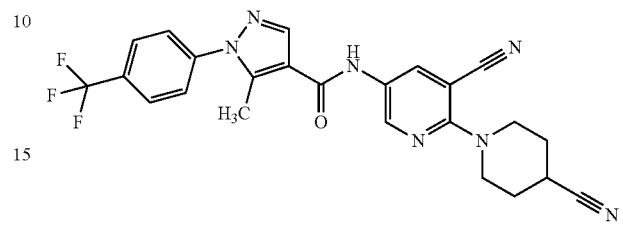

In Example 10, 5-methyl-1-[4-(trifluoromethyl)phenyl]-1H-pyrazole-4-carboxylic acid of Reference example 10 was used instead of 1-(4-chlorophenyl)-5-methyl-1H-pyrazole-4-carboxylic acid to be reacted and treated in a similar manner to give the titled compound as a solid. MS(ESI) m/z: 480 (M+H)+.

Example 14

N-{6-[4-(1-methoxymethyl)piperidin-1-yl]-5-methylpyridin-3-yl}-5-methyl-1-[5-(trifluoromethyl)pyridin-2-yl]-1H-pyrazole-4-carboxamide

[Chemical formula 68]

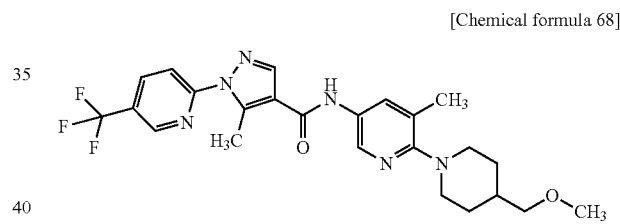

In Example 12, 5-methyl-1-[5-(trifluoromethyl)pyridin-2-yl]-1H-pyrazole-4-carboxylic acid (255 mg) of Reference example 1(2) was used instead of 1-(3,5-dichloropyridin-2-yl)-5-methyl-1H-pyrazole-4-carboxylic acid to be reacted and treated in a similar manner to give the titled compound (391 mg) as a white solid. MS(ESI) m/z: 489 (M+H)+.

Example 15

N-[6-(4-hydroxypiperidin-1-yl)-5-methylpyridin-3-yl]-5-methyl-1-[4-(trifluoromethyl)phenyl]-1H-pyrazole-4-carboxamide

[Chemical formula 69]

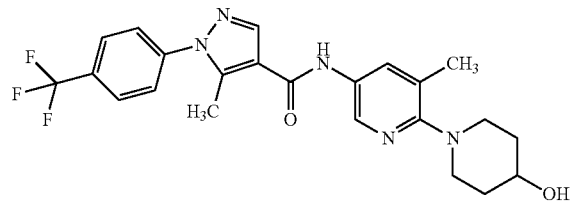

To a solution of a viscous body (410 mg) obtained in Example 2(3) in pyridine (6 ml) was added under ice cooling acid chloride (418 mg) which was prepared from 5-methyl-1-[4-(trifluoromethyl)phenyl]-1H-pyrazole-4-carboxylic acid described in Reference example 10 in the similar manner to the method described in Reference example 1(3), and the mixture was stirred at the same temperature for 15 minutes. To the reaction solution was added triethylamine (1.2 equivalents), and the mixture was stirred at room temperature for 2 hours. To the reaction solution was added water, and the precipitated solid was filtered and washed with ethanol. To the resulted solid were added ethanol (8 ml), 1N aqueous sodium hydroxide solution (2.6 ml) and tetrahydrofuran (4 ml), and the mixture was stirred at 60° C. for 1.5 hours. Under the reduced pressure, ethanol and tetrahydrofuran in the reaction solution were distilled away, and the resultant was extracted with ethyl acetate, and then the organic layer was concentrated. The resulted residue was washed with ethanol to give the titled compound (444 mg) as a white solid. MS(ESI) m/z: 460 (M+H)$^+$.

Example 16

1-(4-chlorophenyl)-N-[6-(4-methoxypiperidin-1-yl)-5-methylpyridin-3-yl]-5-methyl-1H-pyrazole-4-carboxamide

[Chemical formula 70]

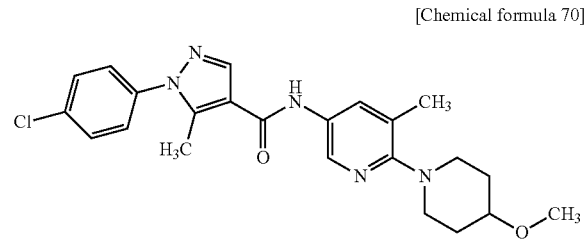 [SMILES: COC1CCN(c2ncc(NC(=O)c3cnn(-c4ccc(Cl)cc4)c3C)cc2C)CC1]

(1) 2-Bromo-3-methyl-5-nitropyridine (10 g), 4-hydroxypiperidine (5.6 g) and potassium carbonate (6.4 g) were added to N,N-dimethylformamide (30 ml), and the mixture was stirred at 70° C. for 3 hours, and then the reaction solution was treated with water, and the organic layer was extracted with ethyl acetate, dried over anhydrous magnesium sulfate, and then solvent was distilled away under reduced pressure to give 1-(3-methyl-5-nitropyridin-2-yl)piperidin-4-ol (1.10 g). MS(ESI) m/z: 238 (M+H)$^+$.
(2) 1-(3-Methyl-5-nitropyridin-2-yl)piperidin-4-ol (1.10 g) was added to tetrahydrofuran (10 ml) to give a solution, and thereto was added 30% potassium hydride (0.62 g), and the mixture was stirred for 30 minutes. Then, thereto was added methyl iodide (0.79 g) under ice cooling, and the mixture was stirred at the same temperature for 1 hour. The reaction solution was treated with water, and the organic layer was extracted with ethyl acetate, dried over anhydrous magnesium sulfate, and then solvent was distilled away under reduced pressure. The residue was separated and purified by silica gel column chromatography (ethyl acetate:n-hexane) to give 2-(4-methoxypiperidin-1-yl)-3-methyl-5-nitropyridine (190 mg). MS(ESI) m/z: 252 (M+H)$^+$.
(3) 2-(4-Methoxypiperidin-1-yl)-3-methyl-5-nitropyridine (190 mg), ferric (III) chloride (100 mg), and activated carbon (300 mg) were added to methanol (5 ml), and thereto was added 80% aqueous hydrazine (100 mg) under refluxed solvent, and the mixture was stirred for 3 hours. The reaction solution was filtered through Celite, the filtrate was concentrated, and the residue was recrystallized from aqueous methanol to give a brown solid (100 mg).
(4) 1-(4-Chlorophenyl)-5-methyl-1H-pyrazole-4-carboxylic acid (107 mg) of Reference example 6 was added to toluene (2 ml), and thereto was further added thionyl chloride (100 mg), and the mixture was stirred at 60° C. for 2 hours, and then solvent was distilled away under reduced pressure. To the residue was added a solution of the brown solid obtained in (3) (100 mg) in pyridine (10 ml), and the mixture was stirred at 40° C. for 2 hours. The reaction solution was treated with triethylamine and water, and the organic layer was extracted with ethyl acetate, dried over anhydrous magnesium sulfate, and then solvent was distilled away under reduced pressure. The residue was separated and purified by column chromatography (chloroform:methanol) to give the titled compound (90 mg) as a pale yellow solid. MS(ESI) m/z: 440 (M+H)$^+$.

Example 17 acetic acid {[1-(3-methyl-5-{5-methyl-1-[5-(trifluoromethyl)pyridin-2-yl]-1H-pyrazole-4-carboxamide}pyridin-2-yl)piperidin-4-yl]methyl}ester

[Chemical formula 71]

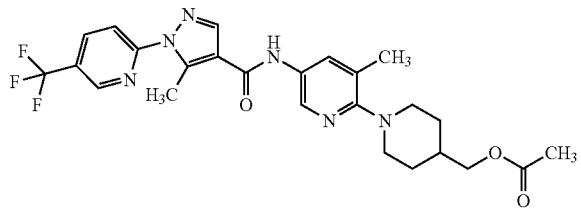

In Example 4(4), 5-methyl-1-[5-(trifluoromethyl)pyridin-2-yl]-1H-pyrazole-4-carboxylic acid (257 mg) of Reference example 1(2) was used instead of 1-(5-chloropyridin-2-yl)-5-methyl-1H-pyrazole-4-carboxylic acid to be reacted and treated in the similar manner to give the titled compound (430 mg) as a white solid. MS(ESI) m/z: 517 (M+H)$^+$.

Example 18

N-{5-cyclopropyl-6-[4-(2-hydroxyethyl)piperidin-1-yl]pyridin-3-yl}-1-(4-fluorophenyl)-5-methyl-1H-pyrazole-4-carboxamide

[Chemical formula 72]

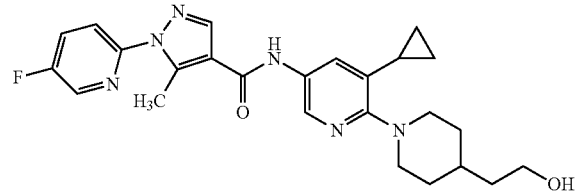

(1) To a solution of 3-bromo-2-chloro-5-nitropyridine (4.75 g) in N,N-dimethylformamide (15 ml) were added 4-piperidineethanol (3.1 g) and potassium carbonate (3.3 g), and the mixture was stirred with warming temperature from 0° C. to 60° C. To the reaction solution was added water, and the precipitated solid was filtered (6.7 g).

(2) To a solution of the resulted solid (6.6 g) in methylene chloride (50 ml) and triethylamine (2.43 g) was added benzoyl chloride (3.09 g) under ice cooling, and the mixture was stirred under ice cooling for 2 hours. The reaction solution was concentrated under reduced pressure, and thereto was added water, and solid was filtered. Thereto was added ethanol (30 ml), and the mixture was suspended and washed under heating to give a solid (8.2 g).

(3) To a solution of the resulted solid (4.35 g) in water (3 ml) and toluene (36 ml) were added cyclopropylboronic acid (1.12 g), tripotassium phosphate (7.43 g) and dichlorobis (tricyclohexylphosphine)palladium (II) (369 mg), and the mixture was stirred at 98° C. for 3 hours. To the reaction solution was added water, and the mixture was extracted with ethyl acetate and concentrated. The resulted residue was purified by silica gel column chromatography (n-hexane:ethyl acetate) to give a solid (3.29 g).

(4) To a solution of the resulted solid (3.25 g) in tetrahydrofuran (15 ml) and methanol (15 ml) was added 10% palladium carbon (500 mg), and the mixture was stirred under hydrogen at room temperature for 3 hours. The reaction solution was filtered through Celite and concentrated, and then purified by column chromatography to give a viscous body (2.85 g).

(5) To a solution of the resulted viscous body (400 mg) in pyridine (6 ml) was added acid chloride (286 mg) which was prepared from 1-(4-fluorophenyl)-5-methyl-1H-pyrazole-4-carboxylic acid of Reference example 4 in the similar manner to the method of Reference example 1(3) under ice cooling, and the mixture was stirred for 15 minutes at the same temperature. To the reaction solution was added triethylamine (1.2 equivalents), and the mixture was stirred for 2 hours with gradually warming temperature from 0° C. to room temperature. To the reaction solution was added water, and the precipitated solid was filtered and washed with ethanol. To the resulted residue were added ethanol (8 ml) and 1N aqueous sodium hydroxide solution (1 ml), and the mixture was stirred at 65° C. for 1 hour. To the reaction solution was added water, and the precipitated solid was filtered. The resulted solid was recrystallized from ethanol to give the titled compound (246 mg) as a solid. MS(ESI) m/z: 464 (M+H)$^+$.

Example 19 acetic acid (1-{5-[1-(4-chlorophenyl)-5-methyl-1H-pyrazole-4-carboxamide]-3-cyanopyridin-2-yl}piperidin-4-yl)ester

[Chemical formula 73]

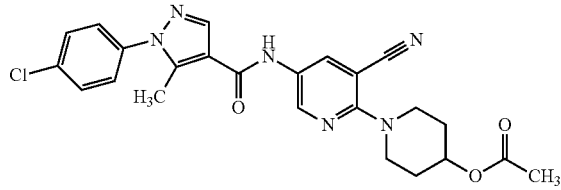

(1) To a solution of 4-piperidinol (2.43 g) in N,N-dimethylformamide (20 ml) was added 2-chloro-5-nitronicotinic acid nitrile (1.84 g) under ice cooling, and the mixture was stirred at 50° C. for 1 hour. After the completion of reaction, the mixture was cooled to room temperature, and thereto was added water, and then the mixture was extracted with ethyl acetate. The organic layer was washed with water, dried over anhydrous sodium sulfate, and then solvent was distilled away. The resulted residue was suspended and washed with a mixed solvent of ethyl acetate/diisopropylether to give a pale yellow solid (1.9 g).

(2) To a solution of the resulted solid (1.9 g) in dichloromethane (30 ml) were added triethylamine (1.22 ml), acetic anhydride (0.66 ml) and 4-dimethylaminopyridine (catalytic amount) under ice cooling, and the mixture was stirred at room temperature overnight. Then, thereto were added triethylamine (1.22 ml) and acetic anhydride (0.66 ml), and the mixture was stirred at the same temperature for 4 hours. After the completion of reaction, thereto was added water, and then the mixture was extracted with chloroform. The organic layer was washed with water, dried over anhydrous sodium sulfate, and then solvent was distilled away. The resulted residue was purified by silica gel column chromatography (chloroform:methanol) to give a yellow solid (1.48 g).

(3) To a solution of the resulted solid (1.4 g) in tetrahydrofuran (15 ml) and ethanol (5.0 ml) was added 10% palladium carbon (150 mg) at room temperature, and the mixture was stirred under hydrogen gas flow at room temperature for 2 hours. After the completion of reaction, the mixture was filtered through Celite, and then solvent was distilled away.

(4) A reaction mixture (561 mg) which was obtained by reacting and treating in the similar manner to Reference example 1(3) by using 1-(4-chlorophenyl)-5-methyl-1H-pyrazole-4-carboxylic acid of Reference example 6 instead of 5-methyl-1-[5-(trifluoromethyl)pyridin-2-yl]-1H-pyrazole-4-carboxylic acid was added to a solution of the resulted residue obtained in (3) in dichloromethane (15 ml) under ice cooling, and the mixture was stirred at the same temperature for 0.25 hours, and then thereto was added triethylamine, and the mixture was stirred at room temperature for 2 hours. After the completion of reaction, thereto was added water, and the precipitated solid was filtered. The resulted solid was purified by silica gel column chromatography (chloroform:methanol), and then suspended and washed with ethanol to give the titled compound (876 mg) as a white solid. MS(ESI) m/z: 479 (M+H)$^+$.

Example 20

1-(4-chlorophenyl)-N-{5-cyano-6-[4-(2-hydroxyethyl)piperidin-1-yl]pyridin-3-yl}-5-(trifluoromethyl)-1H-pyrazole-4-carboxamide

[Chemical formula 74]

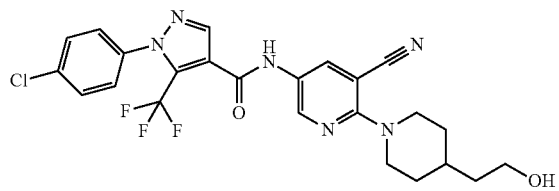

Acetic acid [2-(1-{5-[1-(4-chlorophenyl)-5-(trifluoromethyl)-1H-pyrazole-4-carboxamide]-3-cyanopyridin-2-yl}piperidin-4-yl)ethyl]ester (450 mg) of Example 11 was used instead of acetic acid [(1-{5-[1-(5-chloropyridin-2-yl)-5-methyl-1H-pyrazole-4-carboxamide]-3-methylpyridin-2-yl}piperidin-4-yl)methyl]ester in Example 4(5) to be reacted and treated in the similar manner to give the titled compound (416 mg) as a solid. MS(ESI) m/z: 519 (M+H)$^+$.

Example 21

1-(4-chlorophenyl)-N-{6-[4-(1-methoxymethyl)piperidin-1-yl]-5-methylpyridin-3-yl}-5-methyl-1H-pyrazole-4-carboxamide

[Chemical formula 75]

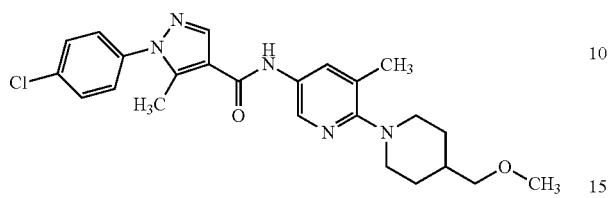

1-(4-Chlorophenyl)-5-methyl-1H-pyrazole-4-carboxylic acid (223 mg) of Reference example 6 was used instead of 1-(3,5-dichloropyridin-2-yl)-5-methyl-1H-pyrazole-4-carboxylic acid in Example 12 to be reacted and treated in the similar manner to give the titled compound (386 mg) as a white solid. MS(ESI) m/z: 454 (M+H)$^+$.

Example 22

1-(4-chlorophenyl)-N-{5-cyano-6-[4-(2-hydroxyethyl)piperidin-1-yl]pyridin-3-yl}-5-cyclopropyl-1H-pyrazole-4-carboxamide

[Chemical formula 76]

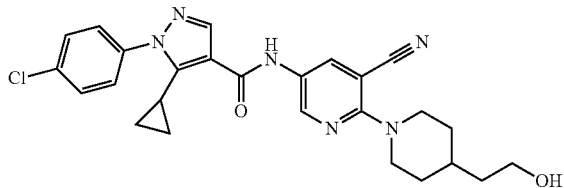

1-(4-Chlorophenyl)-5-cyclopropyl-1H-pyrazole-4-carboxylic acid (309 mg) of Reference example 12 was used instead of 1-(4-chlorophenyl)-5-(trifluoromethyl)-1H-pyrazole-4-carboxylic acid in Example 11(4) to be reacted and treated in the similar manner to Example 11(4) and Example 20 to give the titled compound (440 mg) as a white solid. MS(ESI) m/z: 491 (M+H)$^+$.

Example 23

1-(4-tert-butylphenyl)-N-[5-cyano-6-(4-hydroxypiperidin-1-yl)pyridin-3-yl]-5-methyl-1H-pyrazole-4-carboxamide

[Chemical formula 77]

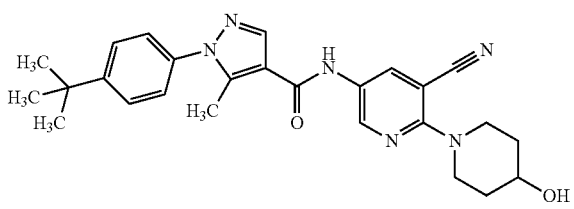

1-(4-tert-Butylphenyl)-5-methyl-1H-pyrazole-4-carboxylic acid (377 mg) of Reference example 13 was used instead of 1-(4-methoxyphenyl)-5-methyl-1H-pyrazole-4-carboxylic acid of Example 5 to be reacted and treated in a similar manner to give the titled compound (429 mg) as a solid. MS(ESI) m/z: 458 (M+H)$^+$.

Example 24

1-(5-cyanopyridin-2-yl)-N-{6-[4-(1-fluoro-1-methylethyl)piperidin-1-yl]-5-methylpyridin-3-yl}-1H-pyrrole-3-carboxamide

[Chemical formula 78]

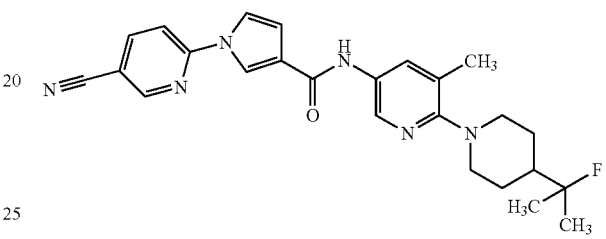

(1) To a solution of 2-chloro-3-methyl-5-nitropyridine (6.02 g) in N,N-dimethylformamide (35 ml) were added 2-(4-piperidinyl)-2-propanol (5.0 g) and potassium carbonate (9.65 g) at room temperature, and the mixture was stirred at 80° C. for 6 hours. After the completion of reaction, the mixture was cooled to room temperature, and thereto was added water, and then the precipitated solid was filtered to give a yellow solid (9.09 g).

(2) To a solution of the resulted solid (5.46 g) in dichloromethane (40 ml) was added dropwise under ice cooling diethylaminosulfur trifluoride (3.47 g), and the mixture was stirred at the same temperature for 0.5 hour. After the completion of reaction, to the mixture was slowly added dropwise 1N aqueous sodium hydroxide solution, and then the mixture was extracted with chloroform. The organic layer was dried over anhydrous sodium sulfate, and then solvent was distilled away. To a solution of the resulted residue in tetrahydrofuran (80 ml) were added an aqueous solution (20 ml) of palladium acetate (II) (439 mg) and potassium fluoride (4.54 g) at room temperature, and thereto was slowly added dropwise poly(methylhydrosiloxane) (4.7 ml), and then the mixture was stirred at the same temperature for 2 hours. After the completion of reaction, to the mixture was added diethyl ether (80 ml), and the mixture was filtered through Celite, and then solvent was distilled away. To the resulted residue was added water, and the mixture was extracted with ethyl acetate. The organic layer was dried over anhydrous sodium sulfate, and then solvent was distilled away. The resulted residue was purified by silica gel column chromatography (chloroform:methanol) to give a white solid (3.42 g).

(3) To a solution of 1-(5-cyanopyridin-2-yl)-1H-pyrrole-3-carboxylic acid (200 mg) of Reference example 14 in toluene (5 ml) were added thionyl chloride (335 mg) and N,N-dimethylformamide (catalytic amount) at room temperature, and the mixture was stirred at 80° C. for 1 hour, and then solvent and excess thionyl chloride were distilled away. To the resulted reaction mixture was added pyridine (5.0 ml), and then thereto was added a solution of the solid (236 mg) obtained in (2) in pyridine (5.0 ml), and the mixture was stirred at 50° C. for 1 hour. After the completion of reaction, to the mixture were added triethylamine (2.0 ml) and water, and the precipitated solid was filtered. The resulted solid was suspended and washed with ethanol to give the titled compound (289 mg) as a white solid. MS(ESI) m/z: 447 (M+H)+.

Example 25 acetic acid [2-(1-{3-cyano-5-[1-(4-fluorophenyl)-5-methyl-1H-pyrazole-4-carboxamide]pyridin-2-yl}piperidin-4-yl)ethyl]ester

[Chemical formula 79]

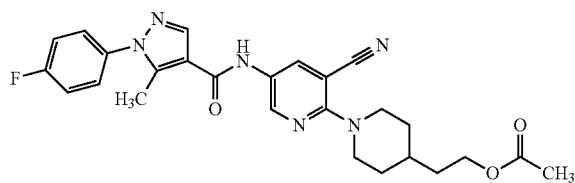

In Example 11(4), 1-(4-fluorophenyl)-5-methyl-1H-pyrazole-4-carboxylic acid (315 mg) of Reference example 4 was used instead of 1-(4-chlorophenyl)-5-(trifluoromethyl)-1H-pyrazole-4-carboxylic acid to be reacted and treated in a similar manner to give the titled compound (544 mg) as a solid. MS(ESI) m/z: 491 (M+H)+.

Example 26

N-{6-[4-(2-hydroxy-2-methylpropyl)piperidin-1-yl]-5-methylpyridin-3-yl}-5-methyl-1-(pyridin-2-yl)-1H-pyrazole-4-carboxamide

[Chemical formula 80]

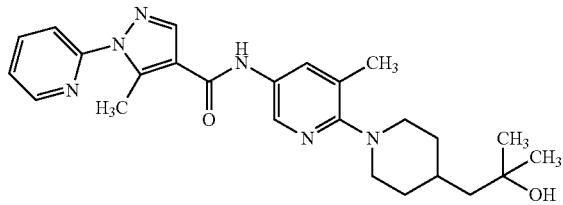

(1) To a solution of 2-bromo-3-methyl-5-nitropyridine (3.17 g) in N,N-dimethylformamide (15 ml) were added 4-piperidineethyl acetate (2.5 g) and potassium carbonate (4.04 g) at room temperature, and the mixture was stirred at 80° C. for 6 hours. After the completion of reaction, the mixture was cooled to room temperature, and then thereto was added water, and then the precipitated solid was filtered to give a yellow solid (3.31 g).
(2) To a solution of the resulted solid (3.31 g) in tetrahydrofuran (50 ml) was added an aqueous solution (20 ml) of palladium acetate (II) (484 mg) and potassium fluoride (2.5 g) at room temperature, and thereto was slowly added dropwise poly(methylhydrosiloxane) (2.6 ml), and then the mixture was stirred at the same temperature for 1 hour. After the completion of reaction, to the mixture was added diethyl ether (50 ml), and the mixture was filtered through Celite, and then solvent was distilled away. To the resulted residue was added water, and the mixture was extracted with ethyl acetate. The organic layer was dried over anhydrous sodium sulfate, and then solvent was distilled away. The resulted residue was purified by silica gel column chromatography (chloroform:methanol) to give a viscous body.
(3) To a solution of the resulted viscous body in pyridine (10 ml) was added acetic anhydride (5.0 ml) at room temperature, and the mixture was stirred at the same temperature for 3 hours. After the completion of reaction, to the mixture was added water, and then the precipitated solid was filtered. To a solution of the resulted solid in tetrahydrofuran (20 ml) was added dropwise a 1.06M solution of methylmagnesium bromide in tetrahydrofuran (41 ml) at 80° C., and the mixture was stirred at the same temperature for 3 hours. After the completion of reaction, the mixture was cooled to room temperature, and thereto was added saturated aqueous solution of ammonium chloride, and then the mixture was extracted with ethyl acetate. The organic layer was dried over anhydrous sodium sulfate, and then solvent was distilled away.
(4) To a solution of the resulted residue in methanol (165 ml) and tetrahydrofuran (55 ml) were added water (110 ml) and lithium hydroxide (45.2 g) at room temperature, and the mixture was stirred at 90° C. for 5 hours. After the completion of reaction, the mixture was cooled to room temperature, and solvent was distilled away, and then the resultant was extracted with chloroform. The organic layer was dried over anhydrous sodium sulfate, and then solvent was distilled away. The resulted residue was purified by silica gel column chromatography (chloroform:methanol) to give 1-[1-(5-amino-3-methylpyridin-2-yl)piperidin-4-yl]-2-methylpropan-2-ol as a white solid. MS(ESI) m/z: 264 (M+H)+.
(5) To a solution of 5-methyl-1-(pyridin-2-yl)-1H-pyrazole-4-carboxylic acid (150 mg) of Reference example 18 in toluene (7.5 ml) were added thionyl chloride (239 mg) and N,N-dimethylformamide (catalytic amount) at room temperature, and the mixture was stirred at 80° C. for 1 hour, and then solvent and excess thionyl chloride were distilled away. To the resulted reaction mixture was added pyridine (3.5 ml), and then thereto was added a solution of 1-[1-(5-amino-3-methylpyridin-2-yl)piperidin-4-yl]-2-methylpropan-2-ol (177 mg) in pyridine (4.0 ml), and the mixture was stirred at 50° C. for 1 hour. After the completion of reaction, to the mixture were added triethylamine (2.0 ml) and water, and the precipitated solid was filtered. Purification by silica gel column chromatography (chloroform:methanol) gave the titled compound (224 mg) as a white solid. MS(ESI) m/z: 449 (M+H)+.

Example 27

1-(3,4-difluorophenyl)-N-{6-[4-(1-hydroxyethyl)piperidin-1-yl]-5-methylpyridin-3-yl}-5-methyl-1H-pyrazole-4-carboxamide

[Chemical formula 81]

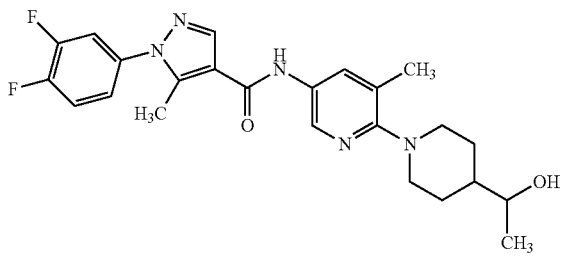

(1) To a solution of 1-Boc-4-piperidinealdehyde (1.87 g) in tetrahydrofuran (18 ml) was added dropwise a 1.06M solution of methylmagnesium bromide in tetrahydrofuran (9.6 ml) at −78° C., and the mixture was stirred at room temperature for 0.5 hour. After the completion of reaction, the mixture was cooled to room temperature, and thereto was added a saturated aqueous solution of ammonium chloride, and then the mixture was extracted with ethyl acetate. The organic layer was dried over anhydrous sodium sulfate, and then solvent was distilled away. To a solution of the resulted residue in ethyl acetate (18 ml) was added 4N hydrochloric acid/ethyl acetate solution (18 ml) at room temperature, and the mixture was stirred at the same temperature for 4 hours. After the completion of reaction, excess hydrochloric acid and solvent were distilled away. To a solution of the resulted residue in N,N-dimethylformamide (9.0 ml) were further added 2-bromo-3-methyl-5-nitropyridine (1.9 g) and potassium carbonate (1.94 g) at room temperature, and the mixture was stirred at 80° C. for 4 hours. After the completion of reaction, the mixture was cooled to room temperature, and thereto was added water, and then the mixture was extracted with ethyl acetate. The organic layer was dried over anhydrous sodium sulfate, and then solvent was distilled away.

(2) To a solution of the resulted residue in pyridine (11.2 ml) was added acetic anhydride (5.6 ml) at room temperature, and the mixture was stirred at the same temperature for 1 hour, and then stirred at 50° C. for 2 hours. After the completion of reaction, the mixture was cooled to room temperature, and thereto was added water, and then the mixture was extracted with ethyl acetate. The organic layer was dried over anhydrous sodium sulfate, and then solvent was distilled away. Then, to a solution of the resulted residue in tetrahydrofuran (28 ml) was added an aqueous solution (5.4 ml) of palladium acetate (II) (124 mg) and potassium fluoride (640 mg) at room temperature, and thereto was slowly added dropwise poly(methylhydrosiloxane) (0.7 ml), and then the mixture was stirred at the same temperature for 1 hour. After the completion of reaction, to the mixture was added diethyl ether (28 ml), and the mixture was filtered through Celite, and then solvent was distilled away. To the resulted residue was added water, and the mixture was extracted with ethyl acetate. The organic layer was dried over anhydrous sodium sulfate, and then solvent was distilled away. The resulted residue was purified by silica gel column chromatography (chloroform:methanol) to give a brown viscous body.

(3) To a solution of 1-(3,4-difluorophenyl)-5-methyl-1H-pyrazole-4-carboxylic acid (170 mg) of Reference example 16 in toluene (7.0 ml) were added thionyl chloride (231 mg) and N,N-dimethylformamide (catalytic amount) at room temperature, and the mixture was stirred at 80° C. for 1 hour, and then solvent and excess thionyl chloride were distilled away. To the resulted reaction mixture was added pyridine (3.5 ml), and then thereto was added a solution of the viscous body (180 mg) obtained in (2) in pyridine (3.5 ml), and the mixture was stirred at 50° C. for 1 hour. After the completion of reaction, to the mixture were added triethylamine (2.0 ml) and water, and the precipitated solid was filtered.

(4) To a solution of the resulted solid in ethanol (6.5 ml) and tetrahydrofuran (6.5 ml) was added 1N aqueous sodium hydroxide solution (13 ml) at room temperature, and the mixture was stirred at 50° C. for 1 hour. After the completion of reaction, the mixture was cooled to room temperature, and thereto was added water, and then the precipitated solid was filtered. The resulted solid was purified by a basic silica gel column chromatography (n-hexane:ethyl acetate) to give the titled compound (137 mg) as a white solid. MS(ESI) m/z: 456 (M+H)⁺.

Example 28

1-(4-fluorophenyl)-N-{6-[4-(1-hydroxyethyl)piperidin-1-yl]-5-methylpyridin-3-yl}-5-methyl-1H-pyrazole-4-carboxamide

[Chemical formula 82]

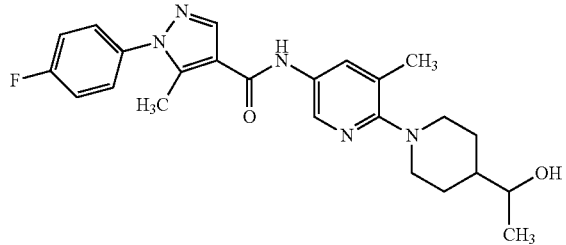

In Example 27, 1-(4-fluorophenyl)-5-methyl-1H-pyrazole-4-carboxylic acid (166 mg) of Reference example 4 was used instead of 1-(3,4-difluorophenyl)-5-methyl-1H-pyrazole-4-carboxylic acid to be reacted and treated in a similar manner to give the titled compound (109 mg) as a white solid. MS(ESI) m/z: 438 (M+H)⁺.

Example 29

1-(4-chlorophenyl)-N-[5-cyano-6-(4-oxopiperidin-1-yl)pyridin-3-yl]-5-methyl-1H-pyrazole-4-carboxamide

[Chemical formula 83]

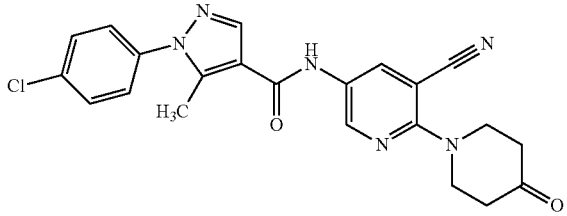

To 1-(4-chlorophenyl)-N-[5-cyano-6-(1,4-dioxa-8-azaspiro[4,5]dec-8-yl)pyridin-3-yl]-5-methyl-1H-pyrazole-4-carboxamide (400 mg) of Example 7 were added acetic acid (6.0 ml) and 1N aqueous hydrochloric acid solution (1.5 ml) at room temperature, and the mixture was stirred at 75° C. for 1 hour. After the completion of reaction, the mixture was cooled to room temperature, and thereto were added 1N sodium hydroxide and water, and the precipitated solid was filtered. The resulted solid was purified by silica gel column chromatography (chloroform:methanol), and then suspended and washed with ethyl acetate to give the titled compound (268 mg) as a solid. MS(ESI) m/z: 435 (M+H)⁺.

Example 30

N-{5-cyano-6-[4-(2-hydroxyethyl)piperidin-1-yl]pyridin-3-yl}-1-(4-fluorophenyl)-5-methyl-1H-pyrazole-4-carboxamide

[Chemical formula 84]

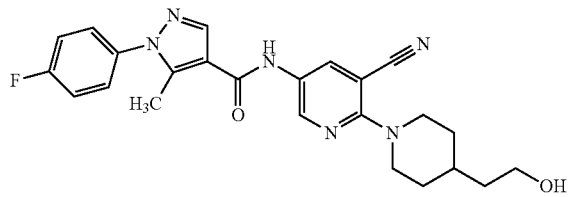

In Example 4(5), acetic acid [2-(1-{3-cyano-5-[1-(4-fluorophenyl)-5-methyl-1H-pyrazole-4-carboxamide]pyridin-2-yl}piperidin-4-yl)ethyl]ester (491 mg) of Example 25 was used instead of acetic acid [(1-{5-[1-(5-chloropyridin-2-yl)-5-methyl-1H-pyrazole-4-carboxamide]-3-methylpyridin-2-yl}piperidin-4-yl)methyl]ester to be reacted and treated in a similar manner to give the titled compound (395 mg) as a solid. MS(ESI) m/z: 449 (M+H)$^+$.

Example 31

N-({6-[4-(2-methoxyethyl)piperidin-1-yl]-5-methylpyridin-3-yl}-5-methyl-1-[5-(trifluoromethyl)pyridin-2-yl]-1H-pyrazole-4-carboxamide

[Chemical formula 85]

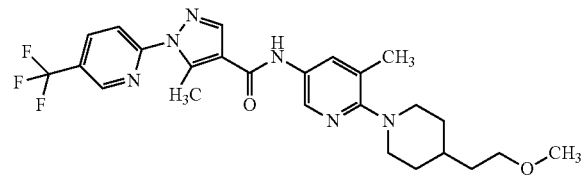

In Example 3, 5-methyl-1-[5-(trifluoromethyl)pyridin-2-yl]-1H-pyrazole-4-carboxylic acid (544 mg) of Reference example 1(2) was used instead of 1-(5-chloropyridin-2-yl)-5-methyl-1H-pyrazole-4-carboxylic acid to be reacted and treated in a similar manner to give the titled compound (507 mg) as a white solid. MS(ESI) m/z: 503 (M+H)$^+$.

Example 32

N-{6-[4-(1-fluoro-1-methylethyl)piperidin-1-yl]-5-methylpyridin-3-yl}-5-methyl-1-(4-methylphenyl)-1H-pyrazole-4-carboxamide

[Chemical formula 86]

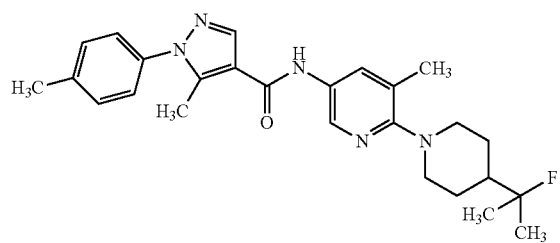

In Example 24, 5-methyl-1-(4-methylphenyl)-1H-pyrazole-4-carboxylic acid (172 mg) of Reference example 5 was used instead of 1-(5-cyanopyridin-2-yl)-1H-pyrrole-3-carboxylic acid to be reacted and treated in a similar manner to give the titled compound (315 mg) as a white solid. MS(ESI) m/z: 450 (M+H)$^+$.

Example 33

N-{6-[4-(1-methoxymethyl)piperidin-1-yl]-5-methylpyridin-3-yl}-5-methyl-1-[4-(trifluoromethyl)phenyl]-1H-pyrazole-4-carboxamide

[Chemical formula 87]

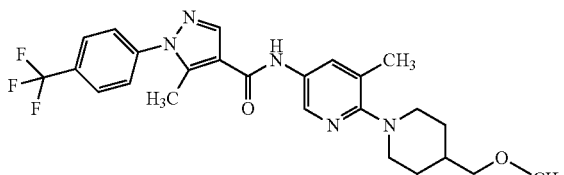

In Example 12, 5-methyl-1-[4-(trifluoromethyl)phenyl]-1H-pyrazole-4-carboxylic acid (255 mg) of Reference example 10 was used instead of 1-(3,5-dichloropyridin-2-yl)-5-methyl-1H-pyrazole-4-carboxylic acid to be reacted and treated in a similar manner to give the titled compound (423 mg) as a white solid. MS(ESI) m/z: 488 (M+H)$^+$.

Example 34

N-{6-[4-(1-fluoro-1-methylethyl)piperidin-1-yl]-5-methylpyridin-3-yl}-1-(4-fluorophenyl)-5-methyl-1H-pyrazole-4-carboxamide

[Chemical formula 88]

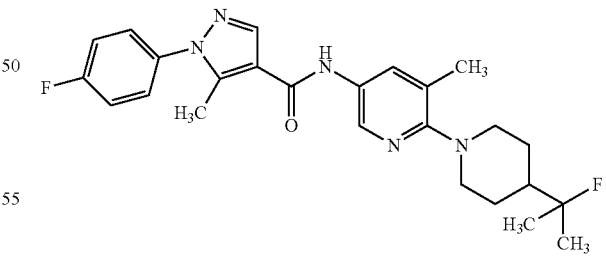

In Example 24, 1-(4-fluorophenyl)-5-methyl-1H-pyrazole-4-carboxylic acid (175 mg) of Reference example 4 was used instead of 1-(5-cyanopyridin-2-yl)-1H-pyrrole-3-carboxylic acid to be reacted and treated in a similar manner to give the titled compound (316 mg) as a white solid. MS(ESI) m/z: 454 (M+H)$^+$.

Example 35

N-{6-[4-(1-fluoro-1-methylethyl)piperidin-1-yl]-5-methylpyridin-3-yl}-1-(4-methoxyphenyl)-5-methyl-1H-pyrazole-4-carboxamide

[Chemical formula 89]

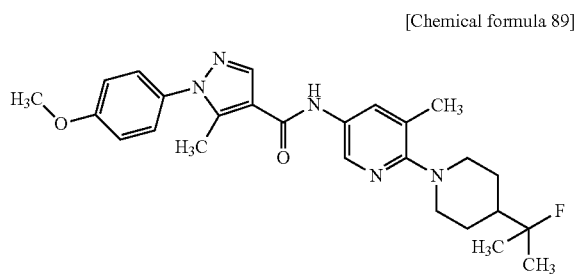 [SMILES: COc1ccc(-n2ncc(C(=O)Nc3cnc(N4CCC(C(C)(C)F)CC4)c(C)c3)c2C)cc1]

In Example 24, 1-(4-methoxyphenyl)-5-methyl-1H-pyrazole-4-carboxylic acid (185 mg) of Reference example 11 was used instead of 1-(5-cyanopyridin-2-yl)-1H-pyrrole-3-carboxylic acid to be reacted and treated in a similar manner to give the titled compound (295 mg) as a white solid. MS(ESI) m/z: 466 (M+H)$^+$.

Example 36

N-[5-chloro-6-(4-hydroxypiperidin-1-yl)pyridin-3-yl]-1-(4-chlorophenyl)-5-methyl-1H-pyrazole-4-carboxamide

[Chemical formula 90]

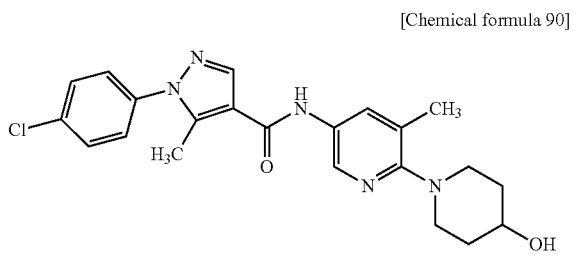 [SMILES: Cc1cc(NC(=O)c2cnn(-c3ccc(Cl)cc3)c2C)cnc1N1CCC(O)CC1]

(1) To a solution of 2,3-dichloropyridine (1.48 g) in N,N-dimethylformamide (10 ml) was added 4-piperidinol (2.23 g), and the mixture was stirred at 80° C. to 90° C. for 3 hours. To the reaction solution were added water and ethyl acetate, and the organic layer was washed with water. The organic layer was dried over sodium sulfate, and then concentrated to give a viscous body (1.76 g).
(2) To a solution of the resulted viscous body (1.75 g) in acetic acid (6 ml) was added pyridinium bromide perbromide (3.16 g) at room temperature, and the mixture was stirred at room temperature for 0.5 hour. To the reaction solution was added water, and the mixture was extracted with ethyl acetate. The organic layer was washed with water, saturated aqueous sodium hydrogen carbonate solution, saturated saline, and dried over sodium sulfate, and then concentrated. Silica gel column chromatography (n-hexane:ethyl acetate) was carried out to give 1-(5-bromo-3-chloropyridin-2-yl)piperidin-4-ol (1.4 g) as a viscous body.
(3) To a solution of 1-(5-bromo-3-chloropyridin-2-yl)piperidin-4-ol (321 mg) in 1,4-dioxane (1.5 ml) were added 1-(4-chlorophenyl)-5-methyl-1H-pyrazole-4-carboxylic acid amide (286 mg) of Reference example 22, copper (I) iodide (16 mg), N,N'-dimethylethylenediamine (15 mg) and potassium carbonate (304 mg), and the mixture was stirred at 110° C. for 7 hours. After the completion of reaction, to the reaction solution was added water, and the mixture was extracted with methylene chloride and concentrated. The resulted residue was purified by silica gel column chromatography, and then the resulted solid was suspended and washed with ethanol to give the titled compound (300 mg) as a pale yellow solid. MS(ESI) m/z: 446 (M+H)$^+$.

Example 37

N-{5-cyano-6-[4-(2-hydroxyethyl)piperidin-1-yl]pyridin-3-yl}-1-(4-fluorophenyl)-1H-pyrrole-3-carboxamide

[Chemical formula 91]

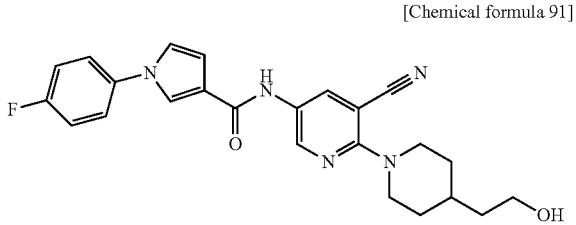 [SMILES: N#Cc1cc(NC(=O)c2ccn(-c3ccc(F)cc3)c2)cnc1N1CCC(CCO)CC1]

In Example 11(4), 1-(4-fluorophenyl)-1H-pyrrole-3-carboxylic acid (437 mg) of Reference example 23 was used instead of 1-(4-chlorophenyl)-5-(trifluoromethyl)-1H-pyrazole-4-carboxylic acid to be reacted and treated in a similar manner to Example 11(4) and Example 30 to give the titled compound (612 mg) as a solid. MS(ESI) m/z: 434 (M+H)$^+$.

Example 38

1-(5-chloropyridin-2-yl)-N-{6-[4-(1-fluoro-1-methylethyl)piperidin-1-yl]-5-methylpyridin-3-yl}-5-methyl-1H-pyrazole-4-carboxamide

[Chemical formula 92]

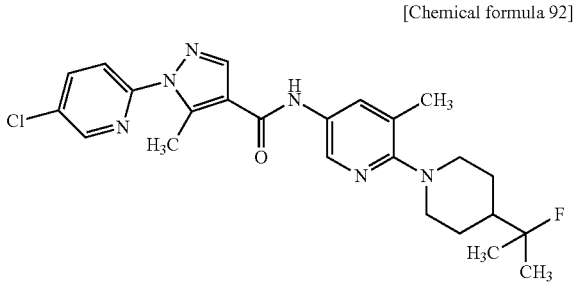 [SMILES: Cc1cc(NC(=O)c2cnn(-c3ccc(Cl)cn3)c2C)cnc1N1CCC(C(C)(C)F)CC1]

In Example 24, 1-(5-chloropyridin-2-yl)-5-methyl-1H-pyrazole-4-carboxylic acid (189 mg) of Reference example 2 was used instead of 1-(5-cyanopyridin-2-yl)-1H-pyrrole-3-carboxylic acid to be reacted and treated in a similar manner to give the titled compound (276 mg) as a white solid. MS(ESI) m/z: 471 (M+H)$^+$.

Example 39

1-(4-chlorophenyl)-N-[5-cyclopropyl-6-(4-hydroxypiperidin-1-yl)pyridin-3-yl]-5-methyl-1H-pyrazole-4-carboxamide

[Chemical formula 93]

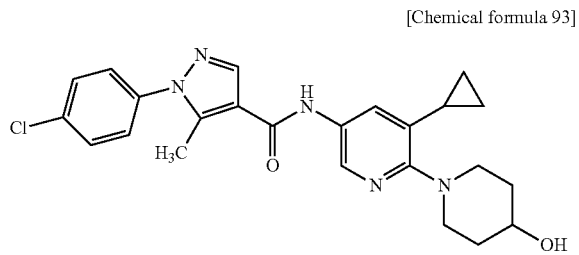 [SMILES: Cc1c(C(=O)Nc2cnc(N3CCC(O)CC3)c(C3CC3)c2)cnn1-c1ccc(Cl)cc1]

(1) To a solution of 3-bromo-2-chloro-5-nitropyridine (2.38 g) in N,N-dimethylformamide (10 ml) was added 4-piperidinol (2.23 g), and the mixture was stirred at 60° C. for 0.5 hour. To the reaction solution was added water, and the precipitated solid was filtered to give a yellow solid (2.83 g).

(2) To a solution of the resulted yellow solid (2.8 g) in pyridine (14 ml) was added benzoyl chloride (1.38 g) under ice cooling, and the mixture was stirred for 3 hours with gradually warming from 0° C. to room temperature. To the reaction solution was further added pyridine (10 ml), and thereto was added benzoyl chloride (250 mg) under ice cooling, and the mixture was stirred for 3 hours with gradually warming from 0° C. to room temperature. To the reaction solution was added water, and the precipitated solid was filtered to give a yellow solid (3.1 g).

(3) To a solution of the resulted yellow solid (1.22 g) in water (1 ml) and toluene (12 ml) were added cyclopropylboronic acid (335 mg), tripotassium phosphate (2.23 g) and dichlorobis(tricyclohexylphosphine)palladium (II) (111 mg), and the mixture was stirred at 100° C. for 2.5 hours. To the reaction solution was added water, and the mixture was extracted with ethyl acetate and concentrated. The resulted residue was purified by silica gel column chromatography (n-hexane:ethyl acetate) to give a yellow solid (980 mg).

(4) To a solution of the resulted yellow solid (940 mg) in tetrahydrofuran (10 ml) and methanol (10 ml) was added 10% palladium carbon (150 mg), and the mixture was stirred under hydrogen at room temperature for 2 hours. The reaction solution was filtered through Celite, concentrated, and then column chromatography (n-hexane:ethyl acetate) was carried out to give a purified substance (730 mg).

(5) To a solution of the purified substance (715 mg) obtained in the above operation in pyridine (10 ml) was added acid chloride (543 mg) which was prepared from 1-(4-chlorophenyl)-5-methyl-1H-pyrazole-4-carboxylic acid of Reference example 6 in a similar manner to the method of Reference example 1(3) under ice cooling, and the mixture was stirred for 0.5 hour with gradually warming from ice cooled temperature to room temperature. To the reaction solution was added triethylamine (1.2 equivalents), and the mixture was stirred at room temperature for additional 1 hour. To the reaction solution was added water, and the mixture was extracted with ethyl acetate, and the organic layer was concentrated. The resulted residue was suspended and washed with ethyl acetate to give a white solid (1.08 g). To the resulted solid (700 mg) were added ethanol (10 ml) and 1N aqueous sodium hydroxide solution (1.5 ml), and the mixture was stirred at 90° C. for 1.5 hours. To the reaction solution was added water, and the precipitated solid was filtered to give the titled compound (521 mg) as a white solid. MS(ESI) m/z: 452 (M+H)$^+$.

Example 40 acetic acid [2-(1-{5-[1-(4-chlorophenyl)-5-methyl-1H-pyrazole-4-carboxamide]-3-cyanopyridin-2-yl}piperidin-4-yl)ethyl]ester

[Chemical formula 94]

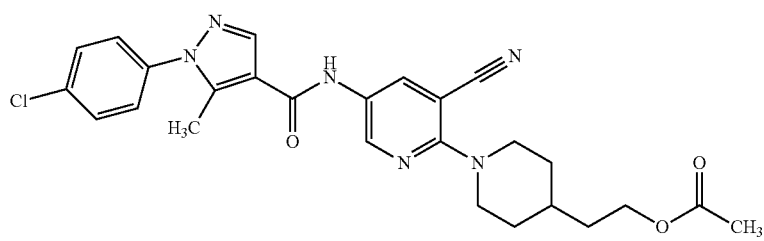

A reaction mixture (337 mg) which was obtained by reacting and treating in a similar manner to Reference example 1(3) using 1-(4-chlorophenyl)-5-methyl-1H-pyrazole-4-carboxylic acid of Reference example 6 instead of 5-methyl-1-[5-(trifluoromethyl)pyridin-2-yl]-1H-pyrazole-4-carboxylic acid was added to a solution of solid (346 mg) obtained in Example 11(3) in pyridine (6.0 ml) under ice cooling, and the mixture was stirred at the same temperature for 0.25 hour, and then thereto was added triethylamine, and the mixture was stirred at room temperature overnight. After the completion of reaction, to the mixture was added water, and the precipitated solid was filtered, and then suspended and washed with ethanol to give the titled compound (590 mg) as a solid. MS(ESI) m/z: 507 (M+H)$^+$.

Example 41

1-(4-chlorophenyl)-N-{6-[4-(1-fluoro-1-methylethyl)piperidin-1-yl]-5-methylpyridin-3-yl}-5-methyl-1H-pyrazole-4-carboxamide

[Chemical formula 95]

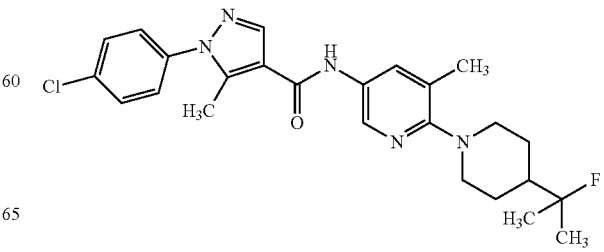

In Example 24, 1-(4-chlorophenyl)-5-methyl-1H-pyrazole-4-carboxylic acid (188 mg) of Reference example 6 was used instead of 1-(5-cyanopyridin-2-yl)-1H-pyrrole-3-carboxylic acid to be reacted and treated in a similar manner to give the titled compound (355 mg) as a white solid. MS(ESI) m/z: 470 (M+H)+.

Example 42

1-(4-chlorophenyl)-N-{5-cyclopropyl-6-[4-(2-hydroxyethyl)piperidin-1-yl]pyridin-3-yl}-5-methyl-1H-pyrazole-4-carboxamide

[Chemical formula 96]

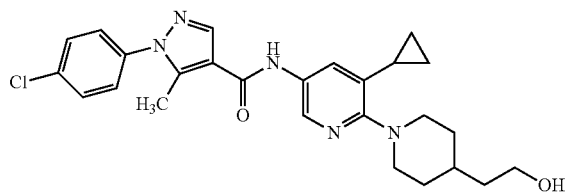

To a solution of a viscous body (400 mg) obtained in Example 18(4) in pyridine (6 ml) was added under ice cooling the acid chloride (307 mg) which was prepared from 1-(4-chlorophenyl)-5-methyl-1H-pyrazole-4-carboxylic acid of Reference example 6 in a similar manner to the method of Reference example 1(3), and the mixture was stirred at room temperature for 2 hours. To the reaction solution was added water, and the precipitated solid was filtered and suspended and washed with ethanol. To the resulted solid were added ethanol (8 ml) and 1N aqueous sodium hydroxide solution (1.5 ml), and the mixture was stirred at 65° C. for 1 hour. The reaction solution was cooled to room temperature, and the precipitated solid was filtered. To the resulted solid was added ethanol (2 ml), and the mixture was suspended and washed under heating to give the titled compound (384 mg) as a white solid. MS(ESI) m/z: 480 (M+H)+.

Example 43

1-(4-chlorophenyl)-N-[6-(4-hydroxypiperidin-1-yl)-5-methylpyridin-3-yl]-5-methyl-1H-pyrazole-4-carboxamide

[Chemical formula 97]

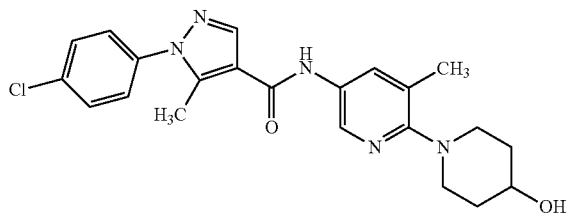

To a solution of a viscous body (405 mg) obtained in Example 2(3) in pyridine (6 ml) was added under ice cooling the acid chloride (365 mg) which was prepared from 1-(4-chlorophenyl)-5-methyl-1H-pyrazole-4-carboxylic acid of Reference example 6 in a similar manner to the method of Reference example 1(3), and the mixture was stirred at the same temperature for 15 minutes. To the reaction solution was added triethylamine (1.2 equivalents), and the mixture was stirred at room temperature for 2 hours. To the reaction solution was added water, and the precipitated solid was filtered. To the resulted solid were added ethanol (8 ml) and 1N aqueous sodium hydroxide solution (2.6 ml), and the mixture was stirred at 65° C. for 15 minutes. To the reaction solution was added tetrahydrofuran (4 ml), and the mixture was stirred at 65° C. for additional 1 hour. To the reaction solution was added water, and the mixture was extracted with ethyl acetate and concentrated. The resulted residue was suspended and washed with ethanol to give the titled compound (414 mg) as a solid. MS(ESI) m/z: 426 (M+H)+.

Example 44

1-(4-chlorophenyl)-N-[5-cyano-6-(4-hydroxypiperidin-1-yl)pyridin-3-yl]-5-methyl-1H-pyrazole-4-carboxamide

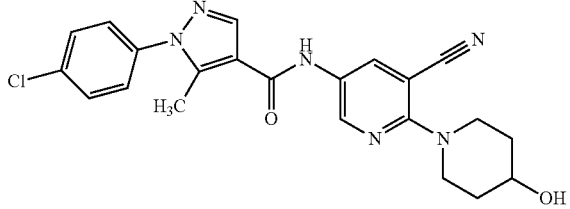 [SMILES: Cc1c(C(=O)Nc2cnc(N3CCC(O)CC3)c(C#N)c2)cnn1-c1ccc(Cl)cc1]

To a solution of acetic acid (1-{5-[1-(4-chlorophenyl)-5-methyl-1H-pyrazole-4-carboxamide]-3-cyanopyridin-2-yl}piperidin-4-yl)ester (510 mg) of Example 19 in ethanol (8.0 ml) was added 1N aqueous sodium hydroxide solution (1.3 ml) at room temperature, and the mixture was stirred at 45° C. for 0.5 hour. After the completion of reaction, the mixture was cooled to room temperature, and thereto was added water, and then the precipitated solid was filtered to give the titled compound (410 mg) as a white solid. MS(ESI) (m/z): 437 (M+H)+.

Example 45

N-[5-cyano-6-(4-hydroxypiperidin-1-yl)pyridin-3-yl]-5-methyl-1-[4-(trifluoromethyl)phenyl]-1H-pyrazole-4-carboxamide

[Chemical formula 99]

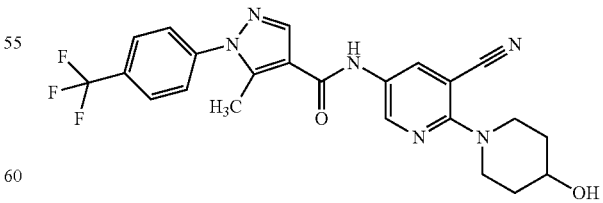

(1) To a solution of 5-methyl-1-[4-(trifluoromethyl)phenyl]-1H-pyrazole-4-carboxylic acid (550 mg) of Reference example 10 in dichloroethane (8.0 ml) were added thionyl chloride (367 mg) and N,N-dimethylformamide (catalytic amount), and the mixture was stirred at 80° C. for 1 hour, and solvent and excess thionyl chloride were distilled away. To a solution of the resulted reaction mixture in tetrahydrofuran (3.0 ml) was added a solution of the solid (573 mg) obtained in Example 5(6) in pyridine (10 ml), and the mixture was stirred at the same temperature for 1 hour. After the completion of reaction, to the mixture was added water, and the mixture was extracted with chloroform. The organic layer was dried over anhydrous sodium sulfate, and then solvent was distilled away. The resulted residue was purified by silica gel column chromatography (chloroform:methanol) to give [1-(3-cyano-5-{5-methyl-1-[4-(trifluoromethyl)phenyl]-1H-pyrazole-4-carboxamide}pyridin-2-yl)piperidin-4-yl]acetic acid ester (504 mg) as a solid. MS(ESI) m/z: 513 (M+H)$^+$.

(2) To a solution of [1-(3-cyano-5-{(5-methyl-1-[4-(trifluoromethyl)phenyl]-1H-pyrazole-4-carboxamide}pyridin-2-yl)piperidin-4-yl]acetic acid ester (450 mg) in ethanol (8.0 ml) was added 1N aqueous sodium hydroxide solution (1.2 ml) at room temperature, and the mixture was stirred at room temperature for 1.5 hours. After the completion of reaction, the mixture was cooled to room temperature, and thereto were added 1N aqueous hydrochloric acid solution and water, and then the precipitated solid was filtered. The resulted solid was purified by silica gel column chromatography (chloroform/methanol), and then suspended and washed with ethanol to give the titled compound (365 mg) as a white solid. MS(ESI) (m/z): 471 (M+H)$^+$.

Example 46

1-(5-cyanopyridin-2-yl)-N-{6-[4-(1-hydroxy-1-methylethyl)piperidin-1-yl]-5-methylpyridin-3-yl}-1H-pyrrole-3-carboxamide

[Chemical formula 100]

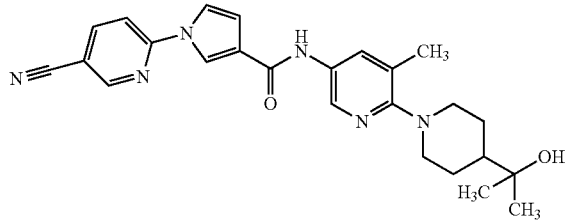

(1) To a solution of 2-bromo-3-methyl-5-nitropyridine (12.7 g) in N,N-dimethylformamide (120 ml) were added 2-(4-piperidinyl)-2-propanol (8.35 g) and potassium carbonate (16.2 g) at room temperature, and the mixture was stirred at 80° C. for 4 hours. After the completion of reaction, the mixture was cooled to room temperature, and thereto was added water, and the precipitated solid was filtered to give a yellow solid.

(2) To a solution of the resulted solid in tetrahydrofuran (240 ml) was added an aqueous solution (60 ml) of palladium (II) acetate (1.31 g) and potassium fluoride (13.5 g) at room temperature, and thereto was slowly added dropwise poly(methylhydrosiloxane) (14 ml), and then the mixture was stirred at the same temperature for 1 hour. After the completion of reaction, to the mixture was added diethyl ether (240 ml), and the mixture was filtered through Celite, and then solvent was distilled away. To the resulted residue was added water, and the mixture was extracted with ethyl acetate. The organic layer was dried over anhydrous sodium sulfate, and then solvent was distilled away. The resulted residue was purified by basic silica gel column chromatography (n-hexane:ethyl acetate) to give 1-[1-(5-amino-3-methylpyridin-2-yl)piperidin-4-yl]-1-methylethyl-1-ol (9.16 g) as a white solid. MS(ESI) m/z: 250 (M+H)$^+$.

(3) To a solution of 1-(5-cyanopyridin-2-yl)-1H-pyrrole-3-carboxylic acid (200 mg) of Reference example 14 in toluene (5.0 ml) were added thionyl chloride (335 mg) and N,N-dimethylformamide (catalytic amount) at room temperature, and the mixture was stirred at 80° C. for 1 hour, and then solvent and excess thionyl chloride were distilled away. To the resulted reaction was added pyridine (5.0 ml), and then thereto was added a solution of 1-[1-(5-amino-3-methylpyridin-2-yl)piperidin-4-yl]-1-methylethyl-1-ol (234 mg) in pyridine (5.0 ml), and the mixture was stirred at 50° C. for 1 hour. After the completion of reaction, to the mixture were added triethylamine (2.0 ml) and water, and the precipitated solid was filtered. The resulted solid was suspended and washed with ethanol to give the titled compound (292 mg) as a white solid. MS(ESI) m/z: 445 (M+H)$^+$.

Example 47

N-{6-[4-(1-fluoro-1-methylethyl)piperidin-1-yl]-5-methylpyridin-3-yl}-5-methyl-1-[4-(trifluoromethyl)phenyl]-1H-pyrazole-4-carboxamide

[Chemical formula 101]

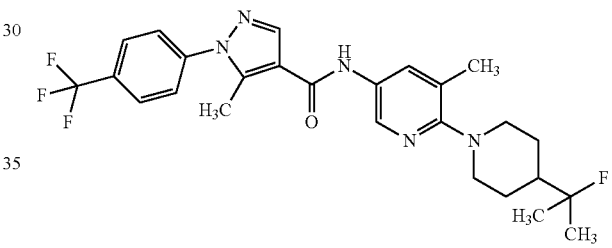

In Example 24, 5-methyl-1-[4-(trifluoromethyl)phenyl]-1H-pyrazole-4-carboxylic acid (220 mg) of Reference example 10 was used instead of 1-(5-cyanopyridin-2-yl)-1H-pyrrole-3-carboxylic acid to be reacted and treated in a similar manner to give the titled compound (381 mg) as a white solid. MS(ESI) m/z: 504 (M+H)$^+$.

Example 48

1-(3,5-dichloropyridin-2-yl)-N-{6-[4-(1-fluoro-1-methylethyl)piperidin-1-yl]-5-methylpyridin-3-yl}-5-methyl-1H-pyrazole-4-carboxamide

[Chemical formula 102]

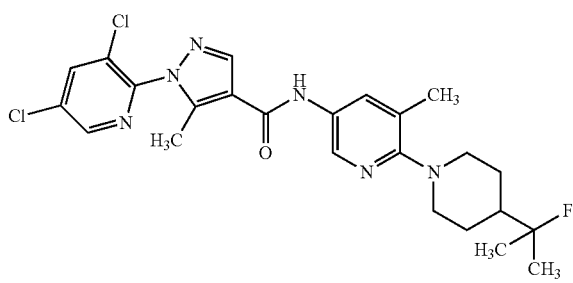

In Example 24, 1-(3,5-dichloropyridin-2-yl)-5-methyl-1H-pyrazole-4-carboxylic acid (271 mg) of Reference example 3 was used instead of 1-(5-cyanopyridin-2-yl)-1H-pyrrole-3-carboxylic acid to be reacted and treated in a similar manner to give the titled compound (347 mg) as a white solid. MS(ESI) m/z: 505 (M+H)⁺.

Example 49

N-{6-[4-(1-fluoro-1-methylethyl)piperidin-1-yl]-5-methylpyridin-3-yl}-5-methyl-1-[5-(trifluoromethyl)pyridin-2-yl]-1H-pyrazole-4-carboxamide

[Chemical formula 103]

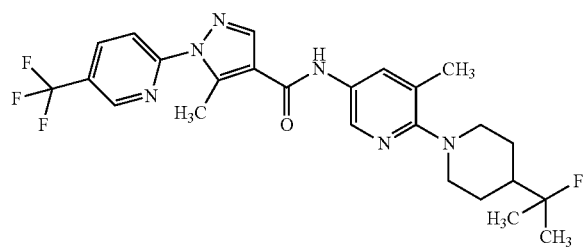

In Example 24, 5-methyl-1-[5-(trifluoromethyl)pyridin-2-yl]-1H-pyrazole-4-carboxylic acid (162 mg) of Reference example 1(2) was used instead of 1-(5-cyanopyridin-2-yl)-1H-pyrrole-3-carboxylic acid to be reacted and treated in a similar manner to give the titled compound (236 mg) as a white solid. MS(ESI) m/z: 505 (M+H)⁺.

Example 50

N-{6-[4-(2-hydroxy-2-methylpropyl)piperidin-1-yl]-5-methylpyridin-3-yl}-5-methyl-1-phenyl-1H-pyrazole-4-carboxamide

[Chemical formula 104]

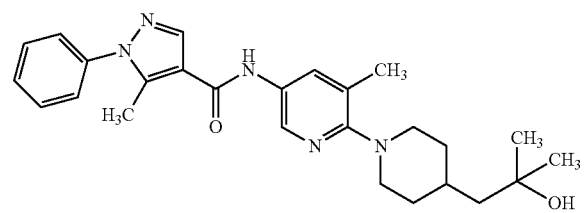

In Example 26(5), 5-methyl-1-phenyl-1H-pyrazole-4-carboxylic acid (150 mg) of Reference example 17 was used instead of 5-methyl-1-(pyridin-2-yl)-1H-pyrazole-4-carboxylic acid to be reacted and treated in a similar manner to give the titled compound (234 mg) as a white solid. MS(ESI) m/z: 448 (M+H)⁺.

Example 51

1-(4-chlorophenyl)-N-{5-cyano-6-[4-(2-hydroxyethyl)piperidin-1-yl]pyridin-3-yl}-5-methyl-1H-pyrazole-4-carboxamide

[Chemical formula 105]

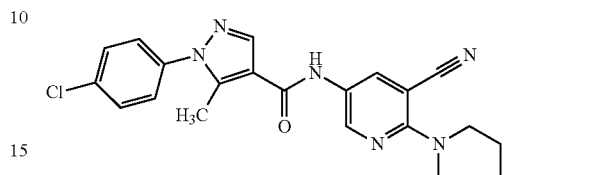

To a solution of [2-(1-{5-[1-(4-chlorophenyl)-5-methyl-1H-pyrazole-4-carboxamide]-3-cyanopyridin-2-yl}piperidin-4-yl)ethyl]acetic acid ester (520 mg) of Example 40 in ethanol (8.0 ml) was added 1N aqueous sodium hydroxide solution (2.0 ml) at room temperature, and the mixture was stirred at 50° C. for 1 hour. After the completion of reaction, the mixture was cooled to room temperature, and thereto was added water, and then the precipitated solid was filtered. The resulted solid was suspended and washed with ethanol to give the titled compound (426 mg) as a white solid. MS(ESI) (m/z): 465 (M+H)⁺.

Example 52 acetic acid {1-[1-(3-methyl-5-{5-methyl-1-[5-(trifluoromethyl)pyridin-2-yl]-1H-pyrazole-4-carboxamide}pyridin-2-yl)piperidin-4-yl]ethyl}ester

[Chemical formula 106]

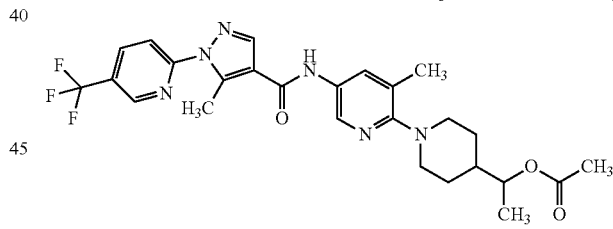

(1) To a solution of 1-Boc-4-piperidinealdehyde (1.87 g) in tetrahydrofuran (18 ml) was added dropwise a 1.06M solution of methylmagnesium bromide in tetrahydrofuran (9.6 ml) at −78° C., and the mixture was stirred at room temperature for 0.5 hour. After the completion of reaction, the mixture was cooled to room temperature, and thereto was added a saturated aqueous ammonium chloride solution, and then the mixture was extracted with ethyl acetate. The organic layer was dried over anhydrous sodium sulfate, and then solvent was distilled away. To a solution of the resulted residue in ethyl acetate (18 ml) was added 4N hydrochloric acid/ethyl acetate solution (18 ml) at room temperature, and the mixture was stirred at the same temperature for 4 hours. After the completion of reaction, excess hydrochloric acid and solvent were distilled away. In addition, to a solution of the resulted residue in N,N-dimethylformamide (9.0 ml) were added 2-bromo-3-methyl-5-nitropyridine (1.9 g) and potassium carbonate (1.94 g) at room temperature, and the mixture was stirred at 80° C. for 4 hours. After the completion of reaction, the mixture was cooled to room temperature, and thereto was added water, and then the mixture was extracted with ethyl acetate. The organic layer was dried over anhydrous sodium sulfate, and then solvent was distilled away.

(2) To a solution of the resulted residue in pyridine (11.2 ml) was added acetic anhydride (5.6 ml) at room temperature, and the mixture was stirred at the same temperature for 1 hour, and then stirred at 50° C. for 2 hours. After the completion of reaction, the mixture was cooled to room temperature, and thereto was added water, and then the mixture was extracted with ethyl acetate. The organic layer was dried over anhydrous sodium sulfate, and then solvent was distilled away. Then, to a solution of the resulted residue in tetrahydrofuran (28 ml) was added an aqueous solution (5.4 ml) of palladium (II) acetate (124 mg) and potassium fluoride (640 mg) at room temperature, and thereto was slowly added dropwise poly(methylhydrosiloxane) (0.7 ml), and then the mixture was stirred at the same temperature for 1 hour. After the completion of reaction, to the mixture was added diethyl ether (28 ml), and the mixture was filtered through Celite, and then solvent was distilled away. To the resulted residue was added water, and the mixture was extracted with ethyl acetate. The organic layer was dried over anhydrous sodium sulfate, and then solvent was distilled away. The resulted residue was purified by silica gel column chromatography (chloroform:methanol) to give a brown viscous body.

(3) To a solution of 5-methyl-1-[5-(trifluoromethyl)pyridin-2-yl]-1H-pyrazole-4-carboxylic acid (421 mg) of Reference example 1(2) in toluene (7.5 ml) were added thionyl chloride (554 mg) and N,N-dimethylformamide (catalytic amount) at room temperature, and the mixture was stirred at 80° C. for 1 hour, and then solvent and excess thionyl chloride were distilled away. To the resulted reaction mixture was added pyridine (7.5 ml), and then thereto was added a solution of a viscous body (430 mg) obtained in (2) in pyridine (7.5 ml), and the mixture was stirred at 50° C. for 1 hour. After the completion of reaction, to the mixture were added triethylamine (2.0 ml) and water, and the precipitated solid was filtered. The resulted solid was purified by silica gel column chromatography (chloroform:methanol) to give the titled compound (718 mg) as a white solid. MS(ESI) m/z: 531 (M+H)$^+$.

Example 53

N-{6-[4-(1-methoxyethyl)piperidin-1-yl]-5-methyl-pyridin-3-yl}-5-methyl-1-[5-(trifluoromethyl)pyridin-2-yl]-1H-pyrazole-4-carboxamide

[Chemical formula 107]

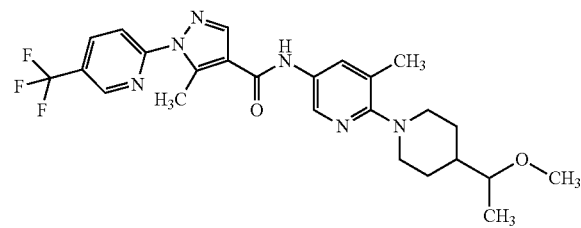

(1) To a solution of 1-Boc-4-piperidinealdehyde (1.50 g) in tetrahydrofuran (14 ml) was added dropwise a 1.06M solution of methylmagnesium bromide in tetrahydrofuran (7.3 ml) at −78° C., and the mixture was stirred at room temperature for 0.5 hour. After the completion of reaction, the mixture was cooled to room temperature, and thereto was added a saturated aqueous ammonium chloride solution, and then the mixture was extracted with ethyl acetate. The organic layer was dried over anhydrous sodium sulfate, and then solvent was distilled away. To a solution of the resulted residue in ethyl acetate (28 ml) was added 4N hydrochloric acid/ethyl acetate solution (14 ml) at room temperature, and the mixture was stirred at the same temperature for 4 hours. After the completion of reaction, excess hydrochloric acid and solvent were distilled away. In addition, to a solution of the resulted residue in N,N-dimethylformamide (14 ml) were added 2-bromo-3-methyl-5-nitropyridine (1.53 g) and potassium carbonate (1.94 g) at room temperature, and the mixture was stirred at 80° C. for 4 hours. After the completion of reaction, the mixture was cooled to room temperature, and thereto was added water, and then the mixture was extracted with ethyl acetate. The organic layer was dried over anhydrous sodium sulfate, and then solvent was distilled away.

(2) To a solution of the resulted residue in N,N-dimethylformamide (10 ml) was added sodium hydride (99 mg) at room temperature, and the mixture was stirred at the same temperature for 0.5 hour. Then, thereto was added methyl iodide (0.4 ml), and the mixture was stirred at the same temperature for 2 hours. After the completion of reaction, to the mixture was added water, and the mixture was extracted with ethyl acetate. The organic layer was dried over anhydrous sodium sulfate, and then solvent was distilled away. The resulted residue was purified by silica gel column chromatography (n-hexane:ethyl acetate) to give 4-(1-methoxyethyl)-1-(3-methyl-5-nitropyridin-2-yl)piperidine (478 mg) as a yellow viscous body. MS(ESI) m/z: 280 (M+H)$^+$.

(3) To a solution of 4-(1-methoxyethyl)-1-(3-methyl-5-nitropyridin-2-yl)piperidine (478 mg) in tetrahydrofuran (17 ml) was added an aqueous solution (7.0 ml) of palladium (II) acetate (77 mg) and potassium fluoride (398 mg) at room temperature, and thereto was slowly added dropwise poly (methylhydrosiloxane) (0.4 ml), and then the mixture was stirred at the same temperature for 1 hour. After the completion of reaction, to the mixture was added diethyl ether (17 ml), and the mixture was filtered through Celite, and then solvent was distilled away. To the resulted residue was added water, and the mixture was extracted with ethyl acetate. The organic layer was dried over anhydrous sodium sulfate, and then solvent was distilled away. The resulted residue was purified by silica gel column chromatography (chloroform: methanol) to give a brown viscous body (427 mg).

(4) To a solution of 5-methyl-1-[5-(trifluoromethyl)pyridin-2-yl]-1H-pyrazole-4-carboxylic acid (464 mg) of Reference example 1(2) in toluene (8.5 ml) were added thionyl chloride (611 mg) and N,N-dimethylformamide (catalytic amount) at room temperature, and the mixture was stirred at 80° C. for 1 hour, and then solvent and excess thionyl chloride were distilled away. To the resulted reaction mixture was added pyridine (8.5 ml), and then thereto was added a solution of a viscous body (427 mg) obtained in (3) in pyridine (8.5 ml), and the mixture was stirred at 50° C. for 1 hour. After the completion of reaction, to the mixture were added triethylamine (2.0 ml) and water, and the precipitated solid was filtered. The resulted solid was purified by silica gel column chromatography (chloroform:methanol) to give the titled compound (102 mg) as a white solid. MS(ESI) m/z: 503 (M+H)$^+$.

Example 54

1-(4-fluorophenyl)-N-{6-[4-(1-hydroxy-1-methyl-ethyl)piperidin-1-yl]-5-methylpyridin-3-yl}-5-methyl-1H-pyrazole-4-carboxamide

[Chemical formula 108]

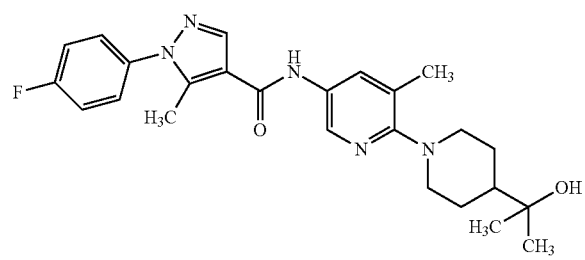

In Example 46(3), 1-(4-fluorophenyl)-5-methyl-1H-pyrazole-4-carboxylic acid (221 mg) of Reference example 4 was used instead of 1-(5-cyanopyridin-2-yl)-1H-pyrrole-3-carboxylic acid to be reacted and treated in a similar manner to give the titled compound (416 mg) as a white solid. MS(ESI) m/z: 452 (M+H)$^+$.

Example 55

N-{6-[4-(1-hydroxyethyl)piperidin-1-yl]-5-methyl-pyridin-3-yl}-5-methyl-1-[5-(trifluoromethyl)pyridin-2-yl]-1H-pyrazole-4-carboxamide

[Chemical formula 109]

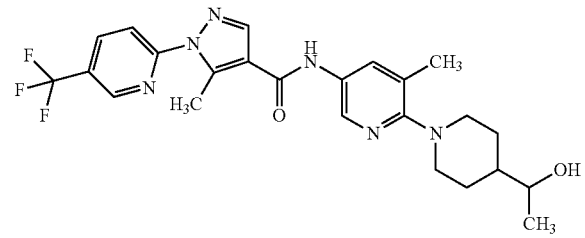

In Example 27, 5-methyl-1-[5-(trifluoromethyl)pyridin-2-yl]-1H-pyrazole-4-carboxylic acid (421 mg) of Reference example 1(2) was used instead of 1-(3,4-difluorophenyl)-5-methyl-1H-pyrazole-4-carboxylic acid to be reacted and treated in a similar manner to give the titled compound (508 mg) as a white solid. MS(ESI) m/z: 489 (M+H)$^+$.

Example 56

N-{6-[4-(1-hydroxy-1-methylethyl)piperidin-1-yl]-5-methylpyridin-3-yl}-5-methyl-1-(4-methylphenyl)-1H-pyrazole-4-carboxamide

[Chemical formula 110]

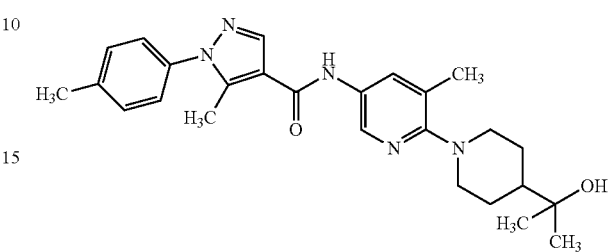

In Example 46(3), 5-methyl-1-(4-methylphenyl)-1H-pyrazole-4-carboxylic acid (217 mg) of Reference example 5 was used instead of 1-(5-cyanopyridin-2-yl)-1H-pyrrole-3-carboxylic acid to be reacted and treated in a similar manner to give the titled compound (324 mg) as a white solid. MS(ESI) m/z: 448 (M+H)$^+$.

Example 57

N-{6-[4-(2-hydroxy-2-methylpropyl)piperidin-1-yl]-5-methylpyridin-3-yl}-5-methyl-1-(5-methylpyridin-2-yl)-1H-pyrazole-4-carboxamide

[Chemical formula 111]

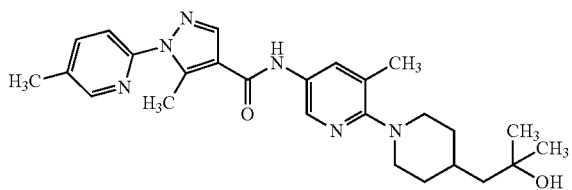

In Example 26(5), 5-methyl-1-(5-methylpyridin-2-yl)-1H-pyrazole-4-carboxylic acid (150 mg) of Reference example 20 was used instead of 5-methyl-1-(pyridin-2-yl)-1H-pyrazole-4-carboxylic acid to be reacted and treated in a similar manner to give the titled compound (241 mg) as a white solid. MS(ESI) m/z: 463 (M+H)$^+$.

Example 58

1-(5-chloropyridin-2-yl)-N-{6-[4-(1-hydroxy-1-methylethyl)piperidin-1-yl]-5-methylpyridin-3-yl}-5-methyl-1H-pyrazole-4-carboxamide

[Chemical formula 112]

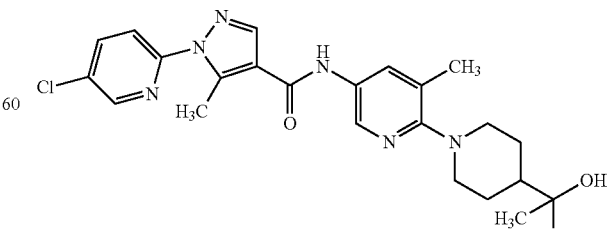

In Example 46(3), 1-(5-chloropyridin-2-yl)-5-methyl-1H-pyrazole-4-carboxylic acid (238 mg) of Reference example 2 was used instead of 1-(5-cyanopyridin-2-yl)-1H-pyrrole-3-carboxylic acid to be reacted and treated in a similar manner to give the titled compound (317 mg) as a white solid. MS(ESI) m/z: 469 (M+H)$^+$.

Example 59

1-(3,5-dichloropyridin-2-yl)-N-{6-[4-(1-hydroxy-1-methylethyl)piperidin-1-yl]-5-methylpyridin-3-yl}-5-methyl-1H-pyrazole-4-carboxamide

[Chemical formula 113]

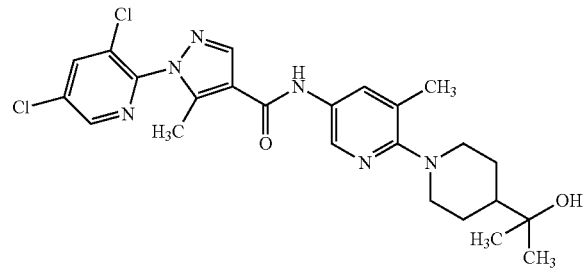

In Example 46(3), 1-(3,5-dichloropyridin-2-yl)-5-methyl-1H-pyrazole-4-carboxylic acid (220 mg) of Reference example 3 was used instead of 1-(5-cyanopyridin-2-yl)-1H-pyrrole-3-carboxylic acid to be reacted and treated in a similar manner to give the titled compound (238 mg) as a white solid. MS(ESI) m/z: 503 (M+H)$^+$.

Example 60

1-(5-fluoropyridin-2-yl)-N-{6-[4-(2-hydroxy-2-methylpropyl)piperidin-1-yl]-5-methylpyridin-3-yl}-5-methyl-1H-pyrazole-4-carboxamide

[Chemical formula 114]

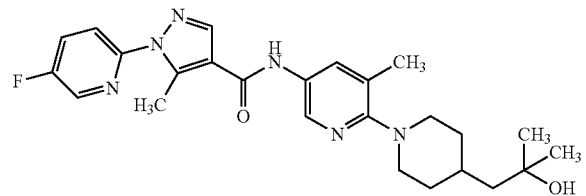

In Example 26(5), 1-(5-fluoropyridin-2-yl)-5-methyl-1H-pyrazole-4-carboxylic acid (150 mg) of Reference example 19 was used instead of 5-methyl-1-(pyridin-2-yl)-1H-pyrazole-4-carboxylic acid to be reacted and treated in a similar manner to give the titled compound (244 mg) as a white solid. MS(ESI) m/z: 467 (M+H)$^+$.

Example 61

N-{6-[4-(1-hydroxy-1-methylethyl)piperidin-1-yl]-5-methylpyridin-3-yl}-5-methyl-1-[4-(trifluoromethyl)phenyl]-1H-pyrazole-4-carboxamide

[Chemical formula 115]

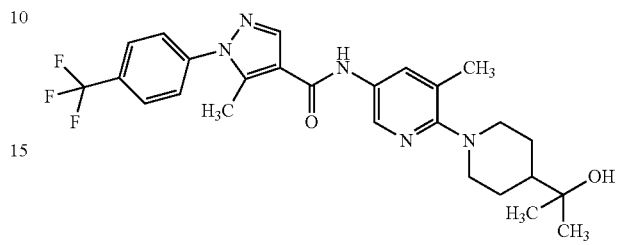

In Example 46(3), 5-methyl-1-[4-(trifluoromethyl)phenyl]-1H-pyrazole-4-carboxylic acid (200 mg) of Reference example 10 was used instead of 1-(5-cyanopyridin-2-yl)-1H-pyrrole-3-carboxylic acid to be reacted and treated in a similar manner to give the titled compound (310 mg) as a white solid. MS(ESI) m/z: 502 (M+H)$^+$.

Example 62

N-{6-[4-(1-hydroxy-1-methylethyl)piperidin-1-yl]-5-methylpyridin-3-yl}-5-methyl-1-[5-(trifluoromethyl)pyridin-2-yl]-1H-pyrazole-4-carboxamide

[Chemical formula 116]

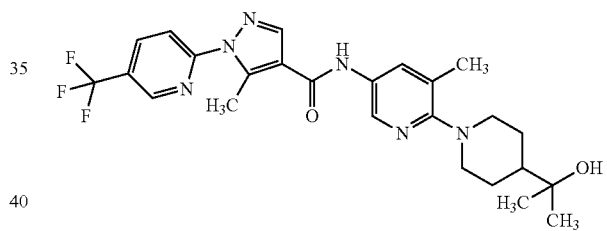

In Example 46(3), 5-methyl-1-[5-(trifluoromethyl)pyridin-2-yl]-1H-pyrazole-4-carboxylic acid (163 mg) of Reference example 1(2) was used instead of 1-(5-cyanopyridin-2-yl)-1H-pyrrole-3-carboxylic acid to be reacted and treated in a similar manner to give the titled compound (231 mg) as a white solid. MS(ESI) m/z: 503 (M+H)$^+$.

Example 63

1-(4-chlorophenyl)-N-{6-[4-(1-hydroxy-1-methylethyl)piperidin-1-yl]-5-methylpyridin-3-yl}-5-methyl-1H-pyrazole-4-carboxamide

[Chemical formula 117]

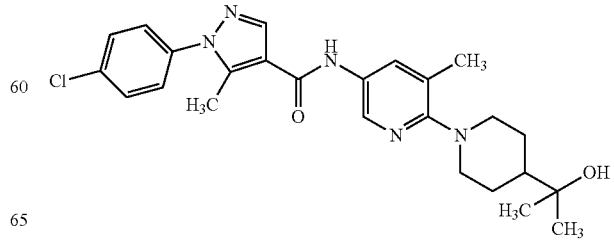

In Example 46(3), 1-(4-chlorophenyl)-5-methyl-1H-pyrazole-4-carboxylic acid (237 mg) of Reference example 6 was used instead of 1-(5-cyanopyridin-2-yl)-1H-pyrrole-3-carboxylic acid to be reacted and treated in a similar manner to give the titled compound (398 mg) as a white solid. MS(ESI) m/z: 468 (M+H)⁺.

Example 64

1-(5-cyclopropylpyridin-2-yl)-N-{6-[4-(2-hydroxy-2-methylpropyl)piperidin-1-yl]-5-methylpyridin-3-yl}-5-methyl-1H-pyrazole-4-carboxamide

[Chemical formula 118]

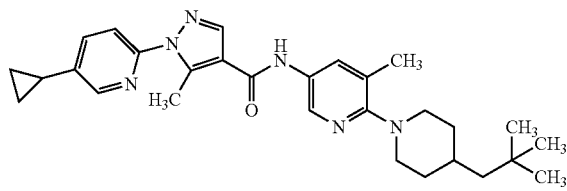

In Example 26(5), 1-(5-cyclopropylpyridin-2-yl)-5-methyl-1H-pyrazole-4-carboxylic acid (296 mg) of Reference example 15 was used instead of 5-methyl-1-(pyridin-2-yl)-1H-pyrazole-4-carboxylic acid to be reacted and treated in a similar manner to give the titled compound (425 mg) as a white solid. MS(ESI) m/z: 489 (M+H)⁺.

Example 65

N-{6-[4-(2-hydroxy-2-methylpropyl)piperidin-1-yl]-5-methylpyridin-3-yl}-5-methyl-1-[5-(trifluoromethyl)pyridin-2-yl]-1H-pyrazole-4-carboxamide

[Chemical formula 119]

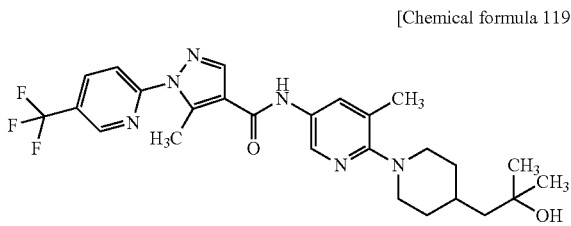

In Example 26(5), 5-methyl-1-[5-(trifluoromethyl)pyridin-2-yl]-1H-pyrazole-4-carboxylic acid (309 mg) of Reference example 1(2) was used instead of 5-methyl-1-(pyridin-2-yl)-1H-pyrazole-4-carboxylic acid to be reacted and treated in a similar manner to give the titled compound (431 mg) as a white solid. MS(ESI) m/z: 517 (M+H)⁺.

Example 66

N-[5-chloro-6-(4-methoxypiperidin-1-yl)pyridin-3-yl]-1-(4-chlorophenyl)-5-methyl-1H-pyrazole-4-carboxamide

[Chemical formula 120]

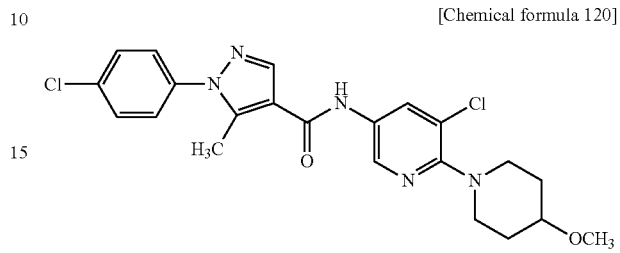

(1) To a solution of 2,3-dichloro-5-nitropyridine (1.9 g), acetonitrile (20 ml) and triethylamine (2.8 ml) was added 4-methoxypiperidine (1.21 g), and the mixture was stirred at 70° C. to 80° C. for 1 hour, and then thereto was added water, and the precipitated solid was filtered and washed with water to give 3-chloro-2-(4-methoxypiperidin-1-yl)-5-nitropyridine as a yellow solid. MS(ESI) m/z: 272 (M+H)⁺.

(2) To the resulted yellow solid were added iron powder (1.67 g), 2-propanol (10 ml), tetrahydrofuran (30 ml), water (10 ml) and acetic acid (1.14 ml), and the mixture was stirred at 90° C. for 1 hour, and then thereto was added an aqueous solution (30 ml) of potassium carbonate (4.4 g), and the mixture was stirred at room temperature. To the reaction solution was added Celite, and the mixture was stirred, and then filtered through Celite and washed with ethyl acetate, water. Then, the mixture was extracted with ethyl acetate, dried over anhydrous sodium sulfate, and solvent was distilled away under reduced pressure. The resulted residue was purified by basic silica gel chromatography (ethyl acetate: n-hexane) to give 5-amino-3-chloro-2-(4-methoxypiperidin-1-yl)pyridine as a red oil. MS(ESI) m/z: 242 (M+H)⁺.

(3) To a mixed solution of 4-chlorophenyl-1H-pyrazole-4-carboxylic acid (7.1 g) of Reference example 6 in toluene (71 ml) and N,N-dimethylformamide (0.5 ml) was added thionyl chloride (5.0 ml), and the mixture was stirred at 80° C. for 1 hour and a half, and then solvent was distilled away under reduced pressure to give 4-chlorophenyl-1H-pyrazole-4-carboxylic acid chloride as a pale yellow solid. ¹H-NMR (400 MHz, CDCl₃) δ: 2.56 (3H, s), 7.27-7.39 (2H, m), 7.50-7.53 (2H, m) 8.16 (1H, s).

(4) To a solution of 5-amino-3-chloro-2-(4-methoxypiperidin-1-yl)pyridine (242 mg) in pyridine (3.3 ml) was added 4-chlorophenyl-1H-pyrazole-4-carboxylic acid chloride (330 mg), and the mixture was stirred for 1.5 hours, and then thereto were added triethylamine (420 μl), water and 1N aqueous sodium hydroxide solution. The precipitated solid was filtered, and then purified by basic silica gel chromatography (ethyl acetate:n-hexane) to give the titled compound (242 mg) as a white solid. MS(ESI) m/z: 460 (M+H)⁺.

Example 67

N-[5-chloro-6-(1,4-dioxa-8-azaspiro[4,5]decan-8-yl)pyridin-3-yl]-1-(4-chlorophenyl)-5-methyl-1H-pyrazole-4-carboxamide

[Chemical formula 121]

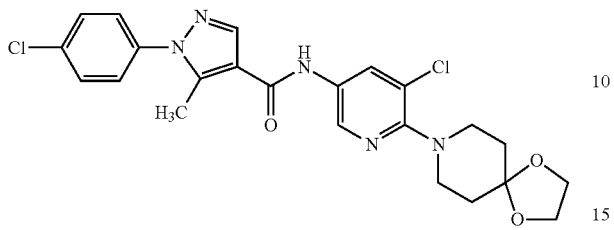

(1) To a solution of 2,3-dichloro-5-nitropyridine (1.9 g), acetonitrile (20 ml) and triethylamine (2.8 ml) was added 1,4-dioxa-8-azaspiro[4,5]decane (1.50 g), and the mixture was stirred at 70° C. to 80° C. for 1 hour, and then thereto was added water, and the precipitated solid was filtered and washed with water to give 8-(3-chloro-5-nitropyridin-2-yl)-1,4-dioxa-8-azaspiro[4,5]decane (2.89 g) as a yellow solid. MS(ESI) m/z: 300 (M+H)+.

(2) To 8-(3-chloro-5-nitropyridin-2-yl)-1,4-dioxa-8-azaspiro[4,5]decane (1.5 g) were added iron powder (838 mg), ammonium chloride (1.33 g), ethanol (30 ml) and water (15 ml), and the mixture was stirred at 80° C. for 3 hours, and then thereto was added an aqueous solution (15 ml) of potassium carbonate (2.2 g), and the mixture was stirred at room temperature. To the reaction solution was added Celite, and the mixture was stirred, and then filtered through Celite and washed with ethanol. Then, solvent was distilled away under reduced pressure. To the residue was added ethyl acetate, and the mixture was washed with water and saturated saline, dried over anhydrous sodium sulfate, and then solvent was distilled away under reduced pressure. The resulted residue was purified by basic silica gel chromatography (ethyl acetate:n-hexane) to give 5-chloro-6-(1,4-dioxa-8-azaspiro[4,5]decan-8-yl)pyridin-3-amine (680 mg) as a black solid. MS(ESI) m/z: 270 (M+H)+.

(3) To a solution of 5-chloro-6-(1,4-dioxa-8-azaspiro[4,5]decan-8-yl)pyridin-3-amine (680 mg) in pyridine (8.5 ml) was added 4-chlorophenyl-1H-pyrazole-4-carboxylic acid chloride (836 mg) of Example 66(3), and the mixture was stirred all night and all day, and then thereto were added water and 1N aqueous sodium hydroxide solution. The precipitated solid was filtered, and then purified by basic silica gel chromatography (ethyl acetate:n-hexane) to give the titled compound (1.09 g) as a pale red solid. MS(ESI) m/z: 488 (M+H)+.

Example 68

N-[5-chloro-6-(piperidin-4-on-1-yl)pyridin-3-yl]-1-(4-chlorophenyl)-5-methyl-1H-pyrazole-4-carboxamide

[Chemical formula 122]

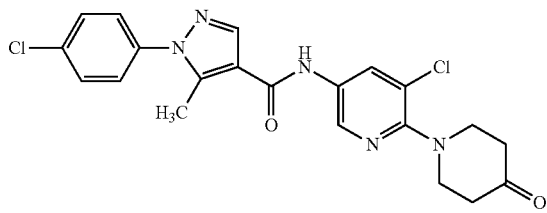

To a solution of (4-chlorophenyl)-N-[5-chloro-6-(1,4-dioxa-8-azaspiro[4,5]decan-8-yl)pyridin-3-yl]-1-5-methyl-1H-pyrazole-4-carboxamide (650 mg) of Example 67 in acetic acid (10 ml) was added 1N aqueous hydrochloric acid solution (2.5 ml), and the mixture was stirred at 70° C. for 2 hours, and then thereto were added water and 1N aqueous sodium hydroxide solution. The precipitated solid was filtered, and then purified by silica gel chromatography (chloroform:methanol), and the resulted solid was washed with ethyl acetate and methanol to give the titled compound (78 mg) as a pale red solid. MS(ESI) m/z: 444 (M+H)+.

Example 69

1-(4-chlorophenyl)-N-[5-cyclopropyl-6-(1,4-dioxa-8-azaspiro[4,5]decan-8-yl)pyridin-3-yl]-5-methyl-1H-pyrazole-4-carboxamide

[Chemical formula 123]

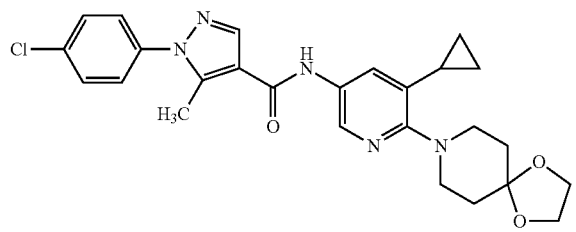

(1) To 8-(3-chloro-5-nitropyridin-2-yl)-1,4-dioxa-8-azaspiro[4,5]decane (1.39 g) of Example 67(1), bis(tricyclohexylphosphine)palladium (II) dichloride (170 mg), cyclopropylboronic acid (514 mg) and tripotassium phosphate (3.4 g) were added toluene (18 ml) and water (2 ml), and the mixture was stirred at 120° C. for 3 hours. To the reaction solution was added water, and the mixture was extracted with ethyl acetate, washed with saturated saline, dried over anhydrous sodium sulfate, and solvent was distilled away under reduced pressure. To the resulted residue were added iron powder (770 mg), ammonium chloride (1.23 g), ethanol (30 ml) and water (15 ml), and the mixture was stirred at 80° C. for 2.5 hours, and then thereto was added an aqueous solution (15 ml) of potassium carbonate (2.0 g), and the mixture was stirred at room temperature. To the reaction solution was added Celite, and the mixture was stirred, and then filtered through Celite, washed with ethanol, and then solvent was distilled away under reduced pressure. To the residue was added ethyl acetate, and the mixture was washed with water and saturated saline, dried over anhydrous sodium sulfate, and then solvent was distilled away under reduced pressure. The resulted residue was purified by basic silica gel chromatography (ethyl acetate:n-hexane) to give 5-cyclopropyl-6-(1,4-dioxa-8-azaspiro[4,5]decan-8-yl)pyridin-3-amine (670 mg) as a yellow oil. MS(ESI) m/z: 276 (M+H)+.

(2) To a solution of 5-cyclopropyl-6-(1,4-dioxa-8-azaspiro[4,5]decan-8-yl)pyridin-3-amine (670 mg) in pyridine (8.0 ml) was added 4-chlorophenyl-1H-pyrazole-4-carboxylic acid chloride (796 mg) of Example 66(3), and the mixture was stirred for 1 hour, and then thereto were added triethylamine (1 ml), water and 1N aqueous sodium hydroxide solution. The precipitated solid was filtered, and then purified by basic silica gel chromatography (ethyl acetate:n- hexane) to give the titled compound (520 mg) as a white solid. MS(ESI) m/z: 494 (M+H)+.

Example 70

1-(4-chlorophenyl)-N-[5-cyclopropyl-6-(piperidin-4-on-1-yl)pyridin-3-yl]-5-methyl-1H-pyrazole-4-carboxamide

[Chemical formula 124]

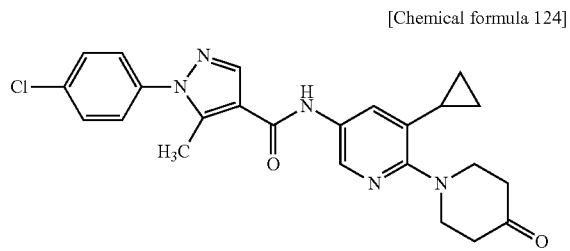 [SMILES: Cc1c(C(=O)Nc2cnc(N3CCC(=O)CC3)c(C3CC3)c2)cnn1-c1ccc(Cl)cc1]

To a solution of 1-(4-chlorophenyl)-N-[5-cyclopropyl-6-(1,4-dioxa-8-azaspiro[4,5]decan-8-yl)pyridin-3-yl]-5-methyl-1H-pyrazole-4-carboxamide (440 mg) of Example 69 in acetic acid (8 ml) was added 1N aqueous hydrochloric acid solution (2 ml), and the mixture was stirred at 70° C. for 1 hour, and then thereto were added water and 1N aqueous sodium hydroxide solution. The precipitated solid was filtered, and then purified by silica gel chromatography (chloroform:methanol) to give the titled compound (300 mg) as a white solid. MS(ESI) m/z: 450 (M+H)+.

Example 71

1-(4-chlorophenyl)-N-[5-cyclopropyl-6-(4-methoxypiperidin-1-yl)pyridin-3-yl]-5-methyl-1H-pyrazole-4-carboxamide

[Chemical formula 125]

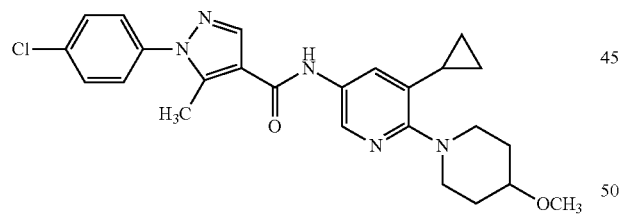

(1) To (5-amino-3-chloro-2-(4-methoxypiperidin-1-yl)pyridine (1.5 g) of Example 66(2), bis(tricyclohexylphosphine)palladium (II) dichloride (230 mg), cyclopropylboronic acid (693 mg) and tripotassium phosphate (4.6 g) were added toluene (20 ml) and water (2 ml), and the mixture was stirred at 120° C. for 2.5 hours. To the reaction solution was added Celite, and the mixture was filtered through Celite, and then washed with ethanol, chloroform, and solvent of the filtrate was distilled away under reduced pressure. The resulted residue was purified by basic silica gel chromatography (ethyl acetate:n-hexane) to give 5-amino-3-cyclopropyl-2-(4-methoxypiperidin-1-yl)pyridine (150 mg) as a yellow oil. MS(ESI) m/z: 248 (M+H)+.
(2) To a solution of 5-amino-3-cyclopropyl-2-(4-methoxypiperidin-1-yl)pyridine (150 mg) in pyridine (2.1 ml) was added 4-chlorophenyl-1H-pyrazole-4-carboxylic acid chloride (205 mg) of Example 66(3), and the mixture was stirred for 1 hour, and then thereto were added triethylamine (260 µl), water and 1N aqueous sodium hydroxide solution. The precipitated solid was filtered, and then purified by silica gel chromatography (chloroform:methanol) to give the titled compound (243 mg) as a white solid. MS(ESI) m/z: 466 (M+H)+.

Example 72 acetic acid (1-{3-chloro-5-[1-(4-chlorophenyl)-5-methyl-1H-pyrazole-4-carboxamide]pyridin-2-yl}piperidin-4-yl)ester

[Chemical formula 126]

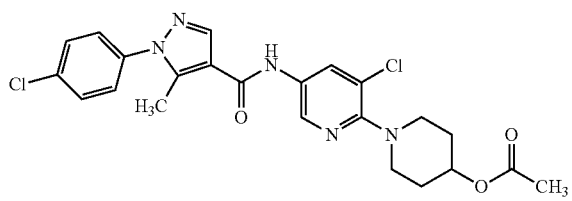

To a solution of N-[5-chloro-6-(4-hydroxypiperidin-1-yl)pyridin-3-yl]-1-(4-chlorophenyl)-5-methyl-1H-pyrazole-4-carboxamide (88 mg) of Example 36 in pyridine (3 ml) were added 4-dimethylaminopyridine (4.8 mg) and acetic anhydride (0.05 ml) at room temperature, and the mixture was stirred at the same temperature. After the completion of reaction, solvent was distilled away, and the resulted residue was diluted by water and extracted with ethyl acetate. The organic layer was dried over anhydrous sodium sulfate, and then solvent was distilled away. The resulted residue was purified by silica gel column chromatography (chloroform:methanol), and the resulted solid was suspended and washed with ethanol, and then dried with heating at 60° C. under reduced pressure to give the titled compound (65 mg) as a pale yellow solid. MS(ESI) m/z: 488 (M+H)+.

Example 73 acetic acid (1-{5-[1-(4-chlorophenyl)-5-methyl-1H-pyrazole-4-carboxamide]-3-cyclopropylpyridin-2-yl}piperidin-4-yl)ester

[Chemical formula 127]

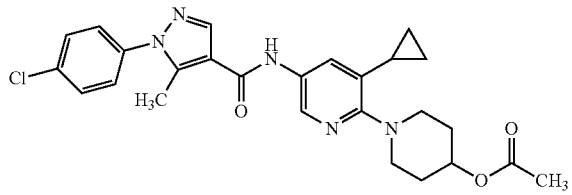

In Example 72, 1-(4-chlorophenyl)-N-[5-cyclopropyl-6-(4-hydroxypiperidin-1-yl)pyridin-3-yl]-5-methyl-1H-pyrazole-4-carboxamide (91 mg) of Example 39 was used instead of N-[5-chloro-6-(4-hydroxypiperidin-1-yl)pyridin-3-yl]-1-(4- chlorophenyl)-5-methyl-1H-pyrazole-4-carbox-

Example 74

N-{5-chloro-6-[4-(2-hydroxyethyl)piperidin-1-yl]pyridin-3-yl}-1-(4-chlorophenyl)-5-methyl-1H-pyrazole-4-carboxamide

[Chemical formula 128]

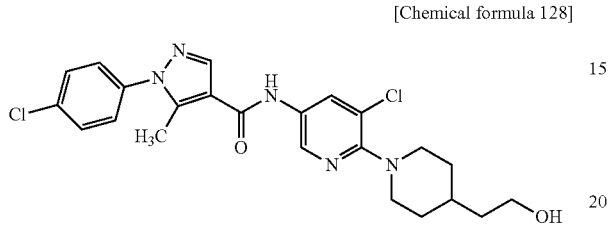

(1) To a solution of 2,3-dichloro-5-nitropyridine (600 mg) in acetonitrile (5 ml) were added 4-piperidineethanol (442 mg) and triethylamine (629 mg) at room temperature, and the mixture was stirred at 80° C. for 1 hour. The reaction solution was let stand to be cooled to room temperature, and then solvent was distilled away, and the resulted residue was diluted by adding water and extracted with ethyl acetate. The organic layer was dried over anhydrous sodium sulfate, and then solvent was distilled away to give 1-(3-chloro-5-nitropyridin-2-yl)-4-(2-hydroxyethyl)piperidine (880 mg) as a yellow viscous body. MS(ESI) (m/z): 286 (M+H)⁺.

(2) To a solution of 1-(3-chloro-5-nitropyridin-2-yl)-4-(2-hydroxyethyl)piperidine (880 mg) in methanol (50 ml) were added ferric (III) chloride (50 mg), activated carbon (2.0 g) and hydrazine 1 hydrate (1.5 ml) at room temperature, and the mixture was refluxed for 2 hours. The reaction solution was let stand to be cooled to room temperature, filtered through Celite, and solvent was distilled away. The resulted residue was diluted by adding water, and extracted with chloroform. The organic layer was dried over anhydrous sodium sulfate, and then solvent was distilled away to give 1-(5-amino-3-chloropyridin-2-yl)-4-(2-hydroxyethyl)piperidine (850 mg) as a purple solid. MS(ESI) (m/z): 256 (M+H)⁺.

(3) To a solution of 1-(4-chlorophenyl)-5-methyl-1H-pyrazole-4-carboxylic acid (100 mg) of Reference example 6 in dichloromethane (15 ml) were added oxalyl chloride (0.132 ml) and N,N-dimethylformamide (catalytic amount) at room temperature, and the mixture was stirred at room temperature for 3 hours, and then solvent and excess oxalyl chloride were distilled away. To the resulted residue was added toluene (5.0 ml), and then thereto was added a solution of 1-(5-amino-3-chloropyridin-2-yl)-4-(2-hydroxyethyl)piperidine (98.2 mg) in pyridine (15 ml), and the mixture was stirred at room temperature for 3 hours. After the completion of reaction, to the mixture was added 1N aqueous sodium hydroxide solution, and the mixture was extracted with chloroform. The organic layer was washed with saturated saline, dried over anhydrous sodium sulfate, and then solvent was distilled away. The resulted residue was purified by silica gel column chromatography (chloroform:methanol), and the resulted solid was washed with ethanol and dried with heating at 60° C. under reduced pressure to give the titled compound (102 mg) as a yellow solid. MS(ESI) m/z: 474 (M+H)⁺.

Example 75

N-{6-[4-(1-hydroxy-1-methylethyl)piperidin-1-yl]-5-methylpyridin-3-yl}-2-[4-(trifluoromethyl)phenyl]-1H-imidazole-4-carboxamide

[Chemical formula 129]

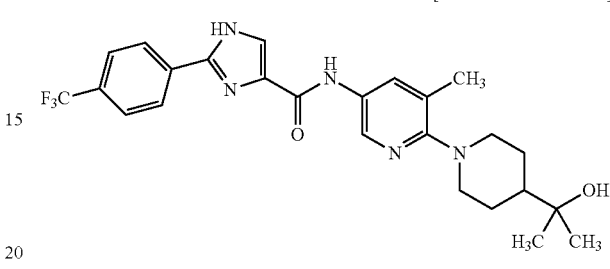

A solution of 1-[1-(5-amino-3-methylpyridin-2-yl)piperidin-4-yl]-1-methylethyl-1-ol (0.20 g) of Example 46(2), 2-[4-(trifluoromethyl)phenyl]-1H-imidazole-4-carboxylic acid (0.21 g) of Reference example 24, 1-(3-dimethylaminopropyl)-3-ethylcarbodiimide hydrochloride (0.17 g) and 1-hydroxybenzotriazole (0.12 g) in N,N-dimethylformamide (1.6 ml) was stirred at room temperature for 2 hours. After the completion of reaction, to the reaction solution was added water (4 ml), and the mixture was extracted with ethyl acetate. The organic layer was concentrated, and the resulted residue was purified by silica gel column chromatography (chloroform:methanol) to give the titled compound (0.32 g) as a pale yellow solid. MS(ESI) m/z: 488 (M+H)⁺.

Example 76

N-{6-[4-(1-hydroxy-1-methylethyl)piperidin-1-yl]-5-methylpyridin-3-yl}-3-methyl-2-[4-(trifluoromethyl)phenyl]-3H-imidazole-4-carboxamide

[Chemical formula 130]

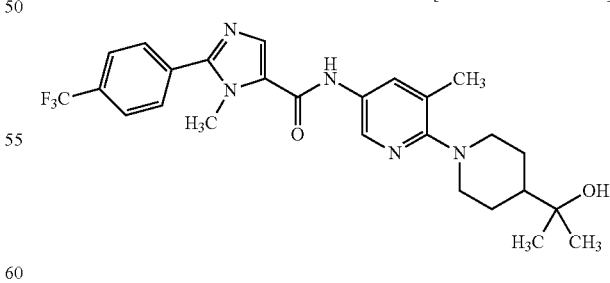

In Example 75, 3-methyl-2-[4-(trifluoromethyl)phenyl]-3H-imidazole-4-carboxylic acid (0.23 g) of Reference example 25 was used instead of 2-[4-(trifluoromethyl)phenyl]-1H-imidazole-4-carboxylic acid to be reacted and treated in a similar manner to give the titled compound (0.26 g) as a pale brown solid. MS(ESI) m/z: 502 (M+H)⁺.

Example 77

N-{6-[4-(1-hydroxy-1-methylethyl)piperidin-1-yl]-5-methylpyridin-3-yl}-5-methyl-1-[5-(trifluoromethyl)pyridin-2-yl]-1H-[1,2,3]triazole-4-carboxamide

[Chemical formula 131]

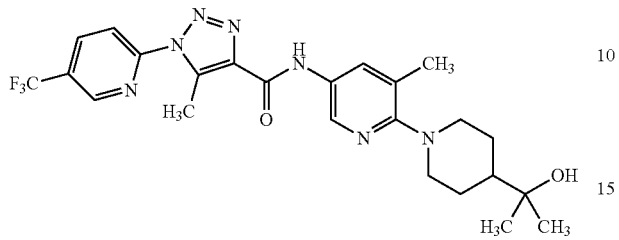

In Example 75, 5-methyl-1-[5-(trifluoromethyl)pyridin-2-yl]-1H-[1,2,3]triazole-4-carboxylic acid (0.23 g) of Reference example 26 was used instead of 2-[4-(trifluoromethyl)phenyl]-1H-imidazole-4-carboxylic acid to be reacted and treated in a similar manner to give the titled compound (0.30 g) as a pale yellow solid. MS(ESI) m/z: 504 (M+H)$^+$.

Example 78

5-(4-chlorophenyl)-N-{6-[4-(1-hydroxy-1-methylethyl)piperidin-1-yl]-5-methylpyridin-3-yl}thiophene-2-carboxamide

[Chemical formula 132]

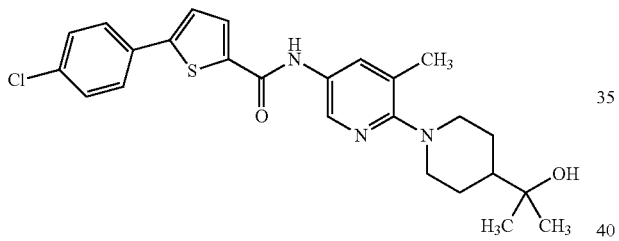

In Example 75, 5-(4-chlorophenyl)thiophene-2-carboxylic acid (0.11 g) was used instead of 2-[4-(trifluoromethyl)phenyl]-1H-imidazole-4-carboxylic acid to be reacted and treated in a similar manner to give the titled compound (0.19 g) as a pale yellow solid. MS(ESI) m/z: 470 (M+H)$^+$.

Example 79

2-(4-chlorophenyl)-N-{6-[4-(1-hydroxy-1-methylethyl)piperidin-1-yl]-5-methylpyridin-3-yl}thiophene-4-carboxamide

[Chemical formula 133]

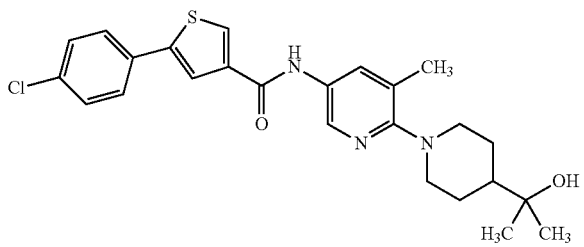

In Example 75, 2-(4-chlorophenyl)thiophene-4-carboxylic acid (0.20 g) of Reference example 27 was used instead of 2-[4-(trifluoromethyl)phenyl]-1H-imidazole-4-carboxylic acid to be reacted and treated in a similar manner to give the titled compound (0.17 g) as a pale yellow solid. MS(ESI) m/z: 470 (M+H)$^+$.

Example 80

4-(4-chlorophenyl)-N-{6-[4-(1-hydroxy-1-methylethyl)piperidin-1-yl]-5-methylpyridin-3-yl}thiophene-2-carboxamide

[Chemical formula 134]

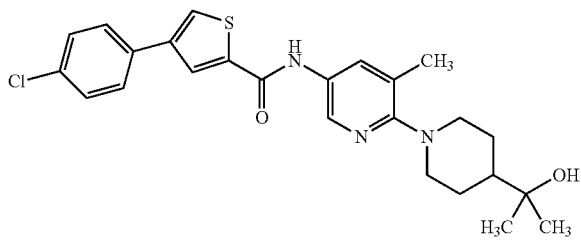

In Example 75, 4-(4-chlorophenyl)thiophene-2-carboxylic acid (0.099 g) was used instead of 2-[4-(trifluoromethyl)phenyl]-1H-imidazole-4-carboxylic acid to be reacted and treated in a similar manner to give the titled compound (0.15 g) as a pale yellow solid. MS(ESI) m/z: 470 (M+H)$^+$.

Example 81

2-(4-chlorophenyl)-N-{6-[4-(1-hydroxy-1-methylethyl)piperidin-1-yl]-5-methylpyridin-3-yl}thiazole-5-carboxamide

[Chemical formula 135]

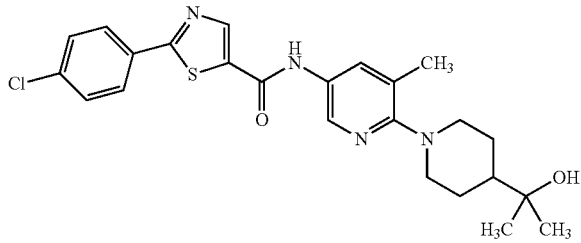

In Example 75, 2-(4-chlorophenyl)thiazole-5-carboxylic acid (0.20 g) of Reference example 28 was used instead of 2-[4-(trifluoromethyl)phenyl]-1H-imidazole-4-carboxylic acid to be reacted and treated in a similar manner to give the titled compound (0.27 g) as a pale yellow solid. MS(ESI) m/z: 471 (M+H)$^+$.

Example 82

2-(4-chlorophenyl)-N-{6-[4-(1-hydroxy-1-methyl-ethyl)piperidin-1-yl]-5-methylpyridin-3-yl}thiazole-4-carboxamide

[Chemical formula 136]

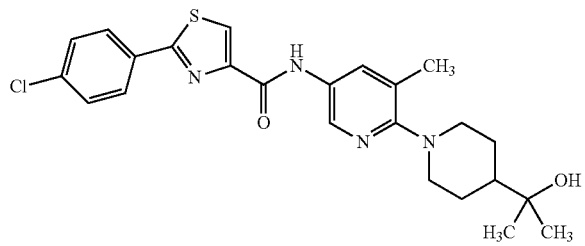

In Example 75, 2-(4-chlorophenyl)thiazole-4-carboxylic acid (0.20 g) of Reference example 29 was used instead of 2-[4-(trifluoromethyl)phenyl]-1H-imidazole-4-carboxylic acid to be reacted and treated in a similar manner to give the titled compound (0.30 g) as a pale yellow solid. MS(ESI) m/z: 471 (M+H)$^+$.

Example 83

4-(4-chlorophenyl)-N-{6-[4-(1-hydroxy-1-methyl-ethyl)piperidin-1-yl]-5-methylpyridin-3-yl}thiazole-2-carboxamide

[Chemical formula 137]

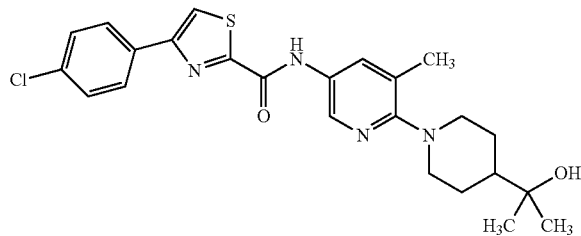

In Example 75, 4-(4-chlorophenyl)thiazole-2-carboxylic acid (0.20 g) of Reference example 30 was used instead of 2-[4-(trifluoromethyl)phenyl]-1H-imidazole-4-carboxylic acid to be reacted and treated in a similar manner to give the titled compound (0.30 g) as a yellow solid. MS(ESI) m/z: 471 (M+H)$^+$.

Example 84

5-(4-chlorophenyl)-N-{6-[4-(1-hydroxy-1-methyl-ethyl)piperidin-1-yl]-5-methylpyridin-3-yl}thiazole-2-carboxamide

[Chemical formula 138]

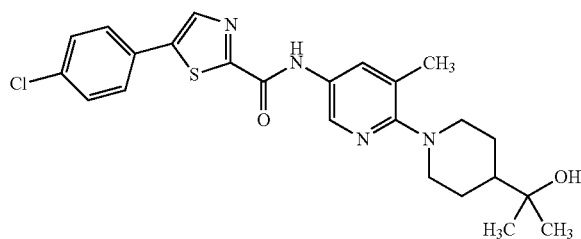

In Example 75, 4-(4-chlorophenyl)thiazole-2-carboxylic acid (0.20 g) of Reference example 31 was used instead of 2-[4-(trifluoromethyl)phenyl]-1H-imidazole-4-carboxylic acid to be reacted and treated in a similar manner to give the titled compound (0.17 g) as a yellow solid. MS(ESI) m/z: 471 (M+H)$^+$.

Example 85

2-(4-chlorophenyl)-N-{6-[4-(1-hydroxy-1-methyl-ethyl)piperidin-1-yl]-5-methylpyridin-3-yl}-2H-[1,2,3]triazole-4-carboxamide

[Chemical formula 139]

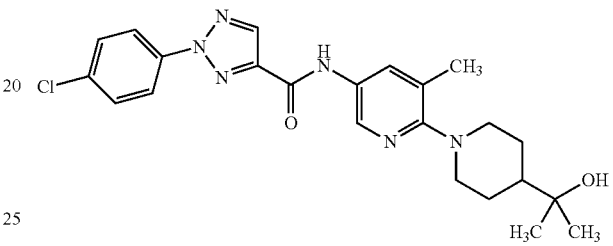

In Example 75, 2-(4-chlorophenyl)-2H-[1,2,3]triazole-4-carboxylic acid (0.10 g) of Reference example 32 was used instead of 2-[4-(trifluoromethyl)phenyl]-1H-imidazole-4-carboxylic acid to be reacted and treated in a similar manner to give the titled compound (0.069 g) as a pale brown solid. MS(ESI) m/z: 455 (M+H)$^+$.

Test Example 1

Effect on Production of IL-17 Induced when Mouse Splenocytes were Stimulated by Recombinant Mouse Interleukin-23 (rm-IL-23)

RPMI1640 media (Sigma-Aldrich) were used as a medium, to which 50 units/mL penicillin G potassium/50 μg/mL streptomycin (Gibco) and 50 mol/L 2-mercaptoethanol (Sigma-Aldrich) were added, and then thereto was added 10% of fetal calf serum (FCS; Cell Culture Technology) which was treated at 56° C. for 30 minutes to be inactivated, and the mixture was used in the Test. The test compound was dissolved in dimethylsulfoxide and then diluted with 10% FCS-containing RPMI1640 medium to a desired concentration to be used. The spleens were aseptically taken out from 6 to 7 week-old male DBA/1J mice (Charles River Japan, Inc.) and a single cell suspension of splenocytes was prepared, which was hemolyzed by hypotonic treatment with a mixed solution of 0.83% aqueous solution of ammonium chloride and Tris-HCl buffer of pH 7.65 (9:1). A cell suspension prepared by using 10% FCS-containing RPMI1640 medium was added to a flat-bottomed 96 well microtestplate (Coaster) at 2×10$^5$ cells/well. Thereto were added test compounds and rm-IL-23 (R&D systems) were diluted with a medium to 1 to 1,000 nmol/L and 1 nmol/L of the final concentration, respectively, and the mixture was cultured at 37° C., 5% carbon dioxide and 95% air for 72 hours. After completion of the culture, culture supernatant was sampled and production amounts of IL-17 therein were determined by ELISA method. After sampling the supernatant, WST-8 (Seikagaku Corporation) was added at 10 μl/well and cultured at 37° C., 5% carbon dioxide and 95% air for 4 hours. Then, absorbance (O.D.: Optical Density) at 450 nm was measured by a microplate reader and the value was adopted as an index of cell survivability. An inhibition rate was calculated according to the following formula on the basis of an average of production amounts of IL-17 and O.D. values of the well containing a test compound of each concentration.

Inhibition (%)=(1−(Average value of well with addition of test compound)/(Average value of well without addition of test compound))×100

Based on the dose-response curve obtained by plotting the inhibition rate in the longitudinal axis and the concentration in the horizontal axis, the concentration of the compound which inhibits the level to 50% of the value of the control group ($IC_{50}$) (nmol/L) was determined by linear regression analysis. The results were shown in the following table.

TABLE 3

| Example No. | IC50 (nmol/L) |
|---|---|
| 9 | 331 |
| 15 | 292.7 |
| 16 | 264 |
| 18 | 221.8 |
| 19 | 212.6 |
| 22 | 194.2 |
| 23 | 193.1 |
| 24 | 180 |
| 25 | 161.3 |
| 26 | 173 |
| 27 | 171 |
| 28 | 170 |
| 29 | 168 |
| 30 | 174.8 |
| 31 | 158 |
| 32 | 155 |
| 33 | 153 |
| 34 | 151 |
| 35 | 150 |
| 36 | 142 |
| 37 | 140.2 |
| 38 | 140 |
| 39 | 136.1 |
| 40 | 116 |
| 41 | 112 |
| 42 | 105.9 |
| 43 | 102.3 |
| 44 | 74.9 |
| 45 | 72.5 |
| 46 | 60.8 |
| 47 | 57.9 |
| 48 | 56.4 |
| 49 | 54.7 |
| 50 | 54.1 |
| 51 | 53.5 |
| 52 | 53.1 |
| 53 | 51.8 |
| 54 | 51 |
| 55 | 49.6 |
| 56 | 44.4 |
| 57 | 36.7 |
| 58 | 33 |
| 59 | 31.8 |
| 60 | 30.4 |
| 61 | 19.4 |
| 62 | 17 |
| 63 | 15.6 |
| 64 | 12 |
| 65 | 5.35 |
| 70 | 205 |
| 74 | 87.7 |
| 75 | 109 |
| 76 | 30.4 |
| 78 | 15.6 |
| 79 | 43.6 |
| 80 | 185 |

TABLE 3-continued

| Example No. | IC50 (nmol/L) |
|---|---|
| 81 | 66.8 |
| 82 | 91.1 |
| 85 | 67.6 |
| blank | blank |

Test Example 2

Effects on hERG Current

Dimethylsulfoxide was used as a vehicle, and hERG-expressed HEK 293 cells (Cytomyx) were used as test cells. Test cells were once cultured and subdivided and were stored under frozen condition in liquid nitrogen. In the study, thawed and subcultured cells having less than 30 of the passage number were used. Test cells were cultured in a carbon dioxide gas incubator BNP-110M (Tabai Espec Corp.) at 37±1° C. and 5.0±0.5% of carbon dioxide concentration. The component of culture medium was basically MEM (Minimum Essential Medium) supplemented with 10 vol % fetal bovine serum (non-activated), 1 mmol/L sodium pyruvate, 0.1 mmol/L non-essential amino acid and 100 U/mL penicillin/100 μg/mL streptomycin. To select gene-expressing cells, 400 μg/mL G418 Sulphate (Invitrogen) was added to the culture medium. In the dishes for the measurement, the medium which did not contain G418 Sulphate (Invitrogen) was used. A manufacturer of the culture solution is Invitrogen Corporation.

As to seeding of cells for measurement, subcultured cells which became confluent were treated with 0.25% trypsin-solution containing 1 mmol/L EDTA (Invitrogen) to remove therefrom, and seeded on dishes overlaid with sterilized collagen-coated cover glass (Iwaki, AGC Techno Glass Co., LTD). The medium was exchanged appropriately, including the day of measurement.

A perfusion method was carried out for an application route. Test cells were perfused (perfusion speed: approximately 4 mL/min) with an external solution containing specified concentrations of test compounds (component of external solution: 137 mmol/L of sodium chloride, 4 mmol/L of potassium chloride, 10 mmol/L of HEPES, 1.8 mmol/L of calcium chloride, 1 mmol/L of magnesium chloride and 10 mmol/L of glucose; adjusted to pH 7.4±0.1 with sodium hydroxide solution). When no effects were observed until 4 minutes after switching to a test compound solution, the next different concentration of the test compound was perfused. When effects were observed, the perfusion was continued until the maximum response was observed. The maximum perfusion time for lower concentrations of test compound was set for 10 minutes even when effects were observed. The data were obtained from one experiment or more and the cells which were gently incubated in a carbon dioxide incubator after seeding and attached to cover glasses were used for the measurement.

A whole-cell clamping method was applied to the measurement. Test cells were perfused (perfusion speed: approximately 4 mL/min) with an external solution (component of external solution: 137 mmol/L of sodium chloride, 4 mmol/L of potassium chloride, 10 mmol/L of HEPES, 1.8 mmol/L of calcium chloride, 1 mmol/L of magnesium chloride and 10 mmol/L of glucose; adjusted to pH 7.4±0.1 with sodium hydroxide solution). A glass electrode with a resistance of 2 to 6 MΩ, filled with an internal solution (component: 130 mmol/L of potassium chloride, 1 mmol/L of magnesium chloride, 5 mmol/L of EGTA, 10 mmol/L of HEPES and 5 mmol/L of ATP, adjusted to pH 7.2±0.1 with potassium hydroxide solution) was used. After rupturing cell membrane with glass electrode, the cell membrane voltage was held at −80 mV by using patch clamp amplifier (EPC8, HEKA) via a patch clamp software (pCLAMP9 [Axon CNS], Molecular Devices). As illustrated below, a test pulse of +20 mV for 1.5 seconds and −40 mV for 1.5 seconds was given once every 15 seconds. One minute or more after obtaining 500 pA or higher peak value of the stable tail currents, test compounds were applied. Test cells and the cell-seeded cover glass were changed every treatment. Temperature of the fluid in a perfusion fluid tank was 24±2° C.

<Test Pulse>

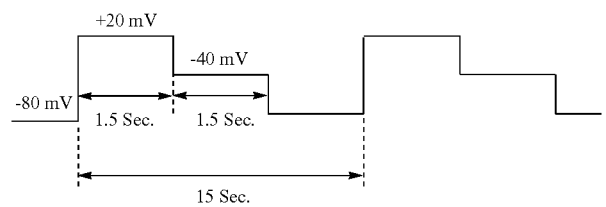

The obtained current was recorded on a computer by using a patch clamp software via a patch clamp amplifier. An evaluation item was a tail peak current.

A tail peak current was analyzed using analyzing software (Clampfit 9 [Axon CNS], MolecularDevices). Two pulses of before application and after completion of exposure of test compound solution in each concentration were analyzed, and peak values of the tail current were determined. Each inhibition ratio for each data was determined according to the following equation:

Inhibition (%)=100−[Peak tail current after perfusion/Peak tail current before perfusion]×100

An inhibition ratio of each test compound at 1 μM of concentration is shown in the following table.

TABLE 4

| Example No. | Inhibition ratio (%) |
|---|---|
| 39 | 8.1 |
| 43 | 9.4 |
| 44 | 2 |
| 45 | 4.2 |
| 47 | 32.7 |
| 49 | 40.5 |

Test Example 3

Effect on Type II Collagen-Induced Arthritis in DBA/1J Mice

An emulsion was prepared by mixing 200 μg of bovine type II collagen (purchased from collagen Gijyutsu Kenshuukai) with Freund's complete adjuvant (Sigma-Aldrich) containing killed *Mycobacterium tuberculosis* H37Ra, and arthritis was induced by immunization through subcutaneous administration of the emulsion to the tail of 6 to 7 week-old male DBA/1J mouse (Charles River Japan, Inc.), followed by booster immunization three weeks after the first immunization by administration of the same amounts of the emulsion prepared in a similar way. Test compound was suspended or dissolved in 0.5% carboxymethylcellulose (Sigma-Aldrich) and repeatedly administered orally once a day at a dose of 1 to 10 mg/kg body weight using an oral sonde for three weeks from the day of booster immunization. In this model, the symptom of arthritis of the limbs was each evaluated according to the following evaluation criteria of 0 to 4 scores: 1, No change; 1, edema in only one joint; 2, edema in two or more joints, or mild edema of the entire limb; 3, severe edema of the entire limb; 4, severe edema of the entire limb and ankylosis and immovability of joint. The score of arthritis of each mouse was expressed as the total of the scores of the limbs (Maximum: 16 points). On the next day of the final administration, soft X-ray photograph of the

[Chemical formula 140]

limbs was taken with soft X-ray equipment (Omic), and the level of joint destruction was evaluated by observation under a microscope. In each finger of the limbs the score of joint destruction in each mouse was judged in the total of scores for each finger of limbs (Maximum: 20) as 0 when no joint destruction was found, and as 1 when one or more destruction was found. The arthritis score and joint destruction score were expressed as the average value and standard error for each group (n=6 to 9). Only a vehicle was administered in a control group, and statistical analysis was performed by Dunnett's multiple comparison test, in which the case was judged as significant when the p value was less than 0.05. The typical compounds showed a significant inhibitory effect on arthritis in a dose of the following table.

TABLE 5

Effective dose showing arthritis-inhibiting activity of each example

| Example No. | Effective Dose |
|---|---|
| 18 | 3 mg/kg |
| 39 | 3 mg/kg |
| 44 | 3 mg/kg |
| 45 | 10 mg/kg |

Test Example 4

Evaluation of Hepatocyte Cytotoxicity Using HepG2 Cells

A culture solution was prepared by adding 10% Fetal Bovine Serum (FBS: treated to be inactivated under the condition of 56° C., 30 minutes, Invitrogen, 10082-147), 0.1 mM Non-Essential Amino Acids (NEAA: Invitrogen, 11140-050), 1 mM sodium pyruvate (PyNa: Invitrogen, 11360-070) to Eagle's MEM medium (Invitrogen, 11875-093) and was used after warming to 37° C. before using.

HepG2 cell line (DS Pharma Biomedical) derived from human hepatoma in logarithmic growth phase were used. The number of cells subjected to subculturing was 1 to $5\times10^6$ cell/15 mL in a 75 cm² cultivation flask, and cells were subcultured about every 1 week depending on the condition of cells. In subculturing, cells were rinsed with D-PBS (−) (invitrogen, 14190-144) (10 mL), then thereto was added 0.25% Trypsin-1 mM EDTA (Invitrogen, 25200-056) (1 mL), and the mixture was treated for 10 minutes (37° C., 5% $CO_2$), then thereto was added culture solution (9 mL), and the mixture was collected and centrifuged (1000 rpm×5 minutes, 4° C.). The number of cells were counted by dyeing with 0.4% trypan blue solution (Invitrogen, 15250-061), and then cells were diluted with culture solution to be a specific number of cells and incubated under the condition of 37° C., 5% $CO_2$.

As to a cell seeding, HepG2 cells which were incubated in a 75 cm² flask were rinsed with D-PBS (−) (10 mL), and then thereto was added 0.25% Trypsin-1 mM EDTA (1 mL), and the mixture was treated for 10 minutes (37° C., 5% $CO_2$). Thereto was added additional culture solution (9 mL), and the mixture was collected in a 50 mL centrifuge tube to be centrifuged (1000 rpm×5 minutes, 4° C.). A supernatant was removed, and the residual cells were suspended by additional culture solution and sufficiently single-celled by pipetting. After dyeing with 0.4% trypan blue, the number of cells were counted by using a cell counting chamber, and a suspended cell was prepared in a specified cell density (In case of 24-hour exposure: $1\times10^5$, in case of 48-hour exposure: $5\times10^4$ cells/mL). The 100 µL of cell suspension was added per 1 well (n=3, 24 hours: $1\times10^4$, 48 hours: $5\times10^3$ cells/100 µL/well) of 96 well Clear bottom black microplate (Corning, 3603), and then the mixture was pre-incubated for about 24 hours under the condition of 37° C., 5% $CO_2$.

Stock solutions of test compounds were prepared in a 200-fold concentration of the desired maximum concentration to be homogenized with optional ultrasonication. These stock solutions were preserved at −20° C. Before using, a stock solution was thawed, and diluted with DMSO to be concentrations of 20 mM to 20 µM (common ratio of 3, 7 concentrations in total), and then it was diluted with culture solution in 100-fold to prepare a culture solution containing test compounds in a 2-fold concentration. Thus, the upper limit of the final concentration of DMSO in culture solution was in principle 0.5% (v/v).

A vehicle control group and a positive control group were set with each measurement plate. Chlorpromazine (Wako Pure Chemical Industries, Ltd., 033-10581) was used as a positive control agent (final concentration 24 hours: 20 µM, 48 hours: 15 µM). 20 mM stock solution was thawed, and then diluted with culture solution, and chlorpromazine-containing culture solution was prepared in 2-fold concentration.

As to the treatment of test compounds, a culture solution (100 µL) containing a test compound or a positive control agent and a culture solution (100 µL) containing vehicle were added to each specified well. A culture solution (200 µL) was added to blank (without cells) well. Thus, total amounts of culture solution of each well were 200 µL, and the final concentration of test compounds was 100 µM to 0.1 µM (common ratio of 3, 7 concentrations in total).

Incubation was carried out under the condition of 37° C., 5% $CO_2$ for 24 or 48 hours. After incubation, it was observed by an inverted microscope (Nikon, TMS) whether test compounds in media were precipitated.

After incubation for a specified time, a half of culture solution (100 µL/well) was removed by multipipette to be discarded. The plate was placed at room temperature for about 30 minutes, and then CellTiter-Glo™ reagent (Promega, H7571) (100 µL) was added to each well and the mixture was stirred at room temperature with light shielding for 2 minutes. Then, the plate was placed at room temperature with light shielding for about 10 minutes. An emission intensity was measured by a microplate reader (ParkinElmer, ARVO SX1420 multilabelcounter).

A cell survival rate was calculated by the following equation, and $IC_{50}$ values were calculated by using SOFT-max Pro4.0 (4-Parameter curve fit, MDS Analytical Technologies).

Cell survival rate: % Cell viability=[luminesence (test compound)−luminesence (blank)]÷[luminesence (control)−luminesence (blank)]×100

Each cell survival rate in 1 mmol/L for each example is shown in the following table. A cell survival rate in 10 mol/L for Example 39 was 65.8%.

TABLE 6

| Example No. | Survival rate (%) |
|---|---|
| 39 | 107.1 |
| 43 | 117.8 |
| 44 | 95.8 |
| 45 | 92.5 |
| 47 | 99.8 |
| 49 | 102.3 |

Test Example 5

Genotoxicity Test Using *Salmonella typhimurium* TA104 Strain Carrying a Reporter Gene Under the Control of DNA Repair Enzyme recN (Vitotox Test)

(1) Preparation of Agents for Stock of Tester Strain, Media for Pre-Incubation, Media for Test and Enhancer Reagent ($CaCl_2$ Aqueous Solution):

To prepare agents for stock of tester strain, Amp solution (50 mg/mL) and Tet solution (10 mg/mL) were prepared, and then LB-agar plate (35 mg/mL+Amp (100 µg/mL)+Tet (20 g/mL)) was prepared, and LB medium (20 mg/mL+Amp (100 µg/mL)+Tet (20 µg/mL)) was prepared. Then, LB medium for pre-incubation (10 mg/mL), LB medium for test (4 mg/mL) and enhancer reagent (50 mg ($CaCl_2.H_2O$)/mL) were prepared.

(2) Preparation of Stock of Tester Strains Used for Genox and Cytox:

Freezing stock of bacterial strain was thawed to be streaked on LB-agar plate, and incubated in an incubator (TITEC, BIO-SHAKER BR-15) at 37° C. overnight. A single colony was scratched to be inoculated on LB medium for the stock, and incubated in an incubator (TITEC, BIO-SHAKER BR-15) at 37° C., 160 rpm. To a bacterial culture solution of OD590=about 0.4-0.8 was mixed DMSO, and the mixture was refrigerated (−80° C.).

(3) Pre-Incubation of Genox and Cytox:

Bacterial culture solution of each stain was diluted with medium for pre-incubation (−Enhancer Reagent), and then the diluted culture solution was inoculated on medium for pre-incubation (+Enhancer Reagent). It was incubated in an incubator (TITEC, BIO-SHAKER BR-15) at 37° C., 160 rpm.

(4) Vitotox Test:

OD590 of pre-incubated culture solution was confirmed by a spectrophotometer (GE Health Bioscience, NovaSpec Plus). In case that OD590 was within 0.4-0.8, the incubation was terminated and the culture solution was stored under ice cooling until using. In case that OD590 was less than 0.4-0.8, the incubation was carried out again. In case that OD590 was over 0.8, it was not used for the following test.

A solution for positive control was prepared as below. 4-Nitroquinoline N-oxide (4NQO): 0.04, 0.02, 0.01, 0.005, 0.0025 µg/mL (final concentration: 4, 2, 1, 0.5, 0.25 ng/mL). Benzo[a]pyrene (B[a]P): 0.04, 0.02, 0.01, 0.005, 0.0025 mg/mL (final concentration: 4, 2, 1, 0.5, 0.25 g/mL). Then, a solution for test compound was prepared. The solution for test compound was observed whether a precipitate was found. When the test compound was completely dissolved, the highest concentration as prepared was determined to be a highest dose, and when a precipitate was found, a homogeneous suspension which was able to be pipetted was determined to be a highest dose.

After a fluorescent and luminescent photometer (Thermo Labsystem, Fluoroskan Ascent FL), plate and medium for test were set up, Genox and Cytox reaction solutions were prepared as below. Dilution factor as well as requisite amounts for medium for test, pre-incubation strain solution, Enhancer Reagent and S9 mix were calculated so that OD590 was set as about 0.03 for each culture solution. 40 uL of Enhancer Reagent was required for 10 mL of the total amount of medium for preparation and pre-incubated culture solution, and 1 mL of S9 mix was required for 9 mL of the total amount of medium for test and pre-incubation culture solution. The required amounts of medium for test, pre-incubation culture solution and Enhancer Reagent were mixed. Genox and Cytox reaction solutions with the required amount of S9 mix (+S9), and Genox and Cytox reaction solutions without it (—S9) were prepared.

Well plates were separately arranged for control group, test compound group and positive control group, and vehicle control solution, solution for test compound and solution for positive control were separately injected in the wells, respectively.

Temperature in the fluorescent and luminescent photometer was confirmed as 30° C., and Genox and Cytox reaction solutions were added by an automatic pipettor (Biotech, Multidispenser EDR-384SII) or 384 12ch pipette. The above well plates were set up in the fluorescent and luminescent photometer, and the amount of luminescence in each well (Relative Light Unit, referred to be as RLU hereinafter) was started to be measured. The amount of luminescence was determined at 17 points every 15 minutes.

(5) Calculating Method for Each Parameter

Each parameter was calculated as follows.

Max S/N ratio and Genox/Cytox ratio of Genox and Cytox at each dose of 4NQO and B[a]P were calculated. Max RLU of Genox and Cytox of vehicle control was calculated. Max S/N ratio and Genox/Cytox ratio of Genox and Cytox at each dose of test compound were calculated.

S/N ratio: Each RLU/Vehicle RLU

Genox/Cytox ratio: Genox Max S/N ratio/Cytox Max S/N ratio (6) Judgment Criteria for Test Validity and Decision for Genotoxicity:

When Genox/Cytox ratio for positive control: 4NQO (4 ng/mL) and B[a]P (4 µg/mL) was 1.5 or more, and Max RLU of Genox and Cytox for vehicle control was above the criteria (set based on background data), it was determined that test was established.

The following conditions A to C were comprehensively considered, and the test compound was determined as positive when it was recognized that the compound has DNA-damaging activity.

A. DNA Damages

If Genox/Cytox ratio is 1.5 or more and it increases in a dose-dependent manner in at least 3 or more doses, the compound is judged to have DNA-damaging activity.

If Genox/Cytox ratio is 1.5 or more but both of Genox and Cytox are high values, it is not evaluated.

If Genox/Cytox ratio is 1.5 or more but Max S/N ratio of Genox is around 1, it is not evaluated.

B. Cytotoxicity

If S/N ratio decreases to 0.8 or below, it is not evaluated due to cytotoxicity. However, in case that the low value of S/N ratio is clearly recognized as artifact in comparison with RLUs of all other data, a retest is carried out.

C. Criteria for Carrying Out a Retest

If Genox/Cytox ratio is over 1.5 at only 1 dose, a retest with narrowing dose ranges is carried out.

If 4 or more doses of a dose with S/N ratio>0.8 cannot be expected in either Genox or Cytox, a retest with reducing doses is carried out.

If it is recognized that S/N ratio of Genox slightly increases in a lower dose and shows inverse correlation with doses, a retest with reducing doses is carried out.

If high S/N ratios are obtained in both Genox and Cytox, a retest with reducing doses is carried out.

According to the above test method, genotoxicity of a metabolite of Example 39, 1-(5-amino-3-cyclopropylpyridin-2-yl)piperidin-4-ol, was evaluated to give a negative result.

Test Example 7

Single Dose Toxicity Study in Dogs

The study was carried out with TOYO beagles (KITAYAMA LABES CO., LTD., Hongou farm), four dogs per each sex. They were 5-month old on arrival at testing facility, and were 10-month old when started to be administered. Basal diet was 300 g/day, DS-A (Oriental Yeast Co., Ltd.), and drinking water was tap water. Allocation to the groups was carried out so that an animal number was allocated in order of quarantine number for males and females respectively whose clinical signs and results of clinical laboratory test were considered to be normal.

As to a dosing suspension, 0.5 w/v % HPMC aqueous solution was used as a vehicle, the required amounts of test compound were pre-weighed for each dose group, and it was prepared in a specified concentration with mortar and pestleon the day of administration. Dose volume was 5 mL/kg (calculated on the basis of body weight measured on the day of administration). As to dosing procedures, a custom-ordered catheter (Natsume Seisakusho Co., Ltd.) of which a tip was in a capsule shape was connected to 50 mL of disposable syringe (Terumo), and a single dose compulsory oral administration was carried out.

Group design was as follows.

TABLE 7

| Group | Dose level (mg/kg) | Dose volume (mL/kg) | Concentration of dosing suspension (mg/mL) | Number of animals | |
|---|---|---|---|---|---|
| | | | | Male | Female |
| 1* | 0 | 5 | 0 | 1 | 1 |
| 2 | 10 | 5 | 2 | 1 | 1 |
| 3 | 30 | 5 | 6 | 1 | 1 |
| 4 | 100 | 5 | 20 | 1 | 1 |

*Vehicle: 0.5 w/v % HPMC aqueous solution

As to dose level setting, low dose was set as approximately 3- to 10-fold dose level in comparison with an effective dose in CIA mice model. The middle and high doses were set based on a common ratio of about 3 from low dose level.

Items to be observed and measured were as follows.

A clinical sign was observed before administration and during TK blood sampling on the day of administration, and once in the morning every day on the day other than administration. Body weight was measured in the pre-dosing term (−5th day, −1st day), on the day of administration and on the next day after administration.

Feeding was carried out every day, and food consumption (g/day) was calculated from the remaining food in the next morning after feeding. Feeding on the day of administration was carried out after completion of blood sampling 4 hours after administration. The remaining food was collected in the evening (17:00 to 19:00) one day before carrying out clinical laboratory tests for hematology and blood chemistry (−5th day, 1st to 3rd day).

In terms of the hematological test, the following items were measured for all animals 4 days before administration and 24 hours after administration (corresponding time zones during the term of pre-administration) by using about 1 mL blood samples collected from cephalic vein with a blood collection tube containing EDTA-2K (Venoject II vacuum blood collection tube, Terumo).

Items to be measured: erythrocyte counts (RBC), hemoglobin concentration (Hb), hematocrit value (Ht), mean corpuscular volume (MCV), mean corpuscular hemoglobin content (MCH), mean corpuscular hemoglobin concentration (MCHC), reticulocyte ratio, reticulocyte counts, platelet counts (PLT), leukocyte counts (WBC), percentages and counts according to types of white blood cells.

In terms of the blood chemical test, the following items were measured for all animals 4 days before administration, 24 hours after administration, 48 hours after administration and 72 hours after administration (corresponding time zones during the term of pre-administration) by using serum which was obtained by collecting about 3 mL of blood from cephalic vein with a blood collection tube containing agents for serum separation (Venoject II vacuum blood collection tube, Terumo), followed by separating by centrifugation (3,000 rpm, about 4° C., 10 minutes).

AST (GOT), ALT (GPT), alkaline phosphatase (ALP), total bilirubin (TBil), total protein (D_TP), albumin (D_Alb), albumin/globulin ratio (A/G: calculated value), urea nitrogen (UN), creatinine (CRE), blood glucose (Glu), total cholesterol (TC), phospholipid (PL), triglyceride (TG), calcium (Ca), inorganic phosphorus (IP), sodium (Na), potassium (K), chlorine (Cl)

In terms of the TK measurement, about 1 mL blood was collected from cephalic vein with a blood collection tube containing EDTA-2K (Venoject II vacuum blood collection tube, Terumo) for all animals 1, 2, 4, 8, 24, 48 and 72 hours after administration. For plasma obtained after administration, concentrations for test compounds in the plasma were measured by LC/MS/MS method. Cmax, AUC 0-24, AUC 0-infinity and Tmax were calculated.

According to the above method, Example 39 was assessed, but no changes caused by administration were found in any doses in terms of clinical signs, body weight, food consumption, clinical laboratory tests for hematology and blood chemistry including parameters involved in hepatic injury such as ALT, AST and TBil.

INDUSTRIAL APPLICABILITY

The compound (I) of the present invention or a pharmacologically acceptable salt thereof has a superior inhibitory activity on production of cytokines in T-cell and can be a useful medicament as a therapeutic agent for various diseases, particularly rheumatoid arthritis, autoimmune disease, inflammation and allergy disease.

The invention claimed is:

1. A compound of formula (I):

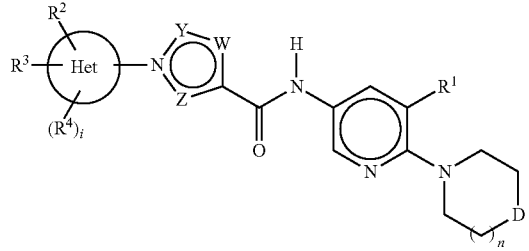

wherein X is N, or C,
Y is N, N—$R^Y$, S, or C—$R^Y$,
Z is N, N—$R^Z$, S, or C—$R^Z$,
W is N, N—$R^W$, S, or C—$R^W$,
provided that at least one of X, Y, Z, W is N or S,
$R^Y$, $R^Z$ and $R^W$ are each independently selected from hydrogen atom, alkyl group, haloalkyl group, or cycloalkyl group,
$R^1$ is cycloalkyl group,
n is an integer of 0 to 2,
Het is cycloalkyl group, aryl group, heterocycle group, or heteroaryl group,
$R^2$, $R^3$ and $R^4$ are each independently selected from hydrogen atom, halogen atom, cyano group, hydroxy group, alkyl group, haloalkyl group, alkoxy group, or cycloalkyl group,
i is an integer of 0 to 3,
D is any one of groups of formulae:

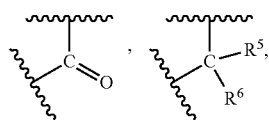

$R^5$ and $R^6$ are each independently selected from hydrogen atom, hydroxy group, cyano group, optionally substituted alkyl group, optionally substituted alkoxy group, optionally substituted cycloalkyl group, -L-$NR^{7a}R^{7b}$, -L-$NR^{7a}$—CO—$R^{7b}$, -L-CO—$NR^{7a}R^{7b}$, or -L-O—CO—$R^{7c}$ [in which $R^{7a}$ and $R^{7b}$ are each independently selected from hydrogen atom or alkyl group, $R^{7c}$ is alkyl group or phenyl group, L is a bond, or —$(CR_AR_B)_j$— (in which j is an integer of 1 to 4, $R_A$ and $R_B$ are each independently selected from hydrogen atom or alkyl group)], or
$R^5$ and $R^6$ are optionally combined with each other to form optionally substituted cycloalkyl group, or optionally substituted heterocycle group, or a pharmacologically acceptable salt thereof.

2. The compound of claim 1, wherein Het is aryl group or heteroaryl group, or a pharmacologically acceptable salt thereof.

3. The compound of claim 1, wherein n is 1, or a pharmacologically acceptable salt thereof.

4. The compound of claim 1, wherein D is a group of formula:

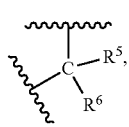

or a pharmacologically acceptable salt thereof.

5. The compound of claim 1, wherein X is N, or a pharmacologically acceptable salt thereof.

6. A compound of formula (I)a:

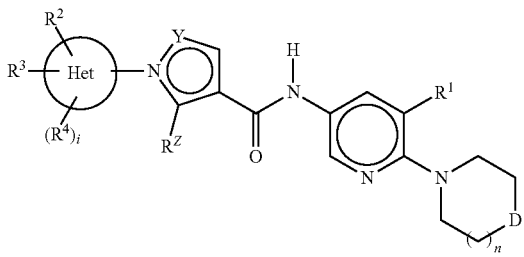

wherein Y is N or C—$R^Y$, $R^Y$ and $R^Z$ are each independently selected from hydrogen atom, alkyl group, haloalkyl group, or cycloalkyl group, $R^1$ is cycloalkyl group, n is an integer of 0 to 2, Het is cycloalkyl group, aryl group, heterocycle group, or heteroaryl group, $R^2$, $R^3$ and $R^4$ are each independently selected from hydrogen atom, halogen atom, cyano group, hydroxy group, alkyl group, haloalkyl group, alkoxy group, or cycloalkyl group, i is an integer of 0 to 3, D is any one of formulae:

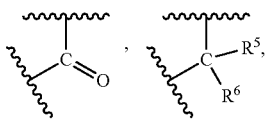

$R^5$ and $R^6$ are each independently selected from hydrogen atom, hydroxy group, cyano group, optionally substituted alkyl group, optionally substituted alkoxy group, optionally substituted cycloalkyl group, -L-$NR^{7a}R^{7b}$, -L-$NR^{7a}$—CO—$R^{7b}$, -L-CO—$NR^{7a}R^{7b}$, or -L-O—CO—$R^{7c}$ [in which $R^{7a}$ and $R^{7b}$ are each independently selected from hydrogen atom or alkyl group, $R^{7c}$ is alkyl group or phenyl group, L is a bond, or —$(CR_AR_B)_j$— (in which j is an integer of 1 to 4, $R_A$ and $R_B$ are each independently selected from hydrogen atom or alkyl group)], or $R^5$ and $R^6$ are optionally combined with each other to form optionally substituted cycloalkyl group, or optionally substituted heterocycle group, or a pharmacologically acceptable salt thereof.

7. The compound of claim 6, wherein Het is aryl group or heteroaryl group, or a pharmacologically acceptable salt thereof.

8. The compound of claim 6, wherein n is 1, or a pharmacologically acceptable salt thereof.

9. The compound of claim 6, wherein D is a group of formula:

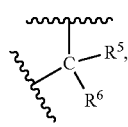

or a pharmacologically acceptable salt thereof.

10. A compound selected from the following group, or a pharmacologically acceptable salt thereof:

N-[5-cyclopropyl-6-(4-hydroxypiperidin-1-yl)pyridin-3-yl]-1-(2,4-dichlorophenyl)-5-methyl-1H-pyrazole-4-carboxamide;

N-{5-cyclopropyl-6-[4-(2-hydroxyethyl)piperidin-1-yl]pyridin-3-yl}-1-(4-fluorophenyl)-5-methyl-1H-pyrazole-4-carboxamide;

1-(4-chlorophenyl)-N-[5-cyclopropyl-6-(4-hydroxypiperidin-1-yl)pyridin-3-yl]-5-methyl-1H-pyrazole-4-carboxamide.

* * * * *